(12) United States Patent
Wu et al.

(10) Patent No.: US 8,536,545 B2
(45) Date of Patent: Sep. 17, 2013

(54) DELAYED EMISSION DETECTION DEVICES AND METHODS

(75) Inventors: Jigang Wu, Shanghai (CN); Shuo Pang, Pasadena, CA (US); Changhuei Yang, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 13 days.

(21) Appl. No.: 13/228,448

(22) Filed: Sep. 9, 2011

(65) Prior Publication Data

US 2012/0061587 A1    Mar. 15, 2012

Related U.S. Application Data

(60) Provisional application No. 61/381,389, filed on Sep. 9, 2010.

(51) Int. Cl.
*G01N 21/64*    (2006.01)
(52) U.S. Cl.
USPC ....................................................... 250/461.1
(58) Field of Classification Search
USPC .......................................... 250/459.1, 458.1
See application file for complete search history.

(56) References Cited

U.S. PATENT DOCUMENTS

| | | | |
|---|---|---|---|
| 4,438,330 A | 3/1984 | Hardy | |
| 4,692,027 A | 9/1987 | MacGovern et al. | |
| 4,737,621 A | 4/1988 | Gonsiorowski et al. | |
| 4,981,362 A | 1/1991 | DeJong et al. | |
| 5,061,076 A | 10/1991 | Hurley | |
| 5,196,350 A | 3/1993 | Backman et al. | |
| 5,247,167 A | 9/1993 | Bargerhuff et al. | |
| 5,252,834 A | 10/1993 | Lin | |
| 5,362,653 A | 11/1994 | Carr et al. | |
| 5,384,573 A | 1/1995 | Turpin | |
| 5,418,371 A | 5/1995 | Aslund et al. | |
| 5,426,505 A | 6/1995 | Geiser et al. | |
| 5,583,342 A | 12/1996 | Ichie et al. | |
| 5,587,832 A | 12/1996 | Krause | |
| 5,701,008 A | 12/1997 | Ray et al. | |
| 5,795,755 A | 8/1998 | Lemelson | |
| 5,798,262 A | 8/1998 | Garini et al. | |
| 5,936,764 A | 8/1999 | Kobayashi | |

(Continued)

FOREIGN PATENT DOCUMENTS

| | | |
|---|---|---|
| EP | 1 371 965 | 12/2003 |
| JP | 80-015156 | 1/1996 |

(Continued)

OTHER PUBLICATIONS

Cubeddu et al., "Time-gated fluorescence spectroscopy and imaging of porphyrins and phthalocyanines," 1991, SPIE Proceedings, vol. 1525, pp. 17-25.*

(Continued)

*Primary Examiner* — Kiho Kim
(74) *Attorney, Agent, or Firm* — Sheila Martinez-Lemke; Weaver Austin Villeneuve & Sampson LLP

(57) ABSTRACT

Embodiments of the present invention relate to a delayed emission detection device comprising a time-gated illumination source configured to provide excitation light to fluorophore during an excitation period and a light detector configured to receive emissions released from the fluorophore during a collection period after the excitation period.

24 Claims, 12 Drawing Sheets

(56) References Cited

U.S. PATENT DOCUMENTS

| | | | |
|---|---|---|---|
| 5,973,316 A | 10/1999 | Ebbesen et al. | |
| 6,133,986 A | 10/2000 | Johnson | |
| 6,143,247 A | 11/2000 | Sheppard, Jr. et al. | |
| 6,248,988 B1 | 6/2001 | Krantz | |
| 6,499,499 B2 | 12/2002 | Dantsker et al. | |
| 6,636,300 B2 | 10/2003 | Doemens et al. | |
| 6,753,131 B1 | 6/2004 | Rogers et al. | |
| 6,858,436 B2 | 2/2005 | Zenhausern et al. | |
| 7,045,781 B2 | 5/2006 | Adamec et al. | |
| 7,209,287 B2 | 4/2007 | Lauer | |
| 7,250,598 B2 | 7/2007 | Hollingsworth et al. | |
| 7,250,973 B2 | 7/2007 | Dobashi et al. | |
| 7,283,229 B2 | 10/2007 | Noguchi et al. | |
| 7,310,150 B2 | 12/2007 | Guillermo et al. | |
| 7,641,856 B2 | 1/2010 | Padmanabhan et al. | |
| 7,671,987 B2 | 3/2010 | Padmanabhan et al. | |
| 7,738,695 B2 | 6/2010 | Shorte et al. | |
| 7,751,048 B2 | 7/2010 | Yang et al. | |
| 7,768,654 B2 | 8/2010 | Cui et al. | |
| 7,773,227 B2 | 8/2010 | Yang et al. | |
| 7,982,883 B2 | 7/2011 | Cui et al. | |
| 8,039,776 B2 | 10/2011 | Cui et al. | |
| 8,189,204 B2 | 5/2012 | Cui et al. | |
| 8,314,933 B2 | 11/2012 | Cui et al. | |
| 2002/0159047 A1 | 10/2002 | Dubois | |
| 2003/0063204 A1 | 4/2003 | Suda | |
| 2003/0142291 A1 | 7/2003 | Padmanabhan et al. | |
| 2003/0174992 A1 | 9/2003 | Levene et al. | |
| 2003/0203502 A1 | 10/2003 | Zenhausern et al. | |
| 2003/0218756 A1 | 11/2003 | Chen et al. | |
| 2004/0156610 A1 | 8/2004 | Charlton et al. | |
| 2004/0175734 A1 | 9/2004 | Stahler et al. | |
| 2004/0224380 A1 | 11/2004 | Chou et al. | |
| 2005/0271548 A1 | 12/2005 | Yang et al. | |
| 2006/0003145 A1 | 1/2006 | Hansen et al. | |
| 2006/0013031 A1 | 1/2006 | Ravkin et al. | |
| 2006/0054502 A1* | 3/2006 | Peterman et al. | 204/450 |
| 2006/0152780 A1 | 7/2006 | Klug et al. | |
| 2007/0109619 A1 | 5/2007 | Eberl et al. | |
| 2007/0207061 A1 | 9/2007 | Yang et al. | |
| 2007/0258096 A1 | 11/2007 | Cui et al. | |
| 2007/0277192 A1 | 11/2007 | Hendriks et al. | |
| 2008/0008939 A1 | 1/2008 | Klug et al. | |
| 2008/0121790 A1 | 5/2008 | Grier | |
| 2008/0212430 A1 | 9/2008 | Bakker et al. | |
| 2008/0265177 A1 | 10/2008 | Connally et al. | |
| 2009/0101836 A1* | 4/2009 | Ohtsuka et al. | 250/458.1 |
| 2009/0179142 A1 | 7/2009 | Duparre et al. | |
| 2009/0225319 A1 | 9/2009 | Lee et al. | |
| 2009/0225411 A1 | 9/2009 | Cui et al. | |
| 2009/0231689 A1 | 9/2009 | Pittsyn et al. | |
| 2009/0276188 A1 | 11/2009 | Cui et al. | |
| 2010/0195873 A1 | 8/2010 | Cui et al. | |
| 2010/0309457 A1 | 12/2010 | Cui et al. | |
| 2011/0085219 A1 | 4/2011 | Yang et al. | |
| 2011/0170105 A1 | 7/2011 | Cui et al. | |
| 2011/0181884 A1 | 7/2011 | Cui et al. | |
| 2011/0205339 A1 | 8/2011 | Pavani et al. | |
| 2011/0205352 A1 | 8/2011 | Pavani et al. | |
| 2011/0226972 A1 | 9/2011 | Pang et al. | |
| 2011/0234757 A1 | 9/2011 | Zheng et al. | |
| 2012/0061554 A1 | 3/2012 | Cui et al. | |
| 2012/0061587 A1 | 3/2012 | Wu et al. | |
| 2012/0098950 A1 | 4/2012 | Zheng et al. | |

FOREIGN PATENT DOCUMENTS

| | | |
|---|---|---|
| JP | 2003-207454 A | 7/2003 |
| JP | 2003-0524779 A | 8/2003 |
| KR | 10-2005-0062531 | 6/2005 |
| WO | WO-0210713 A2 | 2/2002 |
| WO | WO-2004038484 A2 | 5/2004 |
| WO | WO 2008/107702 | 9/2008 |
| WO | WO 2009/111573 | 9/2009 |
| WO | WO 2011/035299 | 3/2011 |
| WO | WO 2011/047053 | 4/2011 |
| WO | WO 2011/106324 | 9/2011 |
| WO | WO 2011/106327 | 9/2011 |
| WO | WO 2012/033957 | 3/2012 |

OTHER PUBLICATIONS

"Lens (optics)," Wikipedia, last modified Aug. 18, 2010.

"Types of confocal microscopy," downloaded from the Internet at http://www.mikriskipie.org/2008/01/26/types-of-confocal-microscopy/14/ on Sep. 10, 2010.

Adams, Mark L,et al., "Microfluidic Integration on detector arrays for absorption and flourescence micro-spectrometers," Sensors and Actuators A, vol. 104, pp. 25-31 (2003).

Albensi, B. C., et al., "Elements of Scientific Visualization in Basic Neuroscience Research," BioScience, vol. 54, pp. 1127-1137 (2004).

Arnison, M. R., et al., "Linear Phase Imaging Using Differential Interference Contrast Microscopy," Journal of Microscopy, vol. 214, Part. I, pp. 7-12 (Apr. 2004).

Bates et al, "Multicolor super-resolution imaging with photo-switchable fluorescent probes," Science 317, 1749-1753 (2007).

Bethe, H.A., "Theory of Diffraction by Small Holes," The Physical Review, vol. 66, Nos. 7-8, pp. 163-182 (1944).

Betzig, E., et al.,"Imaging intracellular fluorescent proteins at nanometer resolution," Science, vol. 313, pp. 1642-1645 (2006).

Biddiss, Elaine, et al., "Hetergeneous Surface Charge Enhanced Micromixing for Electrokinetic Flows," Anal. Chem., vol. 76, pp. 3208-3213 (2004).

Booth, M. J., et al. , "Adaptive aberration correction in confocal microscope," Proceedings of the National Academy of Sciences of the United States of America, vol. 99, pp. 5788-5792 (Apr. 2002).

Boppart, S. A., et al., "Forward-imaging instruments for optical coherence tomography," Optics Letters, vol. 22, pp. 1618-1620 (1997).

Bouwkamp, C. J., "Diffraction theory," Reports on Progress in Physics XVIII, pp. 35-100 (1954).

Cao, Jinhua, et al., "Brownian Particle Distribution in Tube Flows," Proceedings of IMECE04, vol. 260, pp. 243-252 (2004).

Cogswell, C., et al., "Confocal Differential Contrast Interference (DIC) Microscopy: Including a Theoretical Analysis of Conventional and Confocal DIC Imaging," Journal of Microcscopy, vol. 165, Pt. 1, pp. 81-101 (Jan. 1992).

Conchello, Jose-Angel, and Lichtman, Jeff W., "Optical sectioning microscopy," Nature Methods, vol. 2, No. 12, pp. 920-931 (Dec. 2005).

Courjon, Daniel, "Near-field Microscopy and near-field optics," Imperial College Press, 317 pages (2003).

Creath, K., "Phase-measurement interferometry techniques," Prog. Opt., vol. 26, p. 44 (1988).

Cui, Xiquan, et al., "Lensless high-resolution on-chip optofluidic microscopes for Caenorhabditis elegans and cell imaging," Proceedings of the National Academy of Sciences of the Unities States of America, vol. 105, pp. 10670-10675 (2008).

Cui, Xiquan, et al., "Portable optical microscope-on-a-chip," Proc. SPIE, vol. 6095, pp. 609509-1-609509-8 (Jan. 2006).

Dahan, M., et al., "Time-gated biological imaging by use of collidal quantum dots," Optics Letters, vol. 26, No. 11, pp. 825-827 (2001).

De Fornel, F., "Evanescent waves from Newtonian optics and Atomic optics," Springer, 270 pages (2001).

Doyle, P. S., et al., "Self-assembled magnetic matrices for DNA separation chips," Science, vol. 295, No. 5563, p. 2237 (Mar. 2002).

Dunn, et al., "Introduction to Confocal Microscopy," available from MicroscopyU at http://www.microscopyu.com/articles/confocal (2007).

Ebbesen, T. W., et al., "EXtraordinary optical transmission through sub-wavelength hole arrays," Nature, vol. 391, No. 6668, pp. 667-669 (Feb. 1998).

Fowles, G. R., Introduction to Modern Optics, Dover Publications, Second Ed., pp. 57-61 (1989).

Frey, H.G., et al.,"High-resolution imaging of single fluorescent molecules with the optical near-field of a metal tip," Phys. Rev. Let. 93, 200801 (2004).

Fu, Anne Y., et al., "A microfabricated fluorescence-activated cell sorter," Nature Biotechnology, vol. 17, No. 11, pp. 1109-1111 (Nov. 1999).

Garcia De Abajo, F. J.,"Light transmission through a single cylindrical hole in a metallic film," Optics Letters, vol. 10, No. 25, pp. 1475-1484 (2002).

Giloh et al., "Fluorescence microscopy: reduced photobleaching of rhodamine and fluorescein protein conjugates by n-Propyl Gallate," Science 217, pp. 1252-1255 (1982).

Haglund, M. M., et al., "Enhanced optical imaging of human gliomas and tumor margins," Neurosurgery, vol. 38, pp. 308-317 (1996).

Heng, Xin, et al., "An Optical Tweezer Actuated, Nanoaperture-grid based Optofluidic Microscope Implimentation Method," Optics EXpress, vol. 15, No. 25, 16367-75 (2007).

Heng, Xin, et al., "Optofluidic Microscopy," Proceedings of the ICMM 2005 3rd International Conference on Microchannels and Minichannels, pp. 1-6 (2005).

Heng, Xin, et al., "Optofluidic Microscopy—a method for implementing a high resolution optical microscope on a chip," Lab Chip, vol. 6, pp. 1274-1276 (2006).

Heng, Xin, et al., "Portable Optical microscope-on-a-chip," Photonics West, San Jose, CA Jan. 2006.

Heng, Xin, et al., "Characterization of light collection through a subwavelength aperture from a point source," Optics EXpress, vol. 14, pp. 10410-10425 (2006).

Heng, Xin, et al "Optofluidic Microscope, a miniature microscope on a chip," 9th International Converence on Miniaturized Systems for Chemistry and Life Sciences (µTAS) (2005).

Hoffman, R., and Gross, L., "The modulation contrast microscope," Nature, vol. 254, pp. 586-588 (1975).

Hogenboom, C. A., et al., "Three-dimensional images generated by quadrature interferometry," Optics Letters, vol. 23, pp. 783-785 (1998).

Ikeda, T., et al., "Hilbert phase microscopy for investigating fast dynamics in transparent systems," Optics Letters, vol. 30, pp. 1165-1167 (2005).

Lamb, Don C., et al., Sensitivity Enhancement in Fluorescence Correlation Spectroscopy of Multiple Species Using Time-Gated Detection, Biophysical Journal, vol. 79, pp. 1129-1138 (Aug. 2000).

Lay, Christophe, et al., "Enhanced microfiltration devices configured with hydrodynamic trapping and a rain drop bypass filtering architecture for microbial cells detection," Lab Chip 2008, 8:830-833; published as Advanced Article on Apr. 1, 2008 at http://pubs.rsc.org | DOI:10.1039/b800015h.

Lee, Lap Man, et al., "The Application of on-Chip Optofluidic Microscopy for Imaging Giardia lamblia Trophozoites and Cysts," Biomed Microdevices, Springer DOI 10.1007/s10544-009-9312-X (2009).

Lew, Matthew et al., "Interference of a four-hole aperture for on-chip quantitative two-dimensional differential phase imaging," Optic Letters, vol. 32, No. 20, pp. 2963-2965 (Oct. 2007).

Lezec, H.J., and Thio, T., "Diffracted evanescent wave model for enhanced and suppressed optical transmission through subwavelength hole arrays," Optics EXpress, vol. 12, No. 16, pp. 3629-3651 (Aug. 2004).

Lichtman et al., "Fluorescence microscopy," Nat. Methods 2(12) (2005).

Liu, Shaorong R., "A microfabricated hybrid device for DNA sequencing," Electrophoresis 2003, vol. 24, No. 21, pp. 3755-3761 (2003).

Merenda, F., et al., "Miniaturized high-NA focusing-mirror multiple optical tweezers," Opt. EXp. 15, 6075-6086 (2007).

Murphy, et al., "Differential Interference Contrast (DIC)," available from Nikon MicrocopyU at http://www.microscopyu.com/articles/dic/dicindeX.html (2007).

Nott, Prabhu R., et al., "Pressure-driven flow of suspensions: simulation and theory," 1994, J. Fluid Mech., vol. 275, pp. 157-199.

Nozokido, Tatsuo, et al., "Scanning Near-Field Millimeter-Wave Microscopy Using a Metal Slit as a Scanning Probe," IEEE Transactions on Microwave Theory and Techniques, vol. 49, No. 3, 491-99 (2001).

United States Patent and Trademark Office (USPTO) Final Office Action in U.S. Appl. No. 12/399,823 mailed on May 25, 2012.

Popescu, G., et al., "Optical measurement of cell membrane tension," Physical Review Letters 97 (2006).

Probstein, R. F., "Physicochemical Hydrodynamics,"Wiley, 2nd Edition pp. 109-116, 123, 190-197, and 309-310 (2003).

Psaltis, Demetri, et al., "Developing optofluidic technology through the fusion of microfluidics and optics," Nature, vol. 442 (2006).

Rappaz, B., et al., "Measurement of the integral refractive indeX and dynamic cell morphometry of living cells with digital holographic microscopy," Optics EXpress, vol. 13, pp. 9361-9373 (2005).

Rust, M. J., et al., "Sub-diffraction-limit imaging by stochastic optical reconstruction microscopy (STORM)," Nature Methods, vol. 3, pp. 793-795 (2006).

Sanchez, E.J., et al., "Near-field fluorescence microscopy based on two-photon eXcitation with metal tips," Phys. Rev. Let. 82, 4014 (1999).

Schwiegerling, Jim, and Neal, Daniel,"Historical development of the Shack-Hartmann wavefront sensor," in Robert Shannon and Roland Shack: Legends in Applied Optics, edited by J. E. Harvey and R. B. Hooker_SPIE, Bellingham, WA, pp. 132-139 (2005).

Segre, G., et al., "Behavior of macroscopic rigid spheres in Poiseuille flow: Part 1. Determination of local concentration by statistical analysis of particle passages through crossed light beams," J. Fluid Mech., vol. 14, pp. 115-135 (1962).

Segre, G., et al., "Behavior of macroscopic rigid spheres in Poiseuille flow: Part 2. EXperimental results and interpretation," J. Fluid Mech., vol. 14, pp. 136-157 (1962).

Seo, Jeonggi, et al., "Disposable integrated microfluidics with SELF-aligned planar microlenses," Sensors and Acutators B, vol. 99, pp. 615-622 (2004).

Sommer, R.J, and Sternberg, P.W., "Changes of induction and competence during the evolution of vulva development in nematodes," Science 265, pp. 114-118 (1994).

Spring, Kenneth R., et al., "Introduction to Fluorescence Microscopy," <http://www.microscopyu.com/articles/fluorescence/fluorescenceintro.html> (Aug. 25, 2004).

Stanley, S.L., "Amoebiasis," Lancet 361, pp. 1025-1034 (2003).

Stone, H.A., et al., "Engineering Flows in Small Devices: Microfluidics Toward a Lab-on-a-Chip," Annu. Rev. Fluid Mech., vol. 36, pp. 381-411 (2004).

Tearney, G. J., et al., "Scanning single-mode fiber optic catheter-endoscope for optical coherence tomography," Optics Letters, vol. 21, pp. 543-545 (1996).

Tegenfeldt, Jonas O., et al., "Micro- and nanofluidics for DNA analysis," Analytical and Bioanalytical Chemistry, vol. 378, No. 7, pp. 1678-1692 (2004).

Tegenfeldt, Jonas O., et al., "Near-field Scanner for Moving Molecules," Physical review letters, vol. 86, No. 7, pp. 1378-1381 (Feb. 2001).

Thompson, Russell E., et al., "Precise nanometer localization analysis for individual fluorescent probes," Biophysical Journal, vol. 82, No. 5, pp. 2775-2783 ( May 2002).

Thorsen, Todd, et al., "Microfluidic Large-Scale Integration," Science, vol. 298, pp. 580-584 (2002).

Tokeshi, Manabu, et al., "Chemical processing on microchips for analysis, synthesis, and bioassay," Electrophoresis, vol. 24, No. 21, pp. 3583-3594 (2003).

Trau, D. et al., "Genotyping on a complementary metal oXide semiconductor silicon polymerase chain reaction chip with integrated DNA microarray," Analytical Chemistry, vol. 74, No. 13, pp. 3168-3173 (2002).

Tsien, Roger, et al., "Fluorophores for Confocal Microscopy: Photophysics and Photochemistry," Handbook of Biological Confocal Microscopy, third edition, Springer Science + Business Media, pp. 38-352 (2006).

Walker, Glenn, and Beebe, David, "A Passive Pumping Method for Microfluidic Devices," Lab Chip, pp. 131-134 (2002).

Wu, J., Cui, X. Lee, L. M., and Yang, C., "The application of Fresnel zone plate based projection in optofluidic microscopy," Opt. Exp. 16, 15595 (2008).

Zhu, Liang, et al., "Filter-based microfluidic device as a platform for immunofluorescent assay of microbial cells," Lab Chip, 2004, vol. 4, pp. 337-341; published as Advanced Article on Apr. 5, 2004 at http://pubs.rsc.org | DOI: 10.1039/b401834f.

Pang, Shuo, et al., "Fluorescence microscopy imaging with a Fresnel zone plate array based optofluidic microscope," Lab on a Chip 11, 3698-3702, (2011).
International Search Report in International Application No. PCT/US2005/016876 mailed on Oct. 16, 2006.
Written Opinion in International Application No. PCT/US2005/016876 mailed on Oct. 16, 2006.
International Search Report in International Application No. No. PCT/US2008/054908 mailed on Aug. 26, 2008.
Written Opinion in International Application No. PCT/US2008/054908 mailed on Aug. 26, 2008.
International Search Report in International Application No. PCT/US2009/036045 mailed on Apr. 23, 2009.
Written Opinion in International Application No. PCT/US2009/036045 mailed on Apr. 23, 2009.
International Search Report in International Application No. PCT/2009/036052 mailed on Jun. 29, 2009.
Written Opinion in International Application No. PCT/2009/036052 mailed on Jun. 29, 2009.
International Search Report and Written Opinion in International Application No. PCT/US2010/052512 mailed on Apr. 18, 2011.
International Search Report and Written Opinion in International Application No. PCT/US2010/049647 mailed on Apr. 29, 2011.
International Search Report and Written Opinion in International Application No. PCT/US2011/050901 mailed on Jul. 2, 2011.
United States Patent and Trademark Office (USPTO) Office Action in U.S. Appl. No. 11/125,718 mailed on Nov. 14, 2008.
United States Patent and Trademark Office (USPTO) Office Action in U.S. Appl. No. 11/125,718 mailed on Jul. 1, 2009.
United States Patent and Trademark Office (USPTO) Notice of Allowance in U.S. Appl. No. 11/125,718 mailed on Mar. 11, 2010.
United States Patent and Trademark Office (USPTO) Office Action in U.S. Appl. No. 12/797,132 mailed on Oct. 15, 2010.
United States Patent and Trademark Office (USPTO) Notice of Allowance in U.S. Appl. No. 11/686,095 mailed on Feb. 25, 2010.
United States Patent and Trademark Office (USPTO) Office Action in U.S. Appl. No. 11/686,095 mailed onJan. 10, 2008.
United States Patent and Trademark Office (USPTO) Office Action in U.S. Appl. No. 11/686,095 mailed on Jul. 17, 2008.
United States Patent and Trademark Office (USPTO) Office Action in U.S. Appl. No. 11/686,095 mailed on Feb. 26, 2009.
United States Patent and Trademark Office (USPTO) Office Action in U.S. Appl. No. 11/686,095 mailed on Oct. 28, 2009.
United States Patent and Trademark Office (USPTO) Office Action in U.S. Appl. No. 12/785,635 mailed on Oct. 15, 2010.
United States Patent and Trademark Office (USPTO) Restriction Requirement in U.S. Appl. No. 12/398,050 mailed on Aug. 10, 2011.
United States Patent and Trademark Office (USPTO) Office Action in U.S. Appl. No. 12/398,050 mailed on Nov. 14, 2011.
United States Patent and Trademark Office (USPTO) Notice of Allowance in U.S. Appl. No. 12/398,050 mailed on Jul. 17, 2012.
United States Patent and Trademark Office (USPTO) Office Action in U.S. Appl. No. 12/638,518 mailed on Jan. 12, 2012.
United States Patent and Trademark Office (USPTO) Notice of Allowance in U.S. Appl. No. 12/638,518 mailed on Feb. 14, 2012.
United States Patent and Trademark Office (USPTO) Notice of Allowance in U.S. Appl. No. 12/638,518 mailed on Apr. 23, 2012.
United States Patent and Trademark Office (USPTO) Office Action in U.S. Appl. No. 12/398,098 mailed on May 25, 2011.
United States Patent and Trademark Office (USPTO) Restriction Requirement in U.S. Appl. No. 12/399,823 mailed on Aug. 10, 2011.
United States Patent and Trademark Office (USPTO) Non-Final Office Action in U.S. Appl. No. 12/399,823 mailed on Nov. 14, 2011.
United States Patent and Trademark Office (USPTO) Notice of Allowance in U.S. Appl. No. 12/398,050 dated on Aug. 28, 2012.
United States Patent and Trademark Office (USPTO) Notice of Allowance in U.S. Appl. No. 12/638,518 dated on Aug. 24, 2012.
United States Patent and Trademark Office (USPTO) Non-Final Office Action in U.S. Appl. No. 12/903,650 dated on Jan. 14, 2013.
PCT International Preliminary Report on Patentability and Written Opinion dated Sep. 16, 2010 issued in PCT/US2009/036045.
European Search Report dated Feb. 11, 2013 issued in EP 09 716 850.4.
PCT International Preliminary Report on Patentability and Written Opinion dated Apr. 5, 2012 issued in PCT/US2010/049647.
PCT International Preliminary Report on Patentability and Written Opinion dated Apr. 26, 2012 issued in PCT/US2010/052512.
"Beam Steering Using Liquid Crystals," Boulder Nonlinear Systems, downloaded from the Internet at http://www.bnonlinear.com/papers/LCBeamSteering.pdf, 4 pp, May 8, 2001.
"Talbot Effect," Wikipedia, 3 pp, last modified Dec. 27, 2011.
"Confocal Microscopy," Wikipedia, 3 pp, last modified Aug. 25, 2010.
"Nipkow Disk" Wikipedia, 4 pp, last modified Aug. 13, 2010.
Beebe, David J., et al., "Physics and Applications of Microfluidics in Biology," *Annu. Rev. Biomed., Eng.*, 4:261-286 (2002).
Besold, G. and Lindlein, "Fractional Talbot effect for periodic microlens arrays", *Optics Engineering*, 36:1099-1105 (Apr. 1997).
Bishara et al., "Lensfree on-chip microscopy over a wide field-of-view using pixel super-resolution," *Opt. Expr.* 18:11181-11191 (2010).
Cheng, Ya, et al., "Microfluidic laser embedded in glass by three-dimensional femtosecond laser microprocessing," *Optics Letters*, 29(17):2007-2009 (2004).
Chovin, Arnaud, et al., "Fabrication, Characterization, and Far-Field Optical Properties of an Ordered Array of Nanoapertures," *Nano Letters*, 4(10):1965-68 (2004).
Chronis, Nikolas, et al., "Total internal reflection-based biochip utilizing a polymer-filled cavity with a micromirror sidewall," *Miniaturisation for Chemistry, Biology & Bioengineering, Lab Chip*, 4:125-130 (2004).
Cui, X. et al., "Portable Optical microscope-on-a-chip," *Photonics West*, San Jose, CA Jan. 2006, 8 pp.
Di Mambro et al., "Sharpness limitations in the projection of thin lines by use of the Talbot experiment," *J. Opt. Soc. Am. A* 21:2276-2282 (2004).
Eah et al., "Nearly diffraction-limited focusing of a fiber axicon microlens," *Rev. Sci. Instruments* 74(11):4969-4971 (2003).
Grosjean et al., "Fiber MicroaXicons Fabricated by a Polishing Technique for the Generation of Bessel-Like Beams," *Applied Optics* 46(33):8061-8063 (2007).
Ho, J., et al., "Use of whole slide imaging in surgical pathology quality assurance: design and pilot validation studies," *Human Pathology* 37:322-331 (2006).
Jaiswal, Jyoti K., et al., "Long-term multiple color imaging of live cells using quantum dot biconjugates," *Nature Biotechnology*, 21:47-51 (2003).
Kimura, Yasuo, et al., "Compact optical head using a holographic optical element for CD players," *Appl. Opt.* 27:668-671 (1988).
Leger, J.R., et al, "Efficient array illuminator using binary-optics phase plates at fractional-Talbot planes," *Optics Letters* 15:288-290 (1990).
Lezec, H.J., et al. "Beaming Light from a Subwavelength Aperture," *Science*, 297(5582):820-822 (2002).
Liang, J. Z., et al., "Supernormal vision and high-resolution retinal imaging through adaptive optics," *Journal of the Optical Society of America*, 14(11):2884-2892 (Nov. 1997).
Lohmann, A.W. and Silva D.E., "An Interferometer based on the Talbot Effect," *Optics Communications*, 2(9):413-415 (Feb. 1971).
Marquet, Pierre, et al., "Digital holographic microscopy: a noninvasive contrast imaging technique allowing quantitative visualization of living cells with subwavelength axial accuracy," *Optics Letters*, 30(5): 468-470 (Mar. 2005).
Miao, Qin, et al., "Dual-modal three-dimensional imaging of single cells with isometric high resolution using an optical projection tomography microscope," *Journal of Biomedical Optics*, vol. 14, 3 pp (2009).
Montgomery, W.D., "Self-Imaging Objects of Infinite Aperture," *J. Opt. Soc. Am.*, 57: 772-775 (1967).
Oheim, "High-throughput microscopy must re-invent the microscope rather than speed up its functions," Commentary, *Brit, J. Pharm.* 152:1-4 (2007).
Pang, Sean, et al., "Implementation of a color-capable optofluidic microscope on a RGB CMOS color sensor chip substrate," *Lab on a Chip*, 10:411-414 (2010).

Patorski, "The self-imaging phenomenon and its applications," *Progress in Opt.* 27:3-108 (1989).
Pfeiffer, F., et al., "Hard-X-ray dark-field imaging using a grating interferometer," *Nature Materials* 7:134-137 (2008).
Pfeiffer, Franz, et al., "Phase retrieval and differential phase-contrast imaging with low-brilliance X-ray sources," *Nat. Phys*, 2:258-261 (published online on Mar. 26, 2006).
Planchon, et al., "Rapid three-dimensional isotropic imaging of living cells using Bessel beam plane illumination,"*Nat. Methods* 8(5) (2011).
Rojo, et al., "Critical comparison of 31 commercially available digital slide systems in pathology," *Int'l J. Surg. Path.* 14:285-305 (2006).
Talbot, "LXXVI. Facts relating to optical science. No. IV," *Philosophical Magazine Series* 39:401-407 (1836).
Tao et al., "The generation of an array of nondiffracting beams by a single composite computer generated hologram," *J. Opt. A: Pure Appl. Opt.* 7:40-46 (2005).
Titus, Charles M., et al., "Efficient, Accurate Liquid Crystal Digital Light Deflector," *Proc. SPIE*, 3633(1):244-253 (Jun. 1999).
Turunen, et al., "Holographic generation of diffraction-free beams," *Appl. Opt.* 27(19):3959-3962 (1988).
Wu, J., Cui, X., Lee, L. M., and Yang, C., "The application of Fresnel zone plate based projection in optofluidic microscopy," *Opt. Exp.* 16:15595, 8pp (2008).
Wu, J., et al., "Wide field-of-view microscope based on holographic focus grid illumination," *Optics Letters*, 35(13):2188-2190 (2010).
Wu, J., et al., "Focus grid generation by in-line holography," *Optics Express*, 18:14366-14374 (2010).
Wu, Jigang, et al., "Focal plane tuning in wide-field-of-view microscope with Talbot pattern illumination," *Optics Letters* 36(12):2179-2181 (2011).
Zapata-Rodriguez, Carlos, et al., "Three-dimensional Field Distribution in the Focal Region of Low-Fresnel-Number Axicons," *F. Opt. Soc. Am. A* 23(12):3016-3017 (2005).
Zheng, G.A., et al., "Sub-pixel resolving optofluidic microscope for on-chip cell imaging," *Lab on a Chip*, 10:3125-3129 (2010).
Zheng, G., et al., "Supplementary Information for: Sub-pixel resolving optofluidic microscope for on-chip cell imaging," *Lap Chip*, vol. 10 (2010).
Zheng, Guoan, "The ePetri dish, an on-chip cell imaging platform based on subpixel perspective sweeping microscopy (SPSM)," *Proceedings of the National Academy of Science* 108 (41):16889-94 (2011).
Zhu et al., "Generation of controllable nondiffracting beams using multimode optical fibers," *Appl. Phys. Lett.* 94, 201102, 3 pp (2009).
United States Patent and Trademark Office (USPTO) Notice of Allowance in U.S. Appl. No. 12/886,779 dated on May 22, 2013.
PCT International Preliminary Report on Patentability and Written Opinion dated Mar. 21, 2013 issued in PCT/US2011/050901.
Brockie et al., (Mar. 1, 2001) "Differential Expression of Glutamate Receptor Subunits in the Nervous System of *Caenorhabditis elegans* and Their Regulation by the Homeodomain Protein UNC-42," *The Journal of Neuroscience*, 21(5):1510-1522.
Cai et al., (Mar. 24, 2004) "Insulinoma-Associated Protein IA-2, a Vesicle Transmembrane Protein, Genetically Interacts with UNC-31/CAPS and Affects Neurosecretion in *Caenorhabditis elegans*," *The Journal of Neuroscience*, 24(12):3115-3124.
Collet et al., (Jan. 1998) "Analysis of *osm*-6 That Affects Sensory Cilium Structure and Sensory Neuron Function in *Caenorhabditis elegans*," *Genetics*, 148:187-200.

Cui, Xiquan, et al., (2008) "Quantitative differential interference contrast microscopy based on structured-aperture interference," *Applied Physics Letters*, vol. 93, pp. 091113-1—091113-3.
Cui, Xiquan, et al., (2006) "Slanted hole array beam profiler (SHArP)—a high-resolution portable beam profiler based on a linear aperture array," *Optics Letters*, 31(21):3161-3163.
Furtado et al., (2002) "Measurement of green fluorescent protein concentration in single cells by image analysis," *Analytical Biochemistry*, 310:84-92.
Garcia-Sucerquia, J. et al., (2006) "Immersion digital in-line holographic microscopy," *Optics Letters*, 31:1211-1213.
Hedgecock et al., (1985) "Axonal Guidance Mutants of *Caenorhabditis elegans* Identified by Filling Sensory Neurons with Fluorescein Dyes," *Developmental Biology*, 111:158-170.
"High Refractive Index/Low Refractive Index Resins", NTT AT, downloaded from the Internet at http://www.ntt-at.com/product/hl__resins/ [retrieved on Jun. 12, 2013], 3pp.
Lange et al., (2005) "A microfluidic shadow imaging system for the study of the nematode *Caenorhabditis elegans* in space," *Sensors and Actuators B*, 107:904-914.
Li et al., (1997) "Transport, Manipulation, and Reaction of Biological Cells On-Chip Using Electrokinetic Effects," *Anal. Chem*, 69:1564-1568.
Ottevaere et al., (2006) "Comparing glass and plastic refractive microlenses fabricated with different technologies," *Journal of Optics a-Pure and Applied Optics*, 8(7):S407-S429.
Perkins et al., (1986) "Mutant Sensory Cilia in the Nematode *Caenorhabditis elegans*," *Developmental Biology*, 117:456-487.
Resolution—"Airy Patterns and Resolution Criteria (3-D Version)," Olympus Fluo View Resource Center—Interactive Java Tutorials, downloaded from the Internet at http://www.olympusconfocal.com/java/resolution3d [retrieved on Jun. 12, 2013], 3pp.
Richard et al., (2009) "An integrated hybrid interference and absorption filter for fluorescence detection in lab-on-a-chip devices," *Lab on a Chip*, 9:1371:1376.
Ririe et al., (Dec. 23, 2008) "The *Caenorhabditis elegans* vulva: A post-embryonic gene regulatory network controlling organogenesis," *Proceedings of the National Academy of Sciences of the United States of America*, 105(51):20095-20099.
Seo, et al., (2009) "Lensfree holographic imaging for on-chip cytometry and diagnostics," *Lab on a Chip*, 9:777-787.
Slavich—"Technical specifications of holography materials," downloaded from the Internet at http://www.slavich.com/holo__summary [retrieved on Jun. 12, 2013], 2pp.
Tam et al., (May 24, 2004) "An imaging fiber-based optical tweezer array for microparticle array assembly," *Appl. Phys. Lett.*, 84(21):4289-4291.
Tsien, Roger, et al., (1998) "The green fluorescent protein," *Annual Review of Biochemistry*, 67:509-544.
Xu, W., Jericho, M., Meinertzhagen, I., Kreuzer, H., (2001) "Digital in-line holography for biological applications," *Proc Natl Acad Sci USA*, vol. 98, pp. 11301-11305.
Yanowitz, et al., (2005) "Cyclin D involvement demarcates a late transition in *C. elegans* embryogenesis," *Developmental Biology*, 279:244-251.

* cited by examiner

DELAYED EMISSION DETECTION DEVICES AND METHODS

CROSS-REFERENCES TO RELATED APPLICATIONS

This is a non-provisional application of, and claims priority to, U.S. Provisional Patent Application No. 61/381,389 entitled "Fluorescence Optofluidic Microscope" filed on Sep. 9, 2010. This provisional application is hereby incorporated by reference in their entirety for all purposes.

This non-provisional application is related to the following co-pending and commonly-assigned patent applications, which are hereby incorporated by reference in their entirety for all purposes:

U.S. patent application Ser. No. 12/903,650 entitled "Holographically Illuminated Imaging Devices" filed on Oct. 13, 2010.
U.S. patent application Ser. No. 12/398,050 entitled "Optofluidic Microscope Device with Photosensor Array" filed on Mar. 4, 2009.
U.S. patent application Ser. No. 12/886,779 entitled "Reflective Focusing and Transmissive Projection Device" filed on Sep. 21, 2010.

BACKGROUND OF THE INVENTION

Embodiments of the present invention generally relate to emission detection methods and devices (e.g., fluorescence microscopes). More specifically, certain embodiments relate to techniques for improving emission detection devices in applications such as microscopy and cytometry.

Fluorescence techniques are widely used in biomedical imaging and sensing to identify or detect microscopic structures, submicroscopic structures, even individual molecules. A fluorescence signal measured by devices using fluorescence techniques can also reveal cell dynamics and metabolism. An example of a fluorescence technique can be found in Giloh, H., and Sedat, J. W., "Fluorescence microscopy: reduced photobleaching of rhodamine and fluorescein protein conjugates by n-Propyl Gallate," Science 217, 1252-1255 (1982), which is hereby incorporated by reference in its entirety for all purposes. An example of a fluorescence technique that can identify submicroscopic structures can be found in Betzig, E., et al., "Imaging intracellular fluorescent proteins at nanometer resolution," Science 313, 1642-1645 (2006) and Bates, M., et al., which is hereby incorporated by reference in its entirety for all purposes.

Conventional fluorescence microscopes are common tools that use fluorescence techniques to investigate biological problems. Usually, a reagent (e.g., fluorescence/phosphorescence dye) is mixed with a sample to mark or tag portions of the object (e.g., cell) under investigation with fluorophore(s). A fluorophore refers to a component of a molecule that causes the molecule to fluoresce or phosphoresce once excited. A fluorophore can absorb energy from excitation light of a specific wavelength(s) and re-emit the energy at a different wavelength(s). A conventional fluorescence microscope irradiates the sample with excitation light of predetermined wavelength(s) (e.g., blue light) to activate fluorophore(s) in the sample. In response, fluorophore(s) release fluorescence/phosphorescence emissions of different wavelength(s) (e.g., red light). Most conventional fluorescence microscopes include filters to reject excitation light and allow the weaker fluorescence/phosphorescence emissions signal to be detected.

BRIEF SUMMARY OF THE INVENTION

Embodiments of the present invention relate to techniques for improving emission detection methods and devices. One technique of embodiments uses a delayed emission detection device (DEDD) employing a delayed emission detection strategy to illuminate an object with excitation light and delay detecting the emissions until after the excitation light is no longer present. This delayed emission detection strategy can eliminate the need of a filter to remove the excitation light to isolate the emissions. Another technique of related embodiments uses a reflective coating to direct (reflect and/or collimate) light to a light detector. In applications utilizing a filter, this technique can focus weak emissions to improve collection efficiency. This technique can also collimate excitation light at the filter, which can improve the removal of the excitation light by the filter and thus improve the signal to noise ratio. The above techniques, together with others specifically mentioned below and other emission detection techniques can be employed separately or in combination to improve the capabilities of emission detection methods and devices.

One embodiment is directed to a delayed emission detection device comprising a time-gated illumination source configured to provide excitation light to fluorophore during an excitation period and a light detector configured to receive emissions from the fluorophore during a collection period after the excitation period. The light detector avoids receiving excitation light during the collection period.

Another embodiment is directed to a method of detecting emissions with a delayed emission detection device. The method comprises providing, by a time-gated illumination source, excitation light to fluorophore during an excitation period. The method also comprises receiving, by a light detector, emissions from the fluorophore during a collection period after the excitation period.

Another embodiment is directed to a delayed emission detection system, comprising a delayed emission detection device and a processor. The delayed emission detection device comprises a time-gated illumination source configured to provide excitation light to fluorophore during an excitation period and a light detector configured to receive emissions from the fluorophore during a collection period after the excitation period. The processor is configured to receive a signal from the light detector with emissions data. In some cases, the processor can use the emission data to analyze (e.g., image) an object with the fluorophore receiving the excitation light.

Another embodiment is directed to an optofluidic delayed emission detection device comprising a body, a time-gated illumination source, and a light detector. The body comprises a fluid channel having a surface layer with an aperture array. The time-gated illumination source is configured to provide excitation light to fluorophore in the fluid channel through the aperture array during one or more excitation periods. The light detector is configured to receive, from the fluid channel, emissions from the fluorophore during a collection period after each excitation period.

Another embodiment is directed to an optofluidic delayed emission detection device comprising a body, an illumination source, and a light detector. The body comprises a fluid channel having a surface layer with an aperture. The illumination source is configured to provide excitation light to fluorophore in a fluid channel through the aperture. The light detector comprises a detection region located downstream from the aperture. The detection region is configured to receive emissions from the fluorophore and avoid receiving excitation light through the aperture.

Another embodiment is directed to an optofluidic emission detection device comprising a body having a fluid channel. The body includes a first and second opposing surface layers proximal the fluid channel. The second surface layer has a light transmissive region. The fluid channel is configured to receive excitation light from an illumination source through the light transmissive region. The optofluidic emission detection device also includes a light detector located outside the first surface layer and a filter located in the first surface layer. The filter is configured to pass emissions from the fluid channel to the light detector. The optofluidic emission detection device also includes a reflective coating in the body. The reflective coating is configured to reflect light in the fluid channel to the first surface layer. In some cases, the body further comprises a channel outlier having an inner surface with a portion of the reflective coating. The portion of the reflective coating on the inner surface of the channel outlier is configured to collimate the reflected light to the light detector. In one case, the inner surface of the channel outlier is a parabolic surface having a focus line in a plane parallel to a surface of the first surface layer.

These and other embodiments of the invention are described in further detail below.

DETAILED DESCRIPTION OF THE INVENTION

Figure 1:
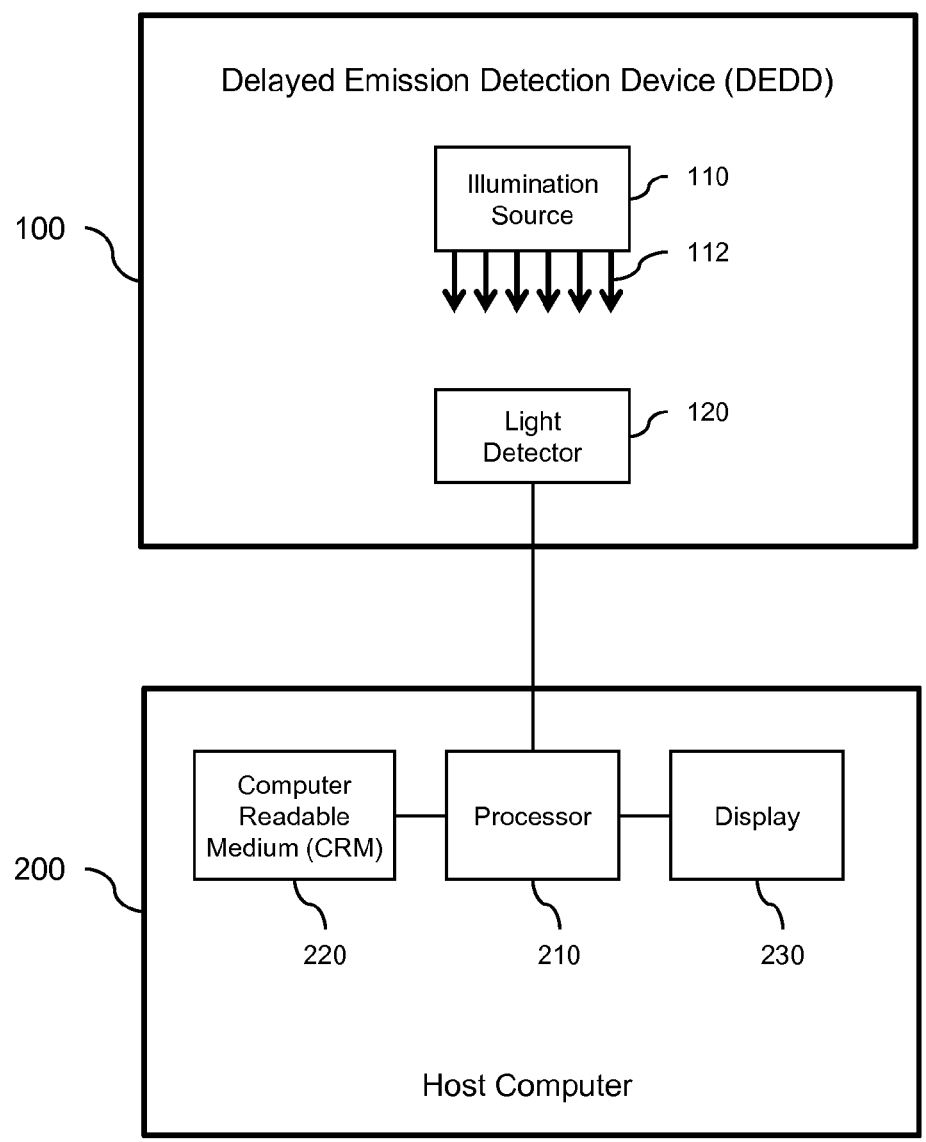
FIG. 1 a block diagram of a delayed emission detection system including a DEDD coupled to a host computer, according to embodiments of the invention.

Embodiments of the present invention will be described below with reference to the accompanying drawings. Embodiments are directed to techniques for improving emission detection devices (e.g., florescence microscopes) used to analyze objects (e.g., cells, submicroscopic structures, molecules, etc.) in a sample.

A first technique uses a DEDD employing a delayed emission detection strategy to eliminate the need for an excitation light filter that is usually necessary in conventional emission detection devices. In embodiments of the invention, an illumination source provides an excitation light to a sample, and a light detector receives and detects fluorescent/phosphoresce emissions from the sample. The light detector and illumination source are configured so that light detector delays detection until the excitation light is no longer present or detectable. Once the excitation light is absent, the light detector can measure the isolated emissions without the need of a filter to eliminate the excitation light. Various scenarios can be employed.

In a first scenario, a time-gated illumination source (e.g. pulsed laser) provides time-gated excitation light during an excitation period. The light detector is synchronized with the time-gated illumination source to detect emissions during a detection period after the excitation period.

In a second scenario, the DEDD further includes a fluid channel having a fluid flow carrying the object being examined. A surface layer of the fluid channel has an aperture array. A time-gated illumination source provides time-gated excitation light through the aperture array into the fluid channel during an excitation period. The light detector is synchronized with the time-gated illumination source to detect emissions from the fluid channel after the excitation period as the object(s) move through the fluid channel. Alternatively, an array of metal probes can be placed on the inside surface of the surface layer of the fluid channel instead of the aperture array. The metal probes can provide near field excitation light at their tips.

In a third scenario, a continuous illumination source provides continuous excitation light through an aperture(s) (e.g., slit) in the surface layer of a fluid channel as an object moves in a fluid flow through the fluid channel. A detection region of the light detector located downstream from the aperture(s) and out of range of the excitation light can measure emissions. In this scenario, the DEDD relies on the physical offset of the detection region to avoid excitation light. These three scenarios can be employed separately or in combination to improve emission detection methods and devices.

A second technique uses a reflective coating on the inside surface of a fluid channel or on a parabolic channel outlier located outside the fluid channel. The reflective coating directs and/or collimates light to a light detector to one side of the fluid channel. An excitation light filter is located between the fluid channel and the light detector to allow emissions and reject excitation light. By reflecting the light to the light detector, this technique improves collection of the weak emissions. Collimation of the light can allow for more effective elimination of the excitation light by the filter.

Embodiments of the invention provide one or more technical advantages and improvements of emission detection devices. A main advantage of several DEDD embodiments is that it can detect emissions when the excitation is no longer present and without the need of an excitation light filter. Most conventional fluorescence microscopes have excitation light filters, which can remove most excitation light. However, many of these filters may allow some excitation light which can introduce noise to the signal. Since fluorescence emissions can be weak, any noise can be significant in reducing signal quality. By avoiding excitation light altogether, the DEDD does not have to remove the excitation light with a filter and does not have to contend with noise that may result from any residual excitation light. The DEDD improves the signal to noise ratio and thus, the quality of any resulting fluorescence image or other results. Moreover, by eliminating the need for a filter, the DEDD reduces manufacturing complexity and cost. An advantage of using the DEDD of scenario 3 over other embodiments may be that it does not need time-gated excitation or synchronization of the illumination source and the light detector. In Scenario 3, the DEDD uses continuous light and relies on the physical offset of the detection region to avoid excitation light. The DEDD of this scenario may be a low cost alternative in many cases.

An advantage of the reflective coating of embodiments is that they more efficiently collect weak emissions at the light detector. If the reflective coating is located on a parabolic surface, the light can be collimated to maximize detection of emissions and filter effectiveness. Thus, the reflective coating on the parabolic surface improves removal of the excitation light and the signal to noise ratio. An additional advantage is that the collimation by the parabolic reflective surface is wavelength independent.

Technique I—Delayed Emission Detection

I. Delayed Emission Detection System

FIG. 1 is a block diagram of a delayed emission detection system 10 including a DEDD 100 coupled to a host computer 200, according to embodiments of the invention. A DEDD 100 refers to a device or combination of devices capable of detecting light according to a delayed detection strategy, which delays detecting emissions until after the excitation light is no longer present or detectable.

In FIG. 1, the DEDD 100 includes an illumination source 110 providing excitation light 112 and a light detector 120 for receiving and detecting light. The host computer 200 includes a processor 210, a computer readable medium (CRM) 220, and a display 230. The processor 210 is in communication with the light detector 120, the CRM 220, and the display 230. Although the illustrated example shows a single DEDD 100, a single host computer 200, and single components of the DEDD 100 and host computer 200, any suitable numbers of these components can be used in other embodiments.

Figure 2:
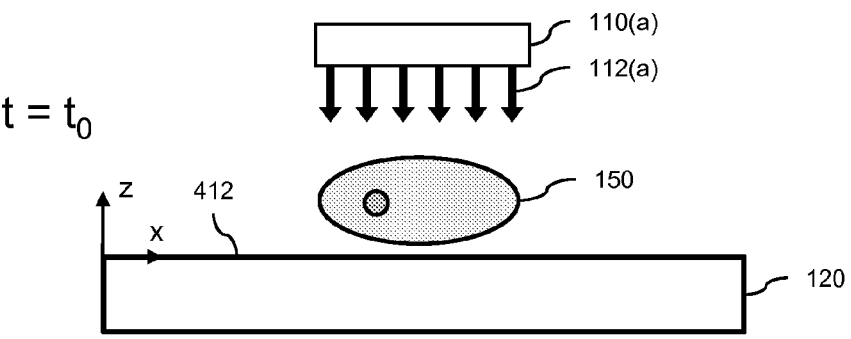
FIGS. 2(a) and 2(b) are schematic drawings of a cross-sectional view of components of a DEDD employing scenario 1 of the delayed detection strategy, according to an embodiment of the invention.
Figure 2:
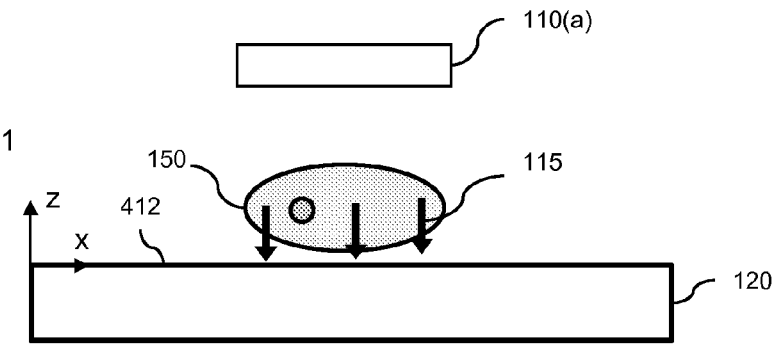
Figure 5:
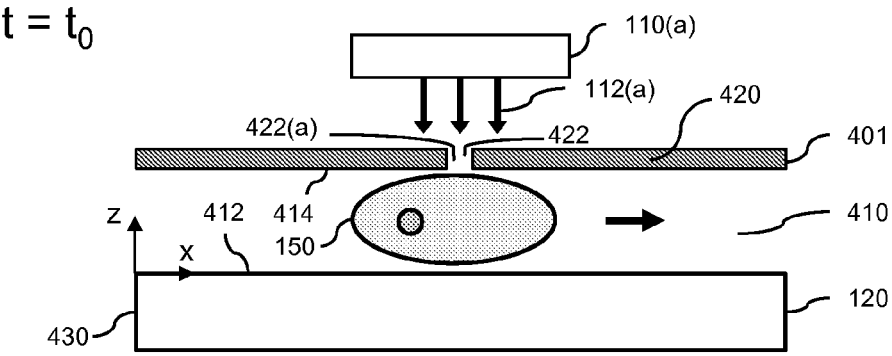
FIGS. 5(a) and 5(b) are schematic drawings of a side view of components of an optofluidic DEDD employing Scenario 2 of the delayed detection strategy, according to an embodiment of the invention.
Figure 5:
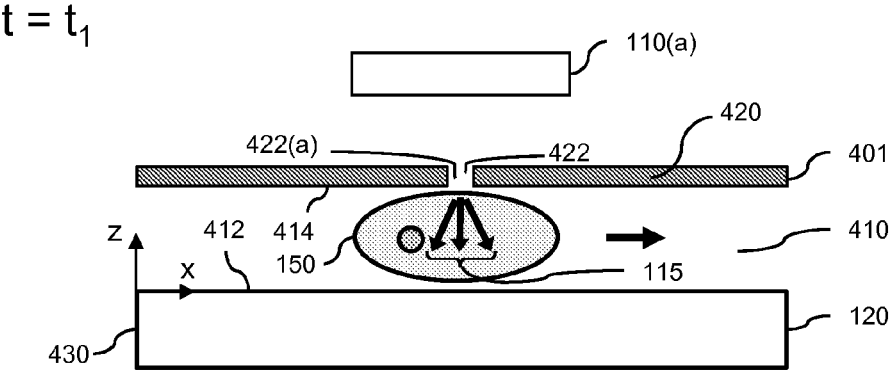
Figure 8:
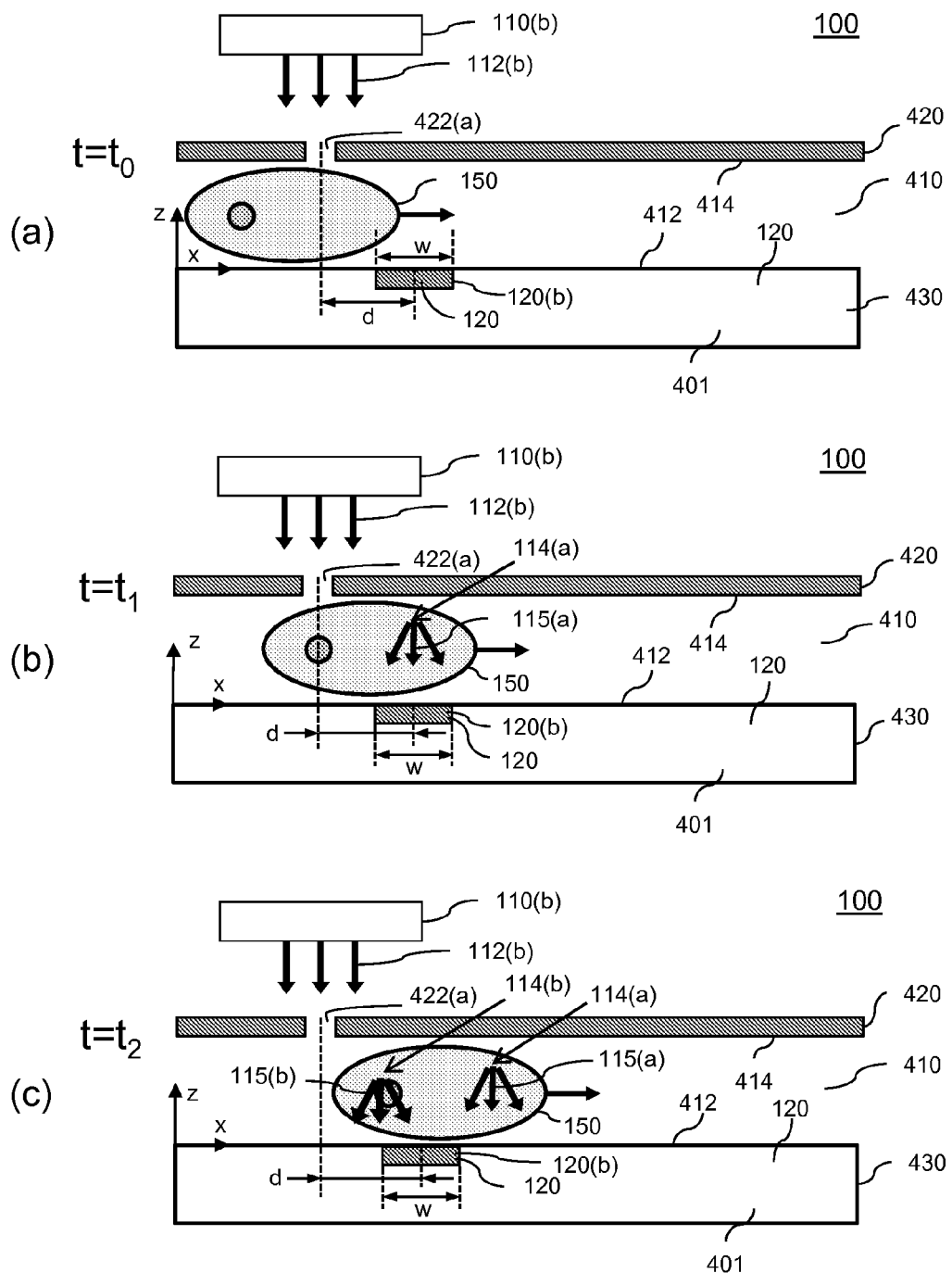
FIGS. 8(a), 8(b) and 8(c) are schematic drawings of a side view of components of an optofluidic DEDD employing Scenario 3 of the delayed detection strategy, according to an embodiment of the invention.

In operation, the illumination source 110 provides excitation light 112 to a sample having an object (such as the object 150 shown in FIG. 2) being analyzed by the DEDD 100. In response to receiving and absorbing excitation light 112, fluorophore(s) in the object releases emissions 115 (as shown in FIGS. 2, 5, and 8) associated with the absorbed excitation light 112. Emissions 115 can refer to light re-emitted by fluorophore(s) in the sample corresponding to excitation light 112 absorbed by the fluorophore(s). To employ the delayed detection strategy, the light detector 120 and illumination source 110 are configured so that the light detector 120 delays detecting emissions 115 until after the excitation light 112 from the illumination source 110 is no longer present and/or detectable by the light detector 120. In this way, the light detector 120 detects emissions 115 and avoids detecting excitation light 112 without using an excitation filter. A signal having light data associated with the emissions 115 is sent to the processor 210, which executes code stored on the CRM 220 to analyze the light data. The processor 210 sends a signal with analysis results (e.g., a fluorescent image of an object 150 in the sample) to the display 230 for output to a user of the delayed emission detection system 10.

Figure 7:
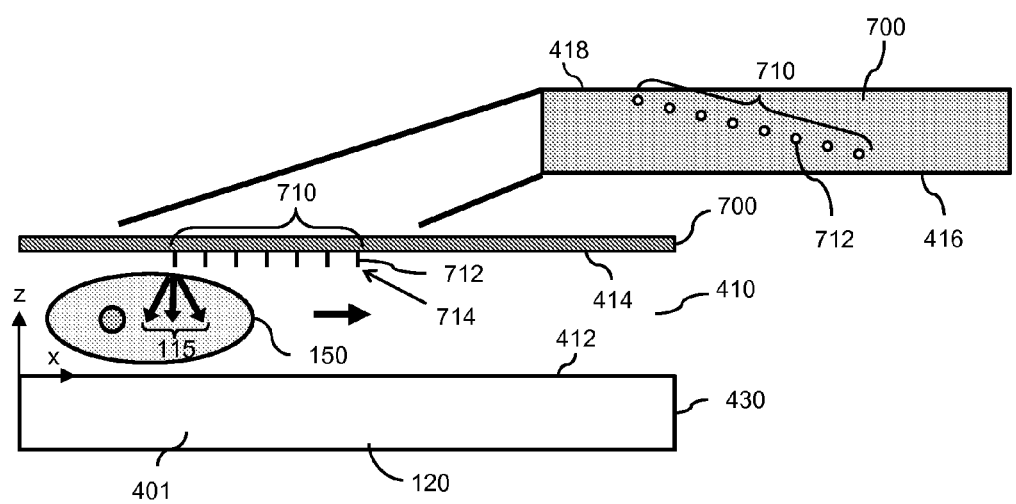
FIG. 7 includes schematic drawings of a side view and bottom view of components of a optofluidic DEDD employing Scenario 2 and having small metal probes, according to an embodiment of the invention.

The DEDD 100 and other emission detection devices of embodiments include an illumination source 110. An illumination source 110 refers to any suitable device or combination of devices and/or other source of light (e.g. ambient light, thermal sources, etc.) capable of providing excitation light 112 to the sample being analyzed. Suitable devices are naturally and/or commercially available. Some examples of suitable devices include thermal sources, LEDs, continuous-wave lasers, pulsed lasers, etc. The illumination source 110 may provide excitation light 112 to any suitable portion of the sample or to the entire sample. For example, the illumination source 110 may provide excitation light 112 to the entire sample as shown in FIG. 2. The illumination source 110 may use a suitable structure (e.g., aperture, aperture array, holographic plate generating array of focal spots, focus array generator, etc.) capable of providing excitation light 112 to a portion of the sample. For example, the illumination source 110 may provide excitation light 112 through an aperture to a local area of the sample as shown in FIG. 5. In another example, the illumination source 110 may use a metal probe to provide excitation light 112 to local area of the sample as shown in FIG. 7. In yet another example, the illumination source 110 may use a focused beam array generator to generate a focused beam array of excitation light as shown in FIG. 4(c).

Excitation light 112 refers to any suitable type of light capable of activating fluorophore(s) in the sample being examined. Excitation light 112 may have any suitable light property or properties (e.g., wavelengths, intensities, polarizations, phases, etc.) for suitably activating fluorophore(s) in the sample to cause the release of emissions 115. For example, the excitation light may have an intensity level that is suitable to generate emissions 115 at an intensity level detectable by the light detector 120. The excitation light 112 may be of any suitable type (e.g., continuous, time-gated, etc.). Illustrated examples of DEDDs 100 providing time-gated excitation light 112(a) are shown in FIG. 2 and FIG. 5. An illustrated example of a DEDD 100 providing continuous excitation light 112(b) is shown in FIG. 8.

In some embodiments, such as illustrated examples in FIGS. 2 and 5, the DEDD 100 includes a time-gated illumination source 110(a), which is an illumination source (e.g., pulsed LED, pulsed laser, etc.) capable of providing time-gated excitation light 112(a) during one or more excitation periods. In embodiments, the illumination source 110(a) may be a pulsed laser providing pulses of excitation light 112(a) to the sample. Some examples of suitable pulsed lasers include mode locked lasers, Q switch lasers, etc.

In DEDDs 100 having a time-gated illumination source 110(a), time-gated excitation light 112(a) may be provided during one or more excitation periods. An excitation period refers to a time interval during which the time-gated illumination source 110(a) provides time-gated excitation light 112(a). In embodiments, the intensity profile of the time-gated excitation light 112(a) on the temporal domain during the excitation period may form a square wave. In other embodiments, the intensity profile on the temporal domain may have other forms.

The durations of the one or more excitation periods can be any suitable value or values. In some embodiments, the duration of the one or more excitation periods can be determined based on the fluorophore used. In many cases, the duration of the excitation period can be in the range of femtosecond to nanosecond range ($10^{-12}$ to $10^{-9}$ second). In other cases, the duration of the excitation period can be up to the millisecond range. In embodiments with multiple excitation periods, the durations of the excitation periods can be a constant in some cases or can have different values in other cases.

In FIG. 1, the illumination source 110 is a component of the DEDD 100. In other embodiments, the illumination source 110 may be separate from the DEDD 100 and/or the delayed emission detection system 10. The illumination source 110 may be placed in any suitable location and/or may include suitable components (e.g., reflective surfaces, lens, aperture array as shown in FIG. 4(b), etc.) to direct excitation light 112 to the sample as required. Although embodiments describe an illumination source 110 capable of providing only excitation light 112, the illumination source 110 of other embodiments may provide other light or may provide excitation light 112 and other light to the sample.

The DEDD 100 in FIG. 1 and other emission detection devices of embodiments include a light detector 120 for receiving and detecting light. A light detector 120 (e.g., a photosensor) refers to any suitable device or combination of devices capable of receiving light and generating signal(s) with light data based on light received. The signal(s) may be in the form of electrical current from the photoelectric effect. In most embodiments, such as the illustrated example shown in FIG. 4(c), the light detector 120 includes one or more discrete light detecting elements 120(a) (e.g., pixels). Each light detecting element 120(a) can generate a signal with light data based on light received.

Light data refers to any suitable information related to light received by the light detector 120. Light data may include, for example, information about the properties of the light detected such as the intensity of the light, the wavelength(s) of the light, the frequency or frequencies of the light, the polarization(s) of the light, the phase(s) of the light, the spin angular momentum(s) of the light, and/or other light properties associated with the light detected by the light detector 120. Light data may also include the location of the light detecting element 120(a) receiving the light and generating a specific signal. The light data may also include the time that the light was detected by a particular light detecting element 120(a). Light data may be data based on a single (sample) time, based on multiple (sample) times, or based on a time-varying basis. In some embodiments, such as the optofluidic embodiments, light data may be time-varying light data.

The signal(s) generated by the light detector 120 may include emissions data, which is light data associated with emissions 115 (as shown in FIGS. 2, 5, and 8) received by the light detector 120. In embodiments, the DEDD 100 has a light detector 120 that avoids excitation light 112 and detects only or primarily emissions 115. In these embodiments, the light detector 120 may generate signal(s) with only or primarily emissions data.

The light detecting elements 120(a) of the light detector 120 can be arranged in any suitable form such as a single light detecting element 120(a), a one-dimensional array of light detecting elements 120(a), a two-dimensional array of light detecting elements 120(a), or a multiplicity of one-dimensional and/or two-dimensional arrays of light detecting elements 120(a). The arrays can be in any suitable orientation or combination of orientations. Some examples of light detectors having a single light detecting element 120(a) include a photo-diode (PD), an avalanche photo-diode (APD) and a photomultiplier tubes (PMT). Some examples of light detectors 120 having one-dimensional or two-dimensional arrays include a charge coupled device (CCD) array, a complementary metal-oxide-semiconductor (CMOS) array, an APD array, a PD array, a PMT array, etc. Other suitable light detectors 120 are commercially available. Each light detecting element 120(a) may be of any suitable size (e.g., 1-10 microns) and any suitable shape (e.g., circular or square). For example, a complementary metal-oxide-semiconductor (CMOS) or charge coupled device (CCD) light detecting element 120(a) may be 1-10 microns and an APD or PMT light detecting element 120(a) may be as large as 1-4 mm.

In one embodiment shown in FIG. 8, the light detector 120 has a detection region 120(b). The detection region 120(b) refers to one or more light detecting elements 120(a) that are located to detect only or primarily emissions 115 and avoiding excitation light 112. For example, the detection region 120(b) in FIG. 8 is located away from an area receiving excitation light 112 so that the detection region 120(b) receives only or primarily emissions 115. The detection region 120(b) may include any number of light detecting elements 120(a) (e.g., 1, 5, 10, 20, 100, etc.) in any arrangement. In some cases, the detection region 120(b) includes all the light detecting elements 120(a) of the light detector 120. In other cases, the detection region 120(b) may be a portion or region (area) of the light detector 120. For example, the detection region 120(b) may include one or more one-dimensional arrays of light detecting elements 120(a) in a light detector 120 comprising a two-dimensional array of light detecting elements 120(a). Although embodiments show a single detection region 120(b), the light detector 120 of other embodiments may have more detection regions 120(b). In some cases, there may a space in between the detection regions 120(b). The detection regions can be arranged in any pattern (e.g., checkerboard, etc.) or randomly arranged.

In some embodiments of the DEDD 100, such as the embodiments illustrated in FIGS. 2 and 5, the light detector 120 detects light during at least one collection period. A collection period refers to a time interval during which the light detector 120 receives and detects only or primarily emissions 115. In embodiments, the collection period occurs after the end of an excitation period and before any other excitation period begins. In these embodiments, the light detector 120 and the illumination source 110 are synchronized so that the collection period is substantially separate from the excitation period. That is, the collection period does not overlap significantly with the excitation period. In some cases, the collection period starts after a suitable time delay after the end of an excitation period. For example, the delay can be in the range of femtoseconds to nanoseconds. In other cases, the collection period may start immediately after the end of an excitation period without any delay.

The collection period may have any suitable duration (e.g., 1 second, 0.1 seconds, 0.01 seconds, 20 seconds, etc.). The duration may be predetermined in some cases before the capturing run. In other cases, the collection period may end after an event has occurred. For example, the collection period may end when it is determined that the detected emissions 115 have decayed to a predefined level. The predefined level may be any suitable level of one or more light properties. For example, the predefined level may be a percentage (e.g., 50%, 30%, 10%, etc.) of the maximum intensity detected by the light detector 120 during the analysis by the DEDD 100, the minimum intensity detectable by the light detector 120, a percentage (e.g., 50%, 30%, 10%, etc.) of the maximum intensity detectable by the light detector 120, an intensity value associated with the fluorescence dye in the sample, etc.

In one embodiment, a light detector 120 may also detect light at times other than during the collection period. For example, the light detector 120 may detect light during the excitation period, or during a delay between a collection period and excitation period. The light detected during these times may be used, for example, to determine the intensity of the excitation light during the excitation period, determine the intensity of emissions between the excitation period and the collection period, etc. In another example, the light detector 120 may detect light during the entire cycle. A cycle includes an excitation period, a collection period and any delays between the periods. In this example, the DEDD 100 can use just the emissions data from the collection period(s) to analyze the sample.

A start sampling signal indicates the end of the excitation period or indicates that a delay has passed after the end of the excitation period. The start illumination signal may indicate the beginning of the first cycle, the end of a collection period, or the end of a delay after the end of a collection period. In embodiments, the light detector 120 may begin a collection period after receiving a start sampling signal and/or the illumination source 110 may start an excitation period after receiving a start illumination signal. In some cases, the illumination source 110 may communicate the start sampling signal to the light detector 120 and/or the light detector 120 may communicate the start illumination signal to the illumination source 110. In these cases, the illumination source 110 may be communicatively connected to the light detector 120. In other cases, the start sampling signal and/or start illumination signal may be sent from another source such as the processor 210. In one example, the processor 210 may send a start illumination signal to the illumination source 110 after a determination that the emissions 115 have decayed to a predefined level.

In embodiments, the light detector 120 may end the collection period after emissions 115 after receiving a stop sampling signal from the processor 210. In some cases, the stop sampling signal may be sent after the processor 210 makes the determination that the emissions have decayed to predefined level.

The delayed emission detection system 10 of FIG. 1 also includes a host computer 200 communicatively coupled to the light detector 120. The host computer 200 comprises a processor 210 communicatively coupled to a CRM 220 and a display 230. Alternatively, the host computer 200 can be a separate device from the delayed emission detection system 10. The host computer 200 can be any suitable computing device such as a smart-phone, tablet, etc.

In FIG. 1, the processor 210 (e.g., microprocessor) receives signal(s) with emissions data and from the light detector 120 associated with emissions 115 received by the light detector 120. In other embodiments, the signals from the light detector 120 may also include light data associated with other light received. The processor 210 can analyze the emissions data and other light data. In some cases, the processor 210 can generate fluorescence image data based on the emissions data received from the light detector 120. Fluorescence image data refers to any suitable data that can be used to generate a fluorescence image on the display 230 or other suitable output device. The fluorescence image may be of an object 150 (shown in FIG. 2) or tagged portion of an object 150 in the sample being examined by the DEDD 100.

The processor 210 executes code stored on the CRM 220 to perform some of the functions of delayed emission detection system 10 such as interpreting emissions data and other light data, performing analyses of the emissions data and other light data, generating fluorescence image data from the emissions data, determining whether the detected emissions have decayed to a predefined level, sending a start sampling signal to the light detector immediately after, or after a delay after the end of the excitation period, sending a stop sampling signal to the light detector 120 after it is determined that the detected emissions have decayed to a predefined level, sending a start illumination signal to the illumination source 110 to start the illumination period after it is determined that the detected emissions have decayed to a predefined level, etc.

The CRM (e.g., memory) 220 stores code for performing some functions of the delayed emission detection system 10. The code is executable by the processor 210. In embodiments, the CRM 220 may comprise: a) code for interpreting emission data and other light data received from the light detector 120, b) code for generating fluorescence image data of one or more objects 150 (as shown in FIG. 2) based on emissions data, c) code for sending a start sampling signal to the light detector 120 after the end of the excitation period or after a delay after the end of the excitation period, d) code for determining that the detected emissions have decayed to a predefined level, e) code for sending a stop sampling signal to the light detector 120 after it is determined that the detected emissions have decayed to a predefined level or after the end of a predetermined duration of the collection period, e) code for sending a start illumination signal to the illumination source 110 to start the illumination period after it is determined that the detected emissions have decayed to a predefined level or after a predetermined duration of the collection period, f) and/or any other suitable code for performing functions of the delayed emission detection system 10. The CRM 220 may also include code for performing any of the signal processing or other software-related functions that may be created by those of ordinary skill in the art. The code may be in any suitable programming language including C, C++, Pascal, etc.

The delayed emission detection system 10 also includes a display 230 communicatively coupled to the processor 210. Any suitable display may be used. In one embodiment, the display may be a part of the DEDD 100. The display 230 may provide analysis results (e.g., a fluorescence image of an object 150 in the sample) being examined to a user of the delayed emission detection system 10.

Modifications, additions, or omissions may be made to delayed emission detection system 10 without departing from the scope of the disclosure. In addition, the components of delayed emission detection system 10 may be integrated or separated according to particular needs. For example, the processor 210 or other suitable processor may be integrated into the light detector 120 so that the light detector 120 performs one or more of the functions of the processor 210 in some embodiments. As another example, the processor 210 and CRM 220 may be components of a computer (e.g., cloud computer) separate from the delayed emission detection system 10 and in communication with the delayed emission detection system 10. As another example, the DEDD 100 of some embodiments may include a stage or other container (e.g., fluid channel) for holding the sample or an object 150 in the sample while the object 150 is being examined by the DEDD 100.

II. Delayed Emission Detection Devices (DEDDs)

The DEDD 100 of the delayed emission detection system 10 can employ various scenarios of the delayed emission detection strategy to delay detecting emissions until after the excitation illumination is no longer present and/or detectable by the light detector 120. Three scenarios are described in this Section II. The three described scenarios, together with other emission detection techniques (such as described in those described in Section III), and other scenarios, can be employed individually or in combination in embodiments of the invention.

A. Scenario 1

In Scenario 1, the DEDD 100 includes a time-gated illumination source 110(a) providing time-gated excitation light 112(a) (e.g., pulsed light) to excite fluorophore(s) in the sample. The light detector 120 (detection unit) is synchronized with the time-gated excitation light 112(a) to measure emissions 115 at a later time, after the illumination source 110(a) stops providing excitation light 112(a). In this way, the light detector 120 avoids excitation light 112(a) and measures only emissions 115.

FIGS. 2(a) and 2(b) are schematic drawings of a cross-sectional view of components of a DEDD 100 employing Scenario 1 of the delayed detection strategy, according to an embodiment of the invention. FIG. 2(a) is a schematic drawing of components of the DEDD 100 at $t=t_0$, according to an embodiment of the invention. FIG. 2(b) is a schematic drawing of components of the DEDD 100 at $t=t_1$, according to an embodiment of the invention.

In FIGS. 2(a) and 2(b), the DEDD 100 includes a time-gated illumination source 110(a) providing time-gated excitation light 112(a) to a sample with an object 150 being examined by the DEDD 100. The DEDD 100 of FIGS. 2(a) and 2(b) also includes a light detector 120 receiving and detecting emissions 115 emitted from fluorophore(s) in the object 150. The light detector 120 includes a first surface 412. The DEDD 100 also includes an x-axis, a y-axis (not shown), and a z-axis. The x-axis and y-axis lie in the plane of the first surface 412. The z-axis is orthogonal to this plane.

FIGS. 2(a) and 2(b) illustrate an excitation strategy that synchronizes the light detector 120 with the excitation light 112(a) so that the light detector 120 avoids excitation light 112(a) and measures only emissions 115. In FIG. 2(a), the time-gated illumination source 110(a) starts to provide excitation light 112(a) at $t=t_0$ at the beginning of an excitation period. The excitation light 112(a) activates fluorophore(s) in the object 150 being examined by the DEDD 100. In FIG. 2(b), the time-gated illumination source 110(a) has stopped providing excitation light 112(a) at $t=t_1$ after the end of the excitation period. Due to the lifetime of the fluorescence/phosphorescence, the fluorophore(s) will continue to emit after the end of the excitation period. At $t=t_1$, the light detector 120 starts collecting (detecting) emissions 115 commencing a collection period. The light detector 120 captures emissions data during the collection period from $t=t_1$ to $t=t_2$. In some cases, when emissions 115 have been determined to have declined (i.e. decayed) to a predetermined level, the light detector 120 will stop collecting emissions 115 and the time-gated illumination source 110(a) will turn on again, for another excitation period which starts another cycle. The cycles continue until the capturing run is complete.

In FIGS. 2(a) and 2(b), the DEDD 100 includes a time-gated illumination source 110(a) (e.g., pulsed LED, pulsed laser, etc.) capable of providing time-gated excitation light 112(a) (e.g., pulses of excitation light 112(a)) to the sample with the object 150 during one or more excitation periods. The time-gated illumination source 110(a) may be placed in any suitable location and/or may include suitable components (e.g., reflective surfaces, lens, etc.) to direct excitation light 112(a) to the sample. Although FIGS. 2(a) and 2(b) show the time-gated illumination source 110(a) as a component of the DEDD 100, the time-gated illumination source 110(a) may be separate from the DEDD 100 in other embodiments. Although the illustrated example describes the illumination source 110 providing only excitation light 112(a), the illumination source 110 of other embodiments may provide other light or may provide excitation light 112(a) and other light to the sample.

The excitation light 112(a) in FIGS. 2(a) and 2(b) is time-gated (e.g., pulsed). The time-gated excitation light 112(a) may be any suitable type of light with any suitable properties (e.g., wavelengths, intensities, polarizations, phases, etc.) for activating fluorophore(s) in the object 150 to release emissions 115.

The time-gated illumination source 110(a) of FIGS. 2(a) and 2(b) can provide time-gated excitation light 112(a) during one or more excitation periods. In FIGS. 2(a) and 2(b), the time-gated illumination source 110(a) is shown providing time-gated excitation light 112(a) during an excitation period starting at $t=t_0$ and ending before $t=t_1$. The intensity profile of the time-gated excitation light 112(a) on the temporal domain may form a square wave in some cases. In other cases, the intensity profile on the temporal domain may have other forms.

The one or more excitation periods may have any suitable duration or durations. In many cases, a suitable duration of an excitation period may be determined based on the fluorophore used. In some of these cases, the duration of the excitation period can be in the range of femtosecond to nanosecond range ($10^{-12}$ to $10^{-9}$ second) in many cases. In other cases, the duration of the excitation period can be up to the millisecond range. In embodiments with multiple excitation periods, the excitation periods may have constant value durations in some cases or may have different values in other cases.

Any suitable object 150 or portion of an object 150 (e.g., cell nucleus) may be imaged or otherwise analyzed by the DEDD 100. Suitable objects 150 can be biological or inorganic entities. Examples of biological entities include whole cells, cell components, microorganisms such as bacteria or viruses, cell components such as proteins, etc. Inorganic entities may also be imaged by embodiments of the invention. Although many illustrated embodiments of the DEDD 100 are shown to be examining a single object 150, any number of objects 150 may be examined by embodiments of the DEDD 100.

In some cases, a reagent (e.g., dye) may be mixed with the sample having the object 150 before the sample is introduced into the DEDD 100. A reagent refers to any suitable chemical that can tag (mark) portions (e.g., molecules of a cell nucleus) of the object 150 to become fluorophores with suitable emission properties (e.g., lifetime).

In FIGS. 2(a) and 2(b), the time-gated configuration is applied to avoid the excitation light 112(a). In this illustrated example, the fluorescence/phosphorescence lifetime and other emissions properties (e.g., duration, intensity decay rate, etc.) can be crucial for the signal to noise ratio (SNR) of the DEDD 100. Usually, the lifetime of organic fluorophores can be about several nano-seconds. However, if a long life time dye (microsecond to millisecond) is applied, the SNR will be greatly improved.

As the time-gated illumination source 110(a) (light source) excites the object 150, in this case the whole cell, the light detector 120 may determine the spatial resolution of the system in some cases. Specifically, for a two-dimensional image sensor, the resolution may be the sensor's pixel size.

In FIGS. 2(a) and 2(b), the DEDD 100 includes a light detector 120. The light detector 120 in this illustrated example is synchronized with the time-gated illumination source 110(a) to receive only or primarily emissions 115, and avoid receiving excitation light 112(a). Thus, the light detector 120 in this example only or primarily receives emissions 115 and generates signal(s) with only or primarily emissions data.

The light detector 120 of FIGS. 2(a) and 2(b) includes one or more discrete light detecting elements 120(a) (as shown in FIG. 4(c)). Each light detecting element 120(a) can generate a signal with light data based on light received. The light detecting elements 120(a) can be arranged in any suitable form such as a single light detecting element 120(a) (e.g., a photo-diode (PD), an avalanche photo-diode (APD) and a photomultiplier tubes (PMT)), a one-dimensional or two-dimensional array of light detecting elements 120(a) (e.g., coupled device (CCD) array, a complementary metal-oxide-semiconductor (CMOS) array, an APD array, a PD array, a PMT array, etc.), or a multiplicity of one-dimensional and/or two-dimensional arrays of light detecting elements 120(a). The arrays can be in any suitable orientation or combination of orientations. Other suitable light detectors 120 are commercially available. Each light detecting element 120(a) may be of any suitable size (e.g., 1-10 microns) and any suitable shape (e.g., circular or square).

The light data may have any suitable information about the properties of the light received such as the intensity of the light, the wavelength(s) of the light, the frequency or frequencies of the light, the polarization(s) of the light, the phase(s) of the light, the spin angular momentum(s) of the light, and/or other light properties associated with the light detected by the light detector 120. Light data may also include the location of the light detecting element 120(a) receiving the light and generating a specific signal. The light data may also include the time that the light was detected by a particular light detecting element 120(a). Since the light detector 120 is synchronized with the illumination source 110(a) in FIG. 2, the light detecting elements 120(a) of the light detector 120 generate signals with light data that includes only or primarily emissions data.

The light detector 120 of FIGS. 2(a) and 2(b) can detect light at one or more sample times and captures snapshot light data at each sample time. The number of sample times may be determined by the duration of the collection period and a sampling rate of the light detector 120. Any suitable sampling rate may be used. In FIG. 2(b), the light detector 120 detects emissions during a sample time at $t=t_1$. The snapshot emissions data can be used to generate a snapshot fluorescent or phosphorescent image of the object 150 in the sample. In other embodiments, the light detector 120 may detect light on a time-varying basis and capture time-varying light data. The light detector 120 of these embodiments detects time-varying emissions and captures time-varying emissions data during the collection period.

In FIGS. 2(a) and 2(b), the light detector 120 can detect light during at least one collection period. The collection period occurs after the end of the excitation period and before any other excitation period begins. That is, the light detector 120 collects emissions 115 during a collection period after the excitation period during which the excitation light 112(a) is present. The light detector 120 and the illumination source 110 are synchronized so that the collection period is separate from the excitation period. That is, the collection period does not overlap with the excitation period. In some cases, the collection period starts after a suitable time delay after the end of an excitation period. A suitable time delay may be in the range of femtoseconds to nanoseconds. In other cases, the collection period may start immediately after the end of an excitation period without any delay.

The collection period may have any suitable duration. A suitable duration of the collection period may be in the range of microsecond to milliseconds in some cases. The duration may be predetermined in some cases before the capturing run. In other cases, the collection period may end after an event has occurred. For example, the collection period may end when it is determined that the detected emissions 115 have decayed to a predefined level. The predefined level may be any suitable level of one or more light properties. For example, the predefined level may be a percentage (e.g., 50%, 30%, 10%, etc.) of the maximum intensity detected by the light detector 120 during the analysis by the DEDD 100, the minimum intensity detectable by the light detector 120, a percentage (e.g., 50%, 30%, 10%, etc.) of the maximum intensity detectable by the light detector 120, an intensity value associated with the fluorescence dye in the sample, etc.

In one embodiment, a light detector 120 may also detect light at times other than during the collection period. For example, the light detector 120 may detect light during the excitation period, or during a delay between a collection period and excitation period. The light detected during these times may be used, for example, to determine the intensity of the excitation light during the excitation period, determine the intensity of emissions between the excitation period and the collection period, etc. In another example, the light detector 120 may detect light during the entire cycle. A cycle includes an excitation period, a collection period and any delays between the periods. In this example, the DEDD 100 can use just the emissions data from the collection period(s) to analyze the sample.

In FIGS. 2(a) and 2(b) and in FIGS. 5(a) and 5(b), the light detector 120 is synchronized with the time-gated illumination source 110(a) using a suitable excitation (synchronization) strategy. This synchronization is used to avoid excitation light 112(a) being received at the light detector 120 during the collection period(s) without using a filter. As a result, the light detector 120 of the illustrated embodiments only measures emissions 115 during collection period(s).

In one suitable excitation strategy, the time-gated illumination source 110(a) and the light detector 120 are synchronized so that the collection period occurs after the illumination period or after a delay after the illumination period. In this strategy, the light detector 120 is synchronized to start a collection period after the end of the excitation period. The time-gated illumination source 110(a) may also be synchronized to start another excitation period after the end of the collection period.

An example of one possible excitation (synchronization) strategy could be as follows. At $t=t_0$, the excitation light 112(a) excites the fluorophore(s) that tagged a region of the object 150 (e.g., cell). At $t=t_1$, the excitation source (e.g., time-gated illumination source 110(a)) stops, and due to the lifetime of the fluorescence, the fluorophore(s) will continue to emit. The light detector 120 (e.g., sensor) starts to collect the fluorescence signal (e.g., emissions 115). In some cases, when the fluorescence emission is almost finished, the excitation light source (e.g., time-gated illumination source 110(a)) will be turned on again, and another image can be captured.

In the excitation (synchronization) strategy illustrated in FIGS. 2(a) and 2(b), the first excitation period starts at $t=t_0$ and ends by the beginning of the collection period shown to start at $t=t_1$. In FIG. 2(b), the collection period is shown to start at $t=t_1$, after the end of the excitation period. The collection period ends before the start of any other excitation period. In this embodiment, the collection period does not overlap with an excitation period. Since the collection period starts at $t=t_1$, after the end of the excitation period and ends before a possible next excitation period, the light detector 120 of FIGS. 2(a) and 2(b) receives and measures only emissions 115 during the collection period. In some cases, there may be a suitable time delay between the collection period and the excitation period. A suitable time delay may be in the range of femtoseconds to nanoseconds, for example. In other cases, there is no delay.

Synchronization can be accomplished in any suitable way. In some cases, the time-gated illumination source 110(a) and the light detector 120 can be synchronized using signals sent to the components which trigger the turning on and off of functions of the components. For example, a start sampling signal can be sent to the light detector 120 that turns sampling on and/or a stop sampling signal can be sent to the light detector 120 that turns sampling off. As another example, a start illumination signal can be sent to the time-gated illumination source 110(a) to turn illumination on and/or a stop illumination signal can be sent to turn illumination off. In other cases, the time-gated illumination source 110(a) and the light detector 120 can be synchronized by initializing the light detector 120 after the time-gated illumination source 110(a) and then run the components at constant rates. For example, the time-gated illumination source 110(a) can be started at $t=t_0$ and run at a constant predefined rate of one pulse per second with an illumination period of 0.5 seconds. The light detector 120 can then be started at $t=0.5$ and run at a constant predefined rate of one collection period per second with a collection period of 0.5 seconds. The collection period will always occur after the illumination period. In yet other cases, the time-gated illumination source 110(a) and the light detector 120 can be synchronized using a combination of signals sent to the components and initializing the light detector 120 after the time-gated illumination source 110(a) and then running the components at constant rates.

In some cases, the light detector 120 may begin a collection period after receiving a start sampling signal. The start sampling signal indicates the end of the excitation period or indicates that a delay has passed after the end of the excitation period. In some cases, the illumination source 110 may communicate the start sampling signal to the light detector 120. In these cases, the illumination source 110 may be communicatively connected to the light detector 120. In other cases, the processor 210 may send the start sampling signal. In other embodiments, the light detector 120 may begin the collection period based on a predefined rate (e.g., pulse rate) of the time-gated illumination source 110(a).

In some cases, the light detector 120 may end the collection period after receiving a stop sampling signal from the processor 210. In some cases, the stop sampling signal may be sent after the processor 210 makes the determination that the emissions have decayed to predefined level. In other cases, the stop sampling signal may be sent after a predetermined duration of the collection period has elapsed.

In some cases, the illumination source 110 may start an excitation period after receiving a start illumination signal. The start illumination signal may indicate the beginning of the first cycle, the end of a collection period, or the end of a delay after the end of a collection period. In one case, the light detector 120 may communicate the start illumination signal to the illumination source 110. In this case, the illumination source 110 may be communicatively connected to the light detector 120. In another case, the start illumination signal may be sent from another source such as the processor 210. For example, the processor 210 may send a start illumination signal to the illumination source 110 after a determination that the emissions 115 have decayed to a predefined level.

Modifications, additions, or omissions may be made to DEDD 100 of Scenario 1 and other Scenarios without departing from the scope of the disclosure. In addition, the components of DEDD 100 may be integrated or separated according to particular needs. For example, the processor 210 or other suitable processor may be integrated into the light detector 120 so that the light detector 120 performs one or more of the functions of the processor 210 in some embodiments. As another example, the DEDD 100 of some embodiments may include a stage or other container (e.g., fluid channel) for holding the sample or an object 150 in the sample while the object 150 is being examined by the DEDD 100.

1. Method of Using DEDD Employing Scenario 1

Figure 3:
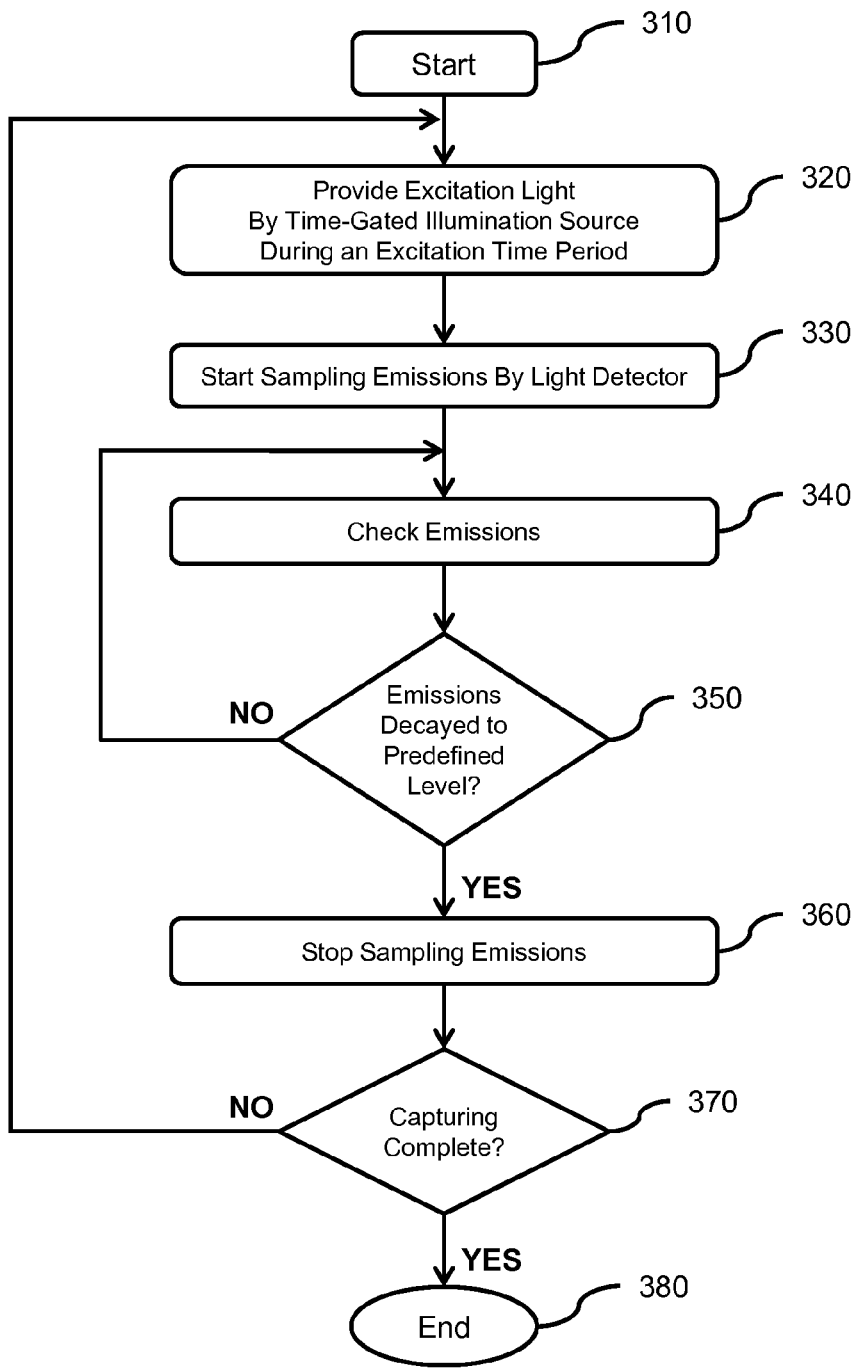
FIG. 3 is a flowchart of a method of using the DEDD to detect emissions based on Scenario 1, according to embodiments of the invention.

FIG. 3 is a flowchart of a method of using the DEDD 100 to detect emissions based on Scenario 1, according to embodiments of the invention. The method starts at step 310. In some cases, a reagent (e.g., dye) may be mixed with the sample having the object 150 being examined. The reagent tags portion(s) (e.g., nucleus) of the object 150 (e.g., cell) with fluorophores. The resulting sample with fluorophores may be introduced to the DEDD 100 at this step.

At step 320, a time-gated illumination source 110(a) provides excitation light 112(a) to a sample having an object 150 being examined by a DEDD 100. The fluorophores in the object 150 absorb excitation light 112(a) and release emissions 115 of fluorescent/phosphorescent light. The excitation light 112(a) is provided during an excitation period of a suitable predetermined duration. The duration may be determined based on the fluorophore. For example, a suitable predetermined duration may be the amount of time that is determined to provide sufficient energy to a fluorophore to generate emissions 115 at a minimum intensity level at a time during the collection period. In some embodiments, a suitable duration may be in the range of femtoseconds to milliseconds.

After the end of the excitation period or after a delay after the end of the excitation period, the time-gated illumination source 110(a) or the processor 210 sends a start sampling signal to the light detector 120. At step 330, the light detector 120 starts sampling emissions 115 and the collection period begins. In this example, the light detector 120 starts sampling emissions at one or more sample times to capture snapshot emission data at each sample time. The snapshot emission data taken at each sample time can be used to generate a snapshot fluorescent/phosphorescent image of the object 150. The number of sample times can be determined based on the duration of the collection period and the sampling rate of the light detector 120. Any suitable sampling rate may be used. In another embodiment, the light detector 120 detects emissions 115 on a time-varying basis and captures time-varying emissions 115 during the collection period.

In another embodiment, the light detector 120 may start sampling at a predetermined time instead of being based on a start sampling signal. For example, the time-gated illumination source 110(a) may be programmed with an excitation period of a constant duration and a constant rate (e.g. one excitation period per second). The light detector may be programmed to start sampling after the excitation period has elapsed.

At step 340, the emissions data taken at a sample time is checked to determine if emissions 115 have decayed to a predefined level. In this example, the duration of the collection period is determined by the time it takes the emissions 115 to have decayed to a predefined level. The predefined level may be any suitable level of one or more light properties. For example, the predefined level may be a percentage (e.g., 50%, 30%, 10%, etc.) of the maximum intensity detected by the light detector 120 during the analysis by the DEDD 100, the minimum intensity detectable by the light detector 120, a percentage (e.g., 50%, 30%, 10%, etc.) of the maximum intensity detectable by the light detector 120, an intensity value associated with the fluorescence dye in the sample, etc. In some cases, a signal with the emissions data is sent to a separate processor 210 to make the determination of whether the predefined level has been reached. In other cases, the light detector 120 has a processor 210 that makes the determination. The emissions 115 may be checked at every sample time or may be checked periodically.

If the emissions 115 have not decayed to the predefined level at step 350, then the light detector 120 continues measuring emissions 115. Then, another set of emissions data at a later sample time is checked at step 340 to determine if the emissions 115 have decayed to a predefined level. If however, the emissions 115 have decayed to a predefined level at step 350, then the light detector 120 stops sampling emissions 115 at step 360 and the collection period ends.

In another embodiment, the collection period may have a predetermined duration. In this embodiment, the light detector 120 samples emissions 115 at step 330 during the predetermined duration and then stops sampling without checking the emissions, and continues to step 370 to determine whether the capturing run is complete.

At step 370, the processor 210 determines whether capturing by the DEDD 100 is complete. If it is determined that capturing is not complete, the processor 210 sends a start illumination signal to the time-gated illumination source 110(a) to start the next excitation period and another cycle starts at step 320. If the capturing run is complete, the method ends at step 380.

B. Optofluidic DEDDs

An optofluidic DEDD 100 is a DEDD 100 that incorporates elements of optofluidic microscopy (e.g., fluid channel, aperture array, etc.). An optofluidic DEDD 100 is an example of an optofluidic emission detection device, which refers to a device that detects fluorescence and/or phosphorescence emissions 115 and incorporates elements of optofluidic microscopy. Another example of an optofluidic emission detection device is a fluorescence Optofluidic Microscope (fluorescence OFM) discussed below.

Two optofluidic DEDDs 100 of embodiments will be described in this Section. The first optofluidic DEDD 100 uses Scenario 2 of a delayed detection strategy. The second optofluidic DEDD 100 uses Scenario 3 of the delayed detection strategy. The optofluidic DEDDs 100 of embodiments can use any of the modes of illumination discussed in the Section below.

1. Fluorescence OFMs

Optofluidic microscopy is a high-resolution and low-cost, chip-level microscopy technique. Some examples of OFM devices can be found in Heng, X., Erickson, D., Baugh, L. R., Yaqoob, Z. Sternberg, P. W., Psaltsis, D, and Yang, C., "Optofluidic microscopy: a method for implementing high resolution optical microscope on a chip," Lab on a Chip 6, 1274 (2006), Heng, X., Hsiao, E., Psaltis, D., and Yang, C., "An optical tweezer actuated, nanoaperture-grid based optofluidic microscope implementation," Optics Express 15, 16367 (2007), Cui, X., Lee, L. M., Heng, X., Zhong, W., Sternberg, P. W., Psaltis, D., and Yang, C., "Lensless high-resolution on-chip optofluidic microscopes for *Caenorhabditis elegans* and cell imaging," Proceedings of the National Academy of Science 105, 10670 (2008), Wu, J., Cui, X., Lee, L. M., and Yang, C., "The application of Fresnel zone plate based projection in optofluidic microscopy," Optics Express 16, 15595 (2008), and Lee, L. M., Cui, X., and Yang, C., "The application of on-chip optofluidic microscopy for imaging Giadia lamblia trophozoites and Cysts," Biomed Microdevices DOI 10.1007/s10544-009-9312-x (2009), which are hereby incorporated by reference in their entirety for all purposes. Combined with appropriate high-flow velocity microfluidic techniques, OFM devices can be used in many biomedical applications, such as image-based cytometry, blood parasite diagnosis and water quality inspection. Combining fluorescence techniques in an OFM device can utilize the advantages of the two techniques and may have promising applications in the biomedical area.

Illumination Mode 113 Aperture Array Passing Light to Light Detector

The basic idea of previous OFM devices, as illustrated in FIG. 4(a), is to use an aperture array to scan a sample with an object being imaged as the sample flows through a fluid channel. The transmission of illumination light through the apertures will be changed as the object moves through the fluid channel and disturbs the light field. The object image can then be reconstructed by measuring light transmission time traces of the apertures. In this case, the resolution of the OFM is limited by the size of the aperture instead of by the pixel size of the light detector, which is usually larger due to fabrication limitations. An example of a similar scheme can be found in U.S. patent application Ser. No. 12/398,050, entitled "Optofluidic Microscope Device with Photosensor Array," filed on Mar. 4, 2009, which is hereby incorporated by reference in its entirety for all purposes.

FIG. 4(a) is a schematic drawing of a perspective view of components of an OFM device 400, according to embodiments of the invention. The OFM device 400 includes a multi-layered body 401 defining or including a fluid channel 410 having a fluid flow with an object 150 being imaged. The fluid channel 410 has a first surface 412 and a second surface 414 on opposing sides of the fluid channel 410. The fluid channel 410 also has a third surface 416 and fourth surface 418 on opposing lateral sides of the fluid channel 410. The body 401 also includes an opaque or semi-opaque aperture layer 420 (e.g. thin metallic layer) including the first surface 412 and a light detector layer 430 outside the aperture layer 420. The aperture layer 420 has light transmissive regions 422(a) (e.g., apertures) in it. The light detector layer 430 includes a light detector 120. The light detector 120 comprises discrete light detecting elements 120(a) in the form of a one-dimensional array of light detecting elements 120(a), a two-dimensional array of light detecting elements 120(a) or multiple arrays (one-dimensional and/or two-dimensional) of light detecting elements 120(a). The OFM device 400 also includes an x-axis, a y-axis, and a z-axis. The x-axis and y-axis lie in the plane of the first surface 412 of the aperture layer 420. The z-axis is orthogonal to this plane.

In FIG. 4(a), the light transmissive regions 422(a) are in the form of a one-dimensional array of light transmissive regions 422(a) diagonally extending from one lateral side 416 to another lateral side 418 of the fluid channel 410. In other embodiments, the light transmissive regions 422(a) may be in other forms such as a two-dimensional array of light transmissive regions 422(a) or multiple arrays (one-dimensional and/or two-dimensional) of light transmissive regions 422(a).

In yet other embodiments, the light transmissive regions 422(a) may be in the form of one or more slits. These light transmissive regions 422(a) may be arranged in any suitable orientation.

During operation, light 112 from an illumination source 110 is provided to the fluid channel 410. As the fluid sample flows through the fluid channel 410, the object 150 alters (blocks, reduces intensity, modifies wavelength or other light property or spatial distribution) the light in the fluid channel 410. The altered light and unaltered light (i.e. light that does not interact with the object 150) passes through the light transmissive regions 422(a). The light detecting elements 120(a) receive the light and generate time varying light data about the light as the object 150 moves through the fluid channel 410. A processor 210 (not shown) receives a signal with time varying light data. The processor 210 uses the time varying light data to generate line scans associated with the y-locations of the light transmissive regions 422. The time varying light data from the light detecting elements 140(a) is dependent on the profile of the object 150 as well as its optical properties. The processor 210 can reconstruct an image of the object 150 by appropriately shifting and assembling the line scans, and optionally other data such as rotation, velocity of the object 150, and changes in shape of the object 150, etc.

Illumination Mode 2—Aperture Array Acting as Illumination Source

An illumination mode OFM is also possible with an aperture array 422 acting as illumination source, as shown in FIG. 4(b). It is possible to implement a simple fluorescence OFM system, as described below, with this type of illumination mode OFM by adding a filter 450 in the system. In this case, the aperture array 422 illuminates the sample and locally excites the fluorophore(s). The fluid channel 410 is attached to the imaging sensor (e.g., light detector 120). The top floor of the imaging channel can be coated with a layer of material 420 (e.g., thin metallic layer) having an aperture array 420. Light can only pass through the aperture array 420 in the layer of material 420. A filter 450 can be inserted in between the fluidic channel 410 and the sensor (e.g., light detector 120) to reject the scattered excitation light 112. The excitation light 112 illuminates the sample from the top and the light detector 120 and filters are underneath the fluid channel 410.

FIG. 4(b) is a schematic drawing of a side view of components of an OFM 400 for fluorescence/phosphorescence imaging (i.e. a fluorescence OFM) using an aperture array as an illumination source, according to embodiments of the invention. The OFM 400 of FIG. 4(b) includes a multi-layered body 401, which defines or includes the fluid channel 410 having a fluid flow with an object 150 being imaged. The fluid channel 410 has a first surface 412 and a second surface 414 on opposing sides of the fluid channel 410. The fluid channel 410 also includes an inlet 410(a) and an outlet 410(b) connected to portions, typically opposite ends, of the fluid channel 410. An inlet 410(a) can refer to a port where the fluid sample can be introduced into the fluid channel 410. An outlet 410(b) can refer to a port where the fluid specimen can exit the fluid channel 410. In the illustrated example, the fluid channel 410 is U-shaped having three straight portions.

The body 401 also includes an opaque or semi-opaque aperture layer 420 (e.g. thin metallic layer) that is an inner surface layer of the fluid channel 410 and includes the second surface 414. The aperture layer 420 has light transmissive regions 422(a) (e.g., apertures) in it. The light transmissive regions 422(a) may be in the form of a one-dimensional array of light transmissive regions 422(a), a two-dimensional array of light transmissive regions 422(a) or multiple arrays (one-dimensional and/or two-dimensional) of light transmissive regions 422(a). The array(s) may be in any suitable orientation. In one case, the array(s) may diagonally extend across the fluid channel 410.

The body 401 also includes a transparent layer 440 to the outside of the aperture layer 420. A protective transparent layer (not shown) may lie to the inside of the aperture layer 420 in some cases. The body 401 also includes a filter 450 on an inside surface layer of the fluid channel 410 having the first surface 412. The filter 450 can allow emissions 115 to pass and reflects/absorbs other light. The body 401 also includes a light detector layer 430 located to the outside of the filter 450. The light detector layer 430 includes a light detector 120. The body 401 may include an additional filter (not shown) located between the aperture layer 420 and the transparent layer 440 to pass excitation light 112 and absorb/reflect other light. The light detector 120 comprises light detecting elements 120(a) in the form of a one-dimensional array of light detecting elements 120(a), a two-dimensional array of light detecting elements 120(a) or multiple arrays (one-dimensional and/or two-dimensional) of light detecting elements 120(a).

As fluid flows with the object 150 through the fluid channel 410, the illumination source (not shown) provides excitation light 112 which passes through the transparent layer 440. The excitation light 112 passes through the light transmissive regions 422(a) to illuminate the first surface 412 and the surface of the object 150. As the fluid flows, the object 150 passes under light transmissive regions 422(a) projecting excitation light 112 which excite the fluorophores in portions of the object 150 and blocks some light. A filter 450 allows emissions 115 (i.e. light re-emitted from the fluorophores) to pass through to the light detector 120 and reflects/absorbs all other light received by the first surface 412. The light detecting elements 120(a) take time varying data of the intensity of the emissions 115. The data is then used to generate fluorescence images of the object 150 and portions of the object 150 tagged with fluorophores.

An example of a similar fluorescence OFM device can be found in U.S. patent application Ser. No. 12/398,050, entitled "Optofluidic Microscope with Photosensor Array," filed on Mar. 4, 2009, which is hereby incorporated by reference in its entirety for all purposes.

Illumination Mode 3—Focused Beam Array Illumination

Equivalently, another way to implement optofluidic microscopy is to use an array of focused light beams in place of the aperture array, as shown in FIG. 4(c). The transmission of each focusing beam is measured and used to reconstruct the OFM image as the sample flows through the microfluidic channel. In this case, the resolution is limited by the focus size. The advantages of this configuration are: (1) simpler fabrication process; (2) the position of focusing array can be easily adjusted according to sample position, avoiding decrease of resolution because of the beam divergence; (3) the existence of a focusing beam can be used for fluorescence excitation.

FIG. 4(c) is a schematic drawing of a perspective view of components of an OFM device 400 using focused beam array illumination, according to embodiments of the invention. The OFM device 400 includes a multi-layered body 401, which defines or includes the fluid channel (not shown) 410 having a fluid flow with an object 150 being imaged. The OFM 400 also includes a light detector 120 comprising a two-dimensional array of light detecting elements 120(a). In other embodiments, the light detector 120 may be in other forms such as a one-dimensional array of light detecting elements 120(a) or multiple arrays (one-dimensional and/or two-dimensional) of light detecting elements 120(a).

Figure 4:
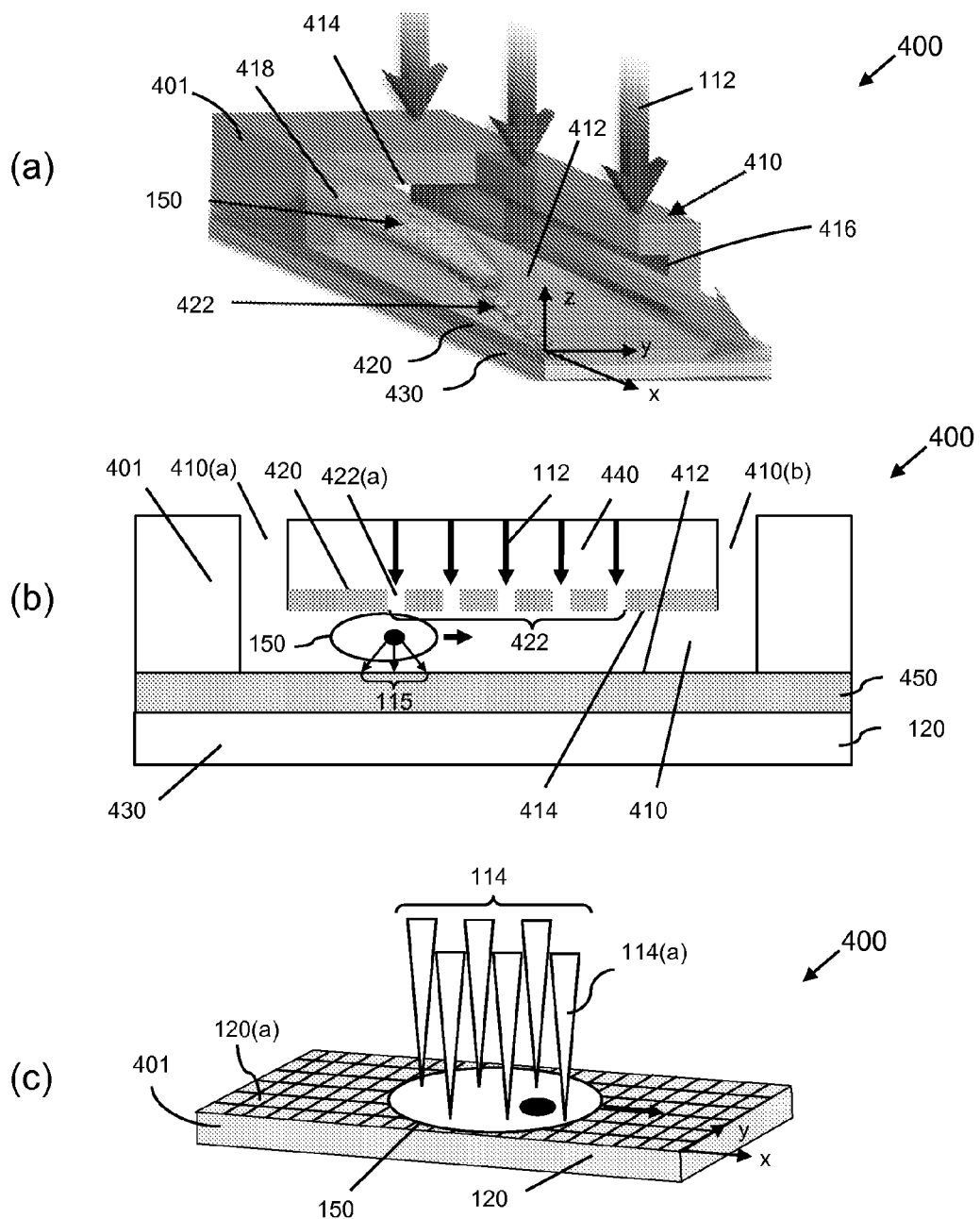
FIG. 4(a) is a schematic drawing of a perspective view of components of an OFM device, according to embodiments of the invention.
FIG. 4(b) is a schematic drawing of a side view of components of an OFM for fluorescence/phosphorescence imaging (i.e. a fluorescence OFM) using an aperture array as an illumination source, according to embodiments of the invention.
FIG. 4(c) is a schematic drawing of a perspective view of components of an OFM device using focused beam array illumination, according to embodiments of the invention.

In embodiments using focused beam array illumination, a focused beam array generator is an illumination source 110 that can generate a focused beam array 114 of excitation light 112. In FIG. 4(*c*), the focused beam array 114 includes six (6) focused beams 114(*a*). A focused beam 114(*a*) can refer to any suitable focused beam of excitation light 112. In another embodiment, an OFM device 400 may include a Bessel beam generator that may generate an array of Bessel beams using a similar illumination principle as described in FIG. 4(*c*).

In focused beam array illumination embodiments, the focused light beams 114(*a*) can be in any form, such as a one-dimensional array, a two-dimensional array, or multiple arrays (one-dimensional and/or two-dimensional) of focused light beams 114(*a*). In FIG. 4(*a*), the focused beams 114(*a*) are in the form of a two-dimensional array having a 2×3 dimension. The array(s) may be in a suitable orientation(s). In FIG. 4(*c*), the array extends diagonally across the fluid channel 410. Each focused light beam 114(*a*) at a particular x, y location can correspond to a set of one or more unique light detecting elements 120(*a*) on the light detector 120.

As fluid flows with the object 150 through the fluid channel, the object 150 passes under the focused light beams 114(*a*) of excitation light 112, which excites the fluorophores in portions of the object 150 and blocks some light. A filter may be placed over the light detector 120 to allow emissions 115 (i.e. light re-emitted from the fluorophores) to pass through to the light detector 120 and reflect/absorb substantially all other light received by the first surface 412. In other embodiments, a delayed emission detection strategy of Scenario 2 or 3 can be used to avoid excitation light without using a filter. Having removed or avoided the excitation light 112, the light detecting elements 120(*a*) receive primarily or only emissions 115 and can take time varying emissions data of the intensity of the emissions 115. A processor 210 (as shown in FIG. 1) can use the time varying emissions data associated with each focused beam 114(*a*) to generate line scans associated with the y-locations of the associated focused light beam 114(*a*). The processor 210 can reconstruct from the line scans a fluorescence image of the object 150 and portions of the object 150 tagged with fluorophores.

Optofluidic Emission Detection Device (E.G., Optofluidic DEDD) Components

An optofluidic emission detection device (e.g., an optofluidic DEDD) of embodiments comprises the following components:

(a) The Fluid (E.G., Microfluidic) Channel

The shape of the channel can be straight or curved, and the flow may be driven by electromagnetic force, gas/liquid pressure, or gravity. The material can be fused silica (glass), Polydimethylsiloxane (PDMS) or other polymer, or any other suitable material.

(b) The Illumination (Light) Source

The illumination source can be thermal sources, LED, continuous-wave laser, or pulsed laser, ambient light, or other suitable source to excite/illuminate the sample.

(c) The Light Detector (E.G., Imaging Sensor)

The light detector can be CCD, CMOS, or PMT/APD array or other suitable detector capable of collecting the fluorescence signal. The object 150 (e.g., cell) flows inside the channel on top of the imaging sensor.

(d) The Aperture Array Mask for Local Illumination

The aperture array mask is opaque or semi-opaque with one dimensional or two dimensional aperture arrays. It can be a separate layer, or it also can be the top floor of the channel coated with a layer of metal (Au, Al, Ag, etc.) about 300 nm to 500 nm thick.

The fluid channel 410 has a suitable shape (e.g., straight, curved, U-shaped, S-shaped, substantially circular, etc.) along its length. In non-linear shaped fluid channels 410, the fluid channel 410 can be comprised of a series of straight portions and/or curved portions. For example, the fluid channel 410 may be U-shaped with two curved portions in the corners and three straight portions at the edges and in between curved portions. The fluid channel 410 can have any cross-sectional shape (e.g., rectangular, circular, etc.) of suitable dimensions. For example, in some applications, the width and/or height of the fluid channel 112 may be about 10 microns, 5 microns, or 1 micron. The fluid channel 410 can be any suitable material, for example, fused silica (glass), Polydimethylsiloxane (PDMS) or other polymers.

The flow in the fluid channel 410 may be driven by electromagnetic force, gas/liquid pressure, or gravity. Any suitable technique of controlling fluid flow and/or particulate transport can be used to move an object 150 through the fluid channel 410. Some conventional techniques include pressure drive flow, electrokinetic transport, discrete droplet translocation via electrowetting, or thermocapilarity techniques. Other techniques may include gravity drive flow, hydrodynamic focusing, dielectrophoresis, and optical tweezing. Any suitable control device(s) may be used to control the flow of fluid and/or movement of the object 150 through the fluid channel 410. Some examples of suitable control devices include micropumps, direct current (DC) electrokinetic devices, dielectrophoresis electrodes, and/or hydrodynamic focusing channels.

The illumination source 110 can include, for example, a thermal source, an LED, a continuous-wave laser, or a pulsed laser, to excite/illuminate the sample. Excitation light 112 may have any suitable light property or properties (e.g., wavelengths, intensities, polarizations, phases, etc.) for suitably activating fluorophore(s) in the sample to cause the release of emissions 115. The illumination source 110 can use any of the above modes of illumination used in OFM devices, discussed in the above-section.

In many embodiments, the light detector 120 includes one or more discrete light detecting elements 120(*a*) (as shown in FIG. 4(*c*)). The one or more light detecting elements 120(*a*) can be arranged in any suitable form such as a single light detecting element 120(*a*), a one-dimensional array of light detecting elements 120(*a*), a two-dimensional array of light detecting elements 120(*a*), or a multiplicity of one-dimensional and/or two-dimensional arrays of light detecting elements 120(*a*). The arrays can be in any suitable orientation or combination of orientations. Some examples of light detectors having a single light detecting element 120(*a*) include a photo-diode (PD), an avalanche photo-diode (APD) and a photomultiplier tubes (PMT). Some examples of light detectors 120 having one-dimensional or two-dimensional arrays include a charge coupled device (CCD) array, a complementary metal-oxide-semiconductor (CMOS) array, an APD array, a PD array, a PMT array, etc. Other suitable light detectors 120 are commercially available. Each light detecting element 120(*a*) may be of any suitable size (e.g., 1-10 microns) and any suitable shape (e.g., circular or square). For example, a complementary metal-oxide-semiconductor (CMOS) or charge coupled device (CCD) light detecting element 120(*a*) may be 1-10 microns and an APD or PMT light detecting element 120(*a*) may be as large as 1-4 mm.

The aperture array mask is an opaque or semi-opaque aperture layer 420 of material. It can be a separate layer, or can be can be a coating on the inside surface of the fluid channel 410. The coating can be a layer of metal (e.g., Au, Al, Ag, etc.) of suitable thickness. For example, the thickness can be about 300 nm to 500 nm thick in some cases.

The aperture layer 420 has light transmissive regions 422(a) (e.g., apertures) in it. The light transmissive regions 422(a) may be in the form of a one-dimensional array of light transmissive regions 422(a), a two-dimensional array of light transmissive regions 422(a) or multiple arrays (one-dimensional and/or two-dimensional) of light transmissive regions 422(a). In one example, the light transmissive regions 422(a) are in the form of a one-dimensional array diagonally extending across the fluid channel 410.

The optofluidic emission detection device can also have one or more filters that allow light of certain wavelengths to pass and reflect (or absorb) light of other wavelengths. In one exemplary embodiment, a first filter 450 (as shown in FIG. 4(c)) is an optical color filter (e.g., a blue filter) that allows light of a narrow range of wavelengths associated with a color (e.g., blue) that is associated with exciting the fluorophores in the object 150 and filters out other wavelengths. In this example, the illumination source 110 may emit a broad spectrum of light and this filter allows only the light that excites the fluorophores (e.g. blue light) to pass. The fluorophores may re-emit a light of a certain wavelength(s) (e.g., green light) in response. A second filter may be an optical filter (e.g., a green filter) that allows the light being re-emitted from the fluorophores to pass and filters out other wavelengths of light. More of fewer filters can be used in other embodiments. For example, the first filter can be omitted if the light provided by illumination source 110 is only excitation light 112.

In other embodiments, an optofluidic DEDD 100 employing Scenario 2 or 3 can be used to avoid excitation light 112 without using a filter. Examples of optofluidic DEDDs 100 employing Scenario 2 and 3 are discussed in Section IIB(2) and IIB(3) below.

2. Scenario 2

Like the DEDD 100 employing Scenario 1, the optofluidic DEDD 100 employing Scenario 2 includes a time-gated illumination source 110(a) providing time-gated excitation light 112(a) (e.g., pulsed light). In Scenario 2, however, the excitation light 112(a) is projected through an aperture array into a fluid channel 410 having a fluid flow carrying an object 150 being examined. A light detector 120 is synchronized with the time-gated excitation light 112(a) to measure emissions 115 from excited fluorophore(s) at a later time after the illumination source 110(a) stops providing excitation light 112(a).

The illumination setup in Scenario 2 is similar to the setup shown in FIG. 4(b). Just as shown in FIG. 4(b), the excitation light 112(a) is localized by an aperture array 422. The aperture array 422 has one or more light transmissive regions 422(a) (e.g., apertures). In some cases, the size of the light transmissive regions 422(a) could be similar or a little less than the wavelength.

Like Scenario 1, the rejection of excitation light 112(a) also relies on the time-gated strategy. Only a small area below the light transmissive region 422(a) is exposed to the excitation, so the resolution of a DEDD 100 may be determined by the size of the light transmissive region 422(a) in some embodiments. The size of the light transmissive region 422(a) may be smaller than the size of the light detector element 122(a) in some cases. For the same reason, instead of only one light detecting element 120(a) (e.g., pixel), the large area of the light detector 120 (e.g., imaging sensor) under the light transmissive region 422(a) collects the fluorescence emissions 115. A larger collection area can improve collection of the relatively weak emissions 115, which can decrease exposure time and thus increase imaging speed.

In some cases, the light transmissive regions 422(a) can be fabricated to be much less than a wavelength and can be used as a waveguide working in cutoff mode. When an object (e.g., cell) 150 flows under the light transmissive region 422(a), it will perturb the evanescent field and the excitation light 112(a) will be coupled into the object 150 and induce fluorescence.

FIGS. 5(a) and 5(b) are schematic drawings of a side view of components of an optofluidic DEDD 100 employing Scenario 2 of the delayed detection strategy, according to an embodiment of the invention. FIG. 5(a) is a schematic drawing of components of the optofluidic DEDD 100 at $t=t_0$ and FIG. 5(b) is a schematic drawing of the components of the optofluidic DEDD 100 at $t=t_1$.

The optofluidic DEDD 100 of FIGS. 5(a) and 5(b) includes a multi-layered body 401, which defines or includes the fluid channel 410. The fluid channel 410 has a first inner surface 412 and a second inner surface 414 on opposing sides of the fluid channel 410. Although not shown, the fluid channel 410 has a third inner surface 416 and a fourth inner surface 418 on opposing lateral sides of the fluid channel 410. The body 401 also includes an opaque or semi-opaque aperture layer 420 (e.g. thin metallic layer) that is an inner surface layer of the fluid channel 410 and includes the second surface 414. The aperture layer 420 has an aperture array 422 in it. The aperture array 422 includes one or more light transmissive regions 422(a). The body 401 also includes a light detector layer 430 including the light detector 120. Although not shown, the light detector 120 includes discrete light detecting elements 120(a). A protective transparent layer (not shown) may lie to the inside of the aperture layer 420 in some cases.

In FIGS. 5(a) and 5(b), the optofluidic DEDD 100 also includes a time-gated illumination source 110(a) providing time-gated excitation light 112(a) to a sample with an object 150 being examined by the optofluidic DEDD 100. Although the time-gated illumination source 110(a) is shown as a component of the optofluidic DEDD 100 in the illustrated example, the time-gated illumination source 110(a) may be a separate component in other embodiments.

In FIGS. 5(a) and 5(b), the optofluidic DEDD 100 also includes a light detector 120. The light detector 120 is synchronized with the time-gated excitation light 112(a) to receive and measure only or primarily emissions 115 released from fluorophore(s) in the object 150. The optofluidic DEDD 100 also includes an x-axis, a y-axis (not shown), and a z-axis. The x-axis and y-axis lie in the plane of the first surface 412 of the aperture layer 420. The z-axis is orthogonal to this plane.

FIGS. 5(a) and 5(b) illustrate the synchronized operation of the optofluidic DEDD 100 during a cycle of a multi-cycle capturing run as an object 150 moves in a fluid flow through the fluid channel 410. In FIG. 5(a), the time-gated illumination source 110(a) starts to provide excitation light 112(a) at $t=t_0$ at the beginning of an excitation period. The excitation light 112(a) is projected through the aperture array 422, which localizes the excitation light 112(a) in the fluid channel 410. The localized excitation light 112(a) illuminates the first surface 412 and the object 150. As the fluid flows, the object 150 passes under the aperture array 422, the localized excitation light 112(a) excites the fluorophores in portions of the object 150 and blocks some light. In FIG. 5(b), the time-gated illumination source 110(a) has stopped providing excitation light 112(a) at $t=t_1$ after the end of the excitation period. Due to the lifetime of the fluorescence or phosphorescence, the fluorophore(s) will still emit after the end of the excitation period. At $t=t_1$, the light detector 120 starts collecting emissions 115 commencing a collection period. The light detector 120 collects emissions data during the collection period starting at $t=t_1$. In some cases, the time-gated illumination source 110(a) may start to provide excitation light 112(a) at the beginning of another excitation period at a time after the end of the collection period. The cycling through excitation period followed by collection period continues as the object 150 moves through the fluid channel 410 until the capturing run is complete. As the object 150 moves in the fluid flow through the fluid channel 410, the light detecting elements 120(a) take time-varying emissions data (e.g., line scans) of the intensity (and/or other properties) of the emissions 115 during the collection periods. The time varying emissions data can be used to generate line scans associated with the y-locations of the light transmissive regions 422(a). The time varying emissions data can then be used to reconstruct fluorescence/phosphorescence images of the portions of the object 150 tagged with fluorophores or otherwise analyze the object 150. The images are reconstructed by appropriately shifting and assembling the line scans, and optionally other data such as rotation, velocity of the object 150, and changes in shape of the object 150, etc.

The layers of the multi-layer body 401 may be made of any suitable material (e.g., fused silica (glass), Polydimethylsiloxane (PDMS) or other polymer) or combination of materials of any suitable thickness or thicknesses, and may include suitable device(s) (e.g., light detector 120). In one exemplary embodiment, the multi-layer body 401 consists of a micromolded PDMS microfluidic chip bonded directly to a CMOS sensor. In some cases, the multi-layer body 401 may be fabricated using standard semiconductor and micro/nanofabrication procedures. Although the illustrated example shows certain layers in the multi-layer body 401, other embodiments may integrate, omit, or add one or more layers or change the location of one or more layers in the multi-layer body 401. Also, other embodiments may have a monolithic body 401.

In FIGS. 5(a) and 5(b), the fluid channel 410 includes a first surface 412 and an opposing second surface 414. Although not shown, the fluid channel 410 also includes lateral surfaces including a third surface 416 and an opposing fourth surface 418. The fluid channel 410 also has a longitudinal axis along the x-axis. Although a single fluid channel 410 is shown in FIGS. 5(a) and 5(b), other embodiments may include additional fluid channels 410 for parallel processing. Although not shown, the fluid channel 410 may also includes an inlet 410(a) and an outlet 410(b) as shown in FIG. 4(b).

The dimensions of the fluid channel 410 in FIGS. 5(a) and 5(b) may be of any suitable size. For example, the width and/or height of the fluid channel 410 may each be less than about 10 microns, 5 microns, or 1 micron. In some embodiments, the dimensions (geometry) of the fluid channel 410 are sized to improve or maximize image quality. For example, the channel height may be sized based on the size of the object 150 being imaged to flow the object 150 close to the first surface 412, which may improve image quality.

The fluid channel 410 can have any suitable shape (e.g., linear, U-shaped, S-shaped, substantially circular shaped, etc.). An example of a U-shaped fluid channel 410 can be found in FIG. 4(b). In non-linear shaped fluid channels 410, the fluid channel 410 can be comprised of a series of straight portions and/or curved portions.

The fluid channel 410 may include a fluid flow that carries a fluid sample with one or more objects 150 being imaged or otherwise analyzed through the fluid channel 410 in the general direction of the longitudinal axis of the fluid channel 410. Any suitable technique of controlling fluid flow and/or particulate transport can be used to move the object(s) 150 through the fluid channel 410. Some convention techniques include pressure drive flow, electrokinetic transport, discrete droplet translocation via electrowetting, or thermocapilarity techniques. Other techniques may include gravity drive flow, hydrodynamic focusing, dielectrophoresis, and optical tweezing. Any suitable control device(s) may be used to control the flow of fluid and/or movement of the object 150 through the fluid channel 410. Some examples of suitable control devices include micropumps, direct current (DC) electrokinetic devices, dielectrophoresis electrodes, and/or hydrodynamic focusing channels.

The aperture layer 420 refers to an opaque or semi-opaque layer of material. It can be a separate layer, or can be can be a coating on the inside surface of the fluid channel 410. The coating can be a layer of metal (e.g., Au, Al, Ag, etc.) of suitable thickness. For example, the thickness can be about 300 nm to 500 nm thick in some cases.

The light transmissive regions 422(a) (e.g., holes) in the opaque or semi-opaque aperture layer 420 can be of any suitable shape (e.g., circular, rectangular, etc.). In the illustrated example, the light transmissive regions 422(a) are circular holes. The circular holes may be etched, for example, into the opaque or semi-opaque aperture layer 420 (e.g., a thin metallic layer). The circular holes may be filled with a transparent material in some cases. The light transmissive regions 422(a) may be in the form of a one-dimensional array of light transmissive regions 422(a), a two-dimensional array of light transmissive regions 422(a) or multiple arrays (one-dimensional and/or two-dimensional) of light transmissive regions 422(a). In some cases, the light transmissive regions 422(a) are in the form of a one-dimensional array diagonally extending across the fluid channel 410, as shown in FIG. 4(a). In other cases, the light transmissive regions 422(a) may be in the form of one or more slits. A slit can refer to an elongated opening such as a narrow rectangle. Each slit has suitable dimensions. The slits may have uniform dimensions or may have variable dimensions. The slits or array(s) can be oriented at any suitable angle or angles with respect to the longitudinal axis of the fluid channel 410. For example, a slit of one embodiment can extend diagonally across from one lateral side 416 to the other lateral side 418 of the fluid channel 410.

The light transmissive regions 422(a) can be of any suitable dimension. In some cases, the size (e.g., diameter) of each light transmissive region 422(a) can be around or less than a select wavelength (e.g., the wavelength of the excitation light 112(a)). In these cases, the light transmissive regions 422(a) can be used as a waveguide working in cutoff mode. That is, the light transmissive regions 422(a) only transmit light with a wavelength shorter than the size of the light transmissive regions 422(a). In one example, light transmissive regions 422(a) having the size of the wavelength of the excitation light 112(a) will transmit the excitation light 112(a) and any other light having a shorter wavelength.

In FIGS. 5(a) and 5(b), the optofluidic DEDD 100 includes a time-gated illumination source 110(a) (e.g., pulsed LED, pulsed laser, etc.) capable of providing time-gated excitation light 112(a) (e.g., pulses of excitation light 112(a)) through the aperture array 422 to the fluid channel 410 during one or more excitation periods. The time-gated illumination source 110(a) may be placed in any suitable location and/or may include suitable components (e.g., lenses, reflective surfaces, apertures, etc.) to provide for directing time-gated excitation light 112(a) to the fluid channel 410. In FIGS. 5(a) and 5(b), for example, the illumination source 110 includes an aperture array 422 for localizing the excitation light 112 in the fluid channel 410. Although the illustrated example describes the illumination source 110(a) providing only time-gated excitation light 112(a), the time-gated illumination source 110(a) of other embodiments may provide other light or may provide time-gated excitation light 112(a) and other light.

The excitation light 112(a) in FIGS. 5(a) and 5(b) is time-gated (e.g., pulsed). The excitation light 112(a) may be any suitable type of light with any suitable property or properties (e.g., wavelengths, intensities, polarizations, phases, etc.).

The time-gated illumination source 110(a) of FIGS. 5(a) and 5(b) can provide excitation light 112(a) during one or more excitation periods. In FIGS. 5(a) and 5(b), the time-gated illumination source 110(a) is shown providing excitation light 112(a) through the aperture array 422 at $t=t_0$ at the beginning of an excitation period and ending before $t=t_1$. The intensity profile of the provided time-gated excitation light 112(a) on the temporal domain may form a square wave in some cases. In other cases, the intensity profile of the time-gated excitation light 112(a) may have other forms.

The duration of each of the excitation periods can be any suitable value. In some cases, a suitable duration may be in the range of a femtosecond to a millisecond. In embodiments with multiple excitation periods, the excitation periods can have constant value durations in some cases or durations with different values in other cases.

In embodiments with multiple excitation periods, the time-gated illumination source 110(a) can provide the time-gated excitation light 112(a) at any suitable rate (e.g., pulses/second). A suitable rate may be in the range of ten to one million pulses/second in some cases. The delay between excitation periods can be determined by the duration of the collection period(s) and any delay between the collection period and excitation period.

Any suitable object 150 or portion of an object 150 (e.g., cell nucleus) may be imaged or otherwise analyzed by the optofluidic DEDD 100. Suitable objects 150 can be biological or inorganic entities. Examples of biological entities include whole cells, cell components, microorganisms such as bacteria or viruses, cell components such as proteins, etc. Inorganic entities may also be imaged by embodiments of the invention. Although FIGS. 5(a) and 5(b) shows a single object 150, any number of objects 150 may be examined by the optofluidic DEDD 100.

In some cases, a reagent (e.g., dye) may be mixed with the sample having the object 150 before the sample is introduced into the optofluidic DEDD 100. The reagent tags portions of the object 150 to become fluorophore(s) having suitable emission properties (e.g., lifetime of the fluorescence/phosphorescence).

In FIGS. 5(a) and 5(b), the time-gated configuration is applied to avoid the excitation light 112(a). In this illustrated example, the emission properties (e.g., lifetime, decay rate, etc.) can be crucial for the signal to noise ratio (SNR) of the DEDD 100. Usually, the lifetime of organic fluorophores is only several nano-seconds. However, if a long life time dye (microsecond to millisecond) is applied, the SNR will be greatly improved.

The illumination setup in Scenario 2 is similar to the setup shown in FIG. 4(b). Just as shown in FIG. 4(b), the excitation light 112(a) is localized by an aperture array 422. The aperture array 422 has one or more light transmissive regions 422(a) (e.g., apertures). In some cases, the size of the light transmissive regions 422(a) could be similar or a little less than the wavelength.

Like Scenario 1, the rejection of excitation light 112(a) also relies on the time-gated strategy. Only a small area below the light transmissive region 422(a) is exposed to the excitation, so the resolution of a DEDD 100 may be determined by the size of the light transmissive region 422(a) in some embodiments. The size of the light transmissive region 422(a) may be smaller than the size of the light detector element 122(a) in some cases. For the same reason, instead of only one light detecting element 120(a) (e.g., pixel), the large area of the light detector 120 (e.g., imaging sensor) under the light transmissive region 422(a) collects the fluorescence emissions 115. A larger collection area can improve collection of the relatively weak emissions 115, which can decrease exposure time and thus increase imaging speed.

In FIGS. 5(a) and 5(b), the optofluidic DEDD 100 includes a light detector 120. The light detector 120 in this illustrated example is synchronized with the time-gated illumination source 110(a) to receive only or primarily emissions 115, and avoid receiving excitation light 112(a). Thus, the light detector 120 in this example only or primarily receives emissions 115 and generates signal(s) with only or primarily emissions data.

The light detector 120 of FIGS. 5(a) and 5(b) includes one or more discrete light detecting elements 120(a) (as shown in FIG. 4(c)). Each light detecting element 120(a) can generate a signal with light data based on light received. The light detecting elements 120(a) can be arranged in any suitable form such as a single light detecting element 120(a) (e.g., a photo-diode (PD), an avalanche photo-diode (APD) and a photomultiplier tubes (PMT)), a one-dimensional or two-dimensional array of light detecting elements 120(a) (e.g., coupled device (CCD) array, a complementary metal-oxide-semiconductor (CMOS) array, an APD array, a PD array, a PMT array, etc.), or a multiplicity of one-dimensional and/or two-dimensional arrays of light detecting elements 120(a). The arrays can be in any suitable orientation or combination of orientations. Other suitable light detectors 120 are commercially available. Each light detecting element 120(a) may be of any suitable size (e.g., 1-10 microns) and any suitable shape (e.g., circular or square).

In FIGS. 5(a) and 5(b), each light transmissive region 422(a) uniquely corresponds to a set of light detecting elements 120(a) proximal (e.g., beneath) the corresponding light transmissive region 422(a). Each set of light detecting elements 120(a) covers an area of the light detector 120. For example, if the light detector 120 is in the form of a two-dimensional array of light detecting elements 120(a), each set may be a lengthwise strip of one or more one-dimensional arrays of light detecting elements 120(a) in the direction of the x-axis. By covering more area, the set can more efficiently collect emissions 115 from the fluorophores activated by the localized excitation light 112(a) associated with the corresponding aperture 422(a), which can improve resolution.

In FIGS. 5(a) and 5(b), the light detector 120 receives and detects light on a time-varying basis during one or more collection periods of a capturing run. The light detector 120 captures time-varying light data during the capturing run including the one or more collection periods. Any suitable number (e.g., 1, 10, 100, 1000, etc.) of collection periods may be used. Since the light detector 120 is synchronized with the illumination source 110(a), the light detecting elements 120 (a) of the light detector 120 receive and detect only or primarily emissions 115 during the one or more collection periods, and generate signals with only or primarily time-varying emission data. The time-varying emissions data collected during the collection period(s) can be used to generate a fluorescent/phosphorescent image or otherwise analyze the object 150 or tagged portion of the object 150 in the sample. The time-varying data can be used to generate line scans, which can be used to reconstruct the image.

The time-varying emissions data and other time-varying light data may have any suitable information such as information about the properties (e.g., intensity, wavelength, frequency, polarization, phase, spin angular momentum, and other light properties) of the light detected by the light detector 120. Time-varying emissions data and other light data may also include the location of the light detecting element 120(a) receiving the light. Time-varying light data may also include, for example, the time that the light is detected, the time of the beginning of the corresponding collection period, an indicator of the cycle, or other information related to detecting light in a capturing run.

The DEDD 100 of FIGS. 5(a) and 5(b) uses one or more collection periods that occur after the end of an excitation period and before another excitation period begins. The light detector 120 and the illumination source 110 are synchronized so that the collection period is substantially separate from the excitation period so that the collection period does not overlap significantly with the excitation period. Each collection period may start immediately after the end of the excitation period or may start after a time delay after the end of an excitation period. For example, the time delay can be in the range of femtoseconds to nanoseconds.

In FIGS. 5(a) and 5(b), each of the one or more collection periods has the same duration (e.g., 1 second, 0.1 seconds, 0.01 seconds, 20 seconds, etc.). In some cases, the duration may be predetermined before the capturing run commences and remain constant during the capturing run. In one case, for example, the duration of the collection periods may be determined based on the flow rate and/or the lifetime of the fluorescence/phosphorescence. In other cases, the duration may be changed during the capturing run. For example, if higher resolution is desired during the capturing run, the duration of the collection periods may shortened. In one case, the collection period may end when it is determined that the detected emissions 115 have diminished to a predefined level.

In FIG. 5(a), the excitation period starts at $t=t_0$ and ends before the beginning of the collection period shown to start at $t=t_1$ in FIG. 5(b). In FIG. 5(b), the collection period is shown to start at $t=t_1$, after the end of the excitation period. The collection period ends before the start of any other excitation period. In this illustrated example, the collection period does not overlap with an excitation period. Since the collection period starts at $t=t_1$, after the end of the excitation period and ends before a possible other excitation period, the light detector 120 of FIGS. 5(a) and 5(b) receives and measures only emissions 115 during the first collection period. In some cases, there may be a suitable time delay between the collection period and the excitation period. A suitable time delay may be in the range of femtoseconds to nanoseconds. In other cases, the collection period may start immediately after the end of the excitation period without any delay. Although only a single cycle is shown in FIGS. 5(a) and 5(b), the optofluidic DEDD 100 can capture emissions 115 during any suitable number of cycles as the object 150 passes through the fluid channel 410.

In some cases, the light detector 120 may also detect light at times other than during the collection period(s). For example, the light detector 120 may detect light during the excitation period, or during a delay between a collection period and excitation period. The light detected during these times may be used, for example, to determine the intensity of the excitation light during the excitation period, determine the intensity of emissions between the excitation period and the collection period, etc. In another example, the light detector 120 may detect light during the entire cycle. A cycle includes an excitation period, a collection period and any delays between the periods. In this example, the DEDD 100 can use just the emissions data from the collection period(s) to analyze the sample.

In FIGS. 5(a) and 5(b), the light detector 120 is synchronized with the time-gated illumination source 110(a) using a suitable excitation (synchronization) strategy. This synchronization is used to avoid excitation light 112(a) being received at the light detector 120 during the collection period(s) without using a filter. As a result, the light detector 120 of the illustrated embodiments only measures emissions 115 during collection period(s).

One synchronization strategy is illustrated in FIGS. 5(a) and 5(b). In the illustrated example, the light detector 120 is synchronized to start a collection period after the end of an excitation period in a cycle. At $t=t_0$, the time-gated excitation light 112(a) excites the fluorophore(s) that tagged a region of the object 150. By $t=t_1$, the time-gated illumination source 110(a) has stopped providing excitation light 112(a), and due to the lifetime of the fluorescence/phosphorescence, the fluorophore(s) will continue to emit. The light detector 120 starts to collect emissions 115 at $t=t_1$. The time-gated illumination source 110(a) can also be synchronized to start any additional excitation period after the end of the collection period. In this case, the time-gated illumination source 110(a)) will be turned on again for the additional excitation period and another cycle begins.

Synchronization can be accomplished in any suitable way. In the illustrated example of FIGS. 5(a) and 5(b), the time-gated illumination source 110(a) and the light detector 120 are programmed to turn on and off again (starting and stopping the collection and excitation periods) based on predetermined durations of the respective excitation period(s) and collection period(s). At the end of the capturing run, the processor 210 sends a stop collection signal to the light detector 120 and/or a stop illumination signal to the time-gated illumination source 110(a) to end the cycles. In other embodiments, the time-gated illumination source 112(a) and the light detector 120 can be synchronized using signals sent to the components which trigger the turning on and off of functions of the components. In other embodiments, the time-gated illumination source 110(a) and the light detector 120 can be synchronized by initializing the light detector 120 after the time-gated illumination source 110(a) and then run the components at constant rates. In yet other embodiments, the time-gated illumination source 110(a) and the light detector 120 can be synchronized using a combination of signals sent to the components and initializing the light detector 120 after the time-gated illumination source 110(a) and then running the components at constant rates.

In embodiments using a start sampling signal, the light detector 120 may begin a collection period after receiving a start sampling signal. The start sampling signal is sent at the end of the excitation period or after some suitable delay has passed after the end of the excitation period. In some cases, the illumination source 110(a) may communicate the start sampling signal to the light detector 120. In these cases, the illumination source 110(a) may be communicatively connected to the light detector 120. In other cases, the processor 210 may send the start sampling signal.

In embodiments that use a start illumination signal, the illumination source 110(a) may start an excitation period after receiving a start illumination signal. In some cases, the light detector 120 may communicate the start illumination signal to the illumination source 110(a). In other cases, the start illumination signal may be sent from another source such as the processor 210.

In embodiments that use a stop sampling signal, the light detector 120 may end the collection period after receiving a stop sampling signal from the processor 210 or the illumination source. In some cases, the stop sampling signal may be sent after the processor 210 makes the determination that the emissions have decayed to predefined level.

In embodiments that use a start illumination signal, the time-gated illumination source 110(a) shown in FIGS. 5(a) and 5(b) provides excitation light 112(a) during one or more excitation periods, each excitation period having the same predetermined duration. The time-gated illumination source 110(a) in the illustrated example can be programmed to turn on and off again based on the predetermined duration. In other embodiments, the illumination source 110(a) may start an excitation period after receiving a start illumination signal. The start illumination signal may be sent at any time, for example, at the beginning of the first cycle, at the end of a collection period, or at the end of a delay after the end of a collection period.

(i) Method of Using DEDD Employing Scenario 2

Figure 6:
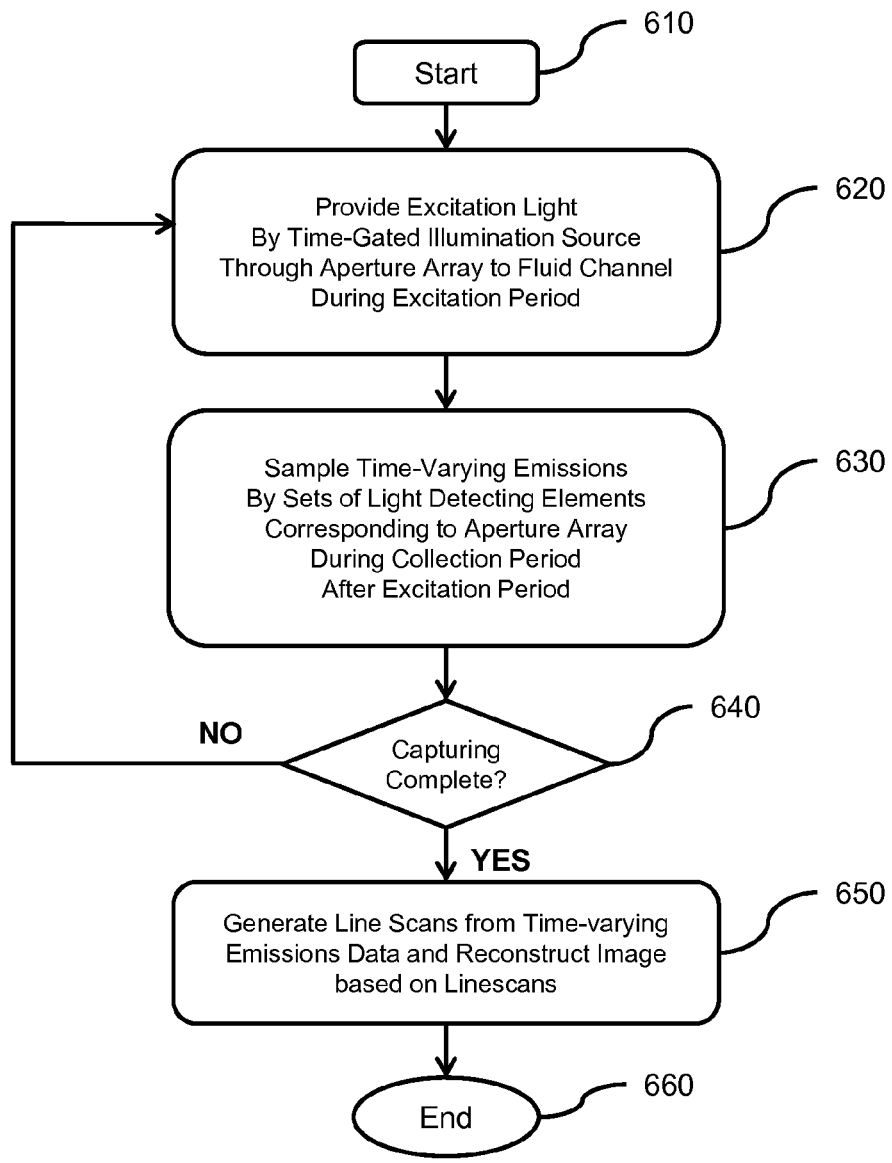
FIG. 6 is a flowchart of a method of using an optofluidic DEDD employing Scenario 2 to detect emissions, according to embodiments of the invention.

FIG. 6 is a flowchart of a method of using an optofluidic DEDD 100 employing Scenario 2 to detect emissions 115, according to embodiments of the invention. The method starts at step 610. In some cases, a reagent (e.g., dye) may be mixed with the fluid sample having the object 150 being examined. The reagent tags portion(s) (e.g., nucleus) of the object 150 (e.g., cell) to become fluorophores for a lifetime. The resulting fluid sample may be introduced to the optofluidic DEDD 100. For example, the fluid sample may be injected into an inlet 410(a) of the fluid channel 410 as shown in FIG. 4(b).

At step 620, a time-gated illumination source 110(a) provides excitation light 112(a) to the fluid sample in the fluid channel 410 through an aperture array 422. The light transmissive regions 422(a) in the aperture array 422 localize the excitation light 112(a). The time-gated illumination source 110(a) provides excitation light 112(a) during an excitation period of suitable predetermined duration. The predetermined duration may be based on the fluorophore used. In some cases, the duration of the excitation period can be in the range of femtosecond ($10^{-12}$) to millisecond. The fluorophore(s) in the tagged portion(s) absorb excitation light 112(a) and release emissions 115.

After the end of the excitation period or after a delay after the end of the excitation period, the light detector 120 starts receiving and detecting emissions 115 on a time-varying basis and the collection period begins at step 630. In this example, each of the collection periods has a constant and predetermined duration. In other examples, the duration of the collection periods may vary. In other embodiments, the time-gated illumination source 110(a) or the processor 210 may send a start sampling signal to the light detector 120 to start the collection period.

In this example, the light detector 120 includes sets of light detecting elements 120(a) corresponding to the aperture array 422 in the DEDD 100. Each set uniquely corresponds to a light transmissive region 422(a) in the aperture array 422. For example, a light detector 120 in the form of a two-dimensional array of light detecting elements 120(a) may include sets of one or more one-dimensional arrays of light detecting elements 120(a). Each set of light detecting elements 120(a) receives and detects time-varying emissions 115 associated with excitation light 112(a) from the corresponding light transmissive region 422(a). Each set of light detecting elements 120(a) generates signal(s) with time-varying emissions data based on the received emissions 115.

After the end of the collection period or after a delay after the end of the collection period, the processor 210 determines whether capturing is complete at step 640. If the processor 210 determines that capturing is not complete, the illumination source 110(a) automatically starts the next excitation period at the end of the collection period or after a delay after the end of the collection period. The time-gated illumination source 110(a) provides excitation light 112(a) for the next excitation period at step 620.

If the processor 210 determines that the capturing run is complete at step 640, then the cycles end. The processor 210 sends a stop illumination signal and/or a stop sampling signal to the illumination source 110(a) and the light detector 120 respectively. The processor 210 may determine that capturing is complete if a predefined duration of time has elapsed, if a predefined number of cycles has been reached, if the sample or object 150 has moved through the fluid channel 410 or has moved past the aperture array 422, if a certain analysis result was reached, or other determination that would indicate the end of the capturing run.

The processor 210 generates line scans from the time-varying emissions data. Each line scan can correspond to the time varying emission data from a set of light detecting elements 120(a) uniquely associated with a particular light transmissive region 422(a) at a certain y-location. The processor 210 can reconstruct a fluorescence/phosphorescence image of the object 150 from the linescans of different y-locations and the method ends at step 660. The processor 210 can also analyze the time-varying emissions data for other purposes.

(ii) Metal Probes Application

Instead of using small apertures (with size around or much smaller than light wavelength), small metal probes can also be used to induce fluorescence of the dye. The small metal probes work similar to a fluorescence scanning near-field optical microscope. Some examples of as fluorescence scanning near-field optical microscopes can be found in Frey, H. G., Witt, S., Felderer, K. and Guckenberger, R., "High-resolution imaging of single fluorescent molecules with the optical near-field of a metal tip," Physical Review Letters 93, 200801 (2004), and Sanchez, E. J., Novotny, L. and Xie, X. S., "Near-field fluorescence microscopy based on two-photon excitation with metal tips," Physical Review Letters 82, 4014 (1999), which are hereby incorporated by reference in their entirety for all purposes. Instead of using a single probe, there may be an array of the small tips. The surface mode can provide local excitation of the fluorescence, enabling high-resolution surface imaging.

FIG. 7 includes schematic drawings of a side view and bottom view of components of a optofluidic DEDD 100 employing Scenario 2 and having small metal probes, according to an embodiment of the invention. The small metal probes are metal tips arranged in a skew array.

In FIG. 7, the optofluidic DEDD 100 includes a multi-layered body 401, which defines or includes the fluid channel 410 having a fluid flow with an object 150 being examined (e.g., imaged). The fluid channel 410 has a first inner surface 412 and a second inner surface 414 on opposing sides of the fluid channel 410. The fluid channel 410 also has a third surface 416 and a fourth surface 418 on lateral sides of the fluid channel 410.

The body 401 also includes a probe layer 700 that is an inner surface layer of the fluid channel 410 and includes the second surface 414. The probe layer 700 has a probe array 710 including one or more small metal probes 712 having tips 714 (e.g., metal tips) extending into the fluid channel 410. The metal probes 712 localize the excitation light 112(a) to a strongly enhanced field at the tips 714. The metal probes 712 refer to any suitable devices that can localize time-gated excitation light 112(a) at their tips 714. For example, the metal probes 712 may be a metal tipped optical fibers illuminated by laser pulses.

The metal probes 712 can have suitable dimensions. For example, the metal probes 712 can have a diameter ranging from several tens of nanometers to several hundred nanometers, and have a height of about several hundreds of nanometers. The tips 714 can be made of metal such as gold, silver, or other metal that supports surface plasma. Inventors: please describe any detail for the metal probes. The diameter can be from several tens of nanometers to several hundred nanometers, and the height of the probes can be several hundreds of nanometers. The metal can be gold, silver and other metal that supports surface plasma.

The metal probes 712 are arranged in a skew array as shown in the bottom view of the probe layer 700. In other embodiments, the metal probes 712 may be in other arrangements. A protective transparent layer (not shown) may lie to the inside of the probe layer 700 in some cases. The optofluidic DEDD 100 also includes an x-axis, a y-axis, and a z-axis. The x-axis and y-axis lie in the plane of the first surface 412 of the aperture layer 420. The z-axis is orthogonal to this plane.

The body 401 also includes a light detector layer 430 including the light detector 120. The light detector 120 includes discrete light detecting elements 120(*a*) (as shown in FIG. 4(*c*)). In this embodiment, the light detector 120 is synchronized with the timing of the illumination by the metal probes 712 so that the light detector 120 receives and measures only or primarily emissions 115 emitted from fluorophore(s) in the object 150.

In operation, the probe array 710 provides localized excitation energy during an excitation period. The metal probes 712 in the probe array 710 localize the excitation energy at their tips 714 that extend into the fluid channel 410. As the object 150 moves in a fluid flow through the fluid channel 410, the object 150 passes under the metal probes 712. The excitation energy at the tips 714 activates the fluorophore(s) in tagged portions of the object 150. After the excitation period ends, the fluorophore(s) will continue to emit due to the lifetime of the fluorescence or phosphorescence. The light detector 120 starts to measure emissions 115 commencing the collection period after the excitation period. The cycling through excitation period followed by collection period continues as the object 150 moves through the fluid channel 410 until the capturing run is complete. As the object 150 moves in the fluid flow through the fluid channel 410, the light detecting elements 120(*a*) take time-varying emissions data of the intensity (and/or other light properties) of the emissions 115 during the collection periods. The time varying emissions data can be used to generate line scans associated with the y-locations of the probes 712. The time varying emissions data can then be used to reconstruct fluorescence and/or phosphorescence images of the object 150 and/or portions of the object 150 tagged with fluorophores or otherwise analyze the object 150. The images are reconstructed by appropriately shifting and assembling the line scans, and optionally other data such as rotation, velocity of the object 150, and changes in shape of the object 150, etc.

3. Scenario 3

The optofluidic DEDD 100 of Scenario 3 does not need a time-gated excitation/detection synchronization to reject the excitation light. Instead, the DEDD 100 of Scenario 3 takes advantage of the flow movements of the sample to avoid excitation light. Like Scenario 2, the DEDD 100 of Scenario 3 provides excitation light through a light transmissive region 422(*a*) into a fluid channel 410 with the sample. At $t=t_0$ the object 150 (e.g., cell) flows under the excitation light transmissive region 422(*a*) (e.g. apertures) and the fluorophore that tagged the object 150 will start to emit fluorescence. If the detection area/region 120(*b*) of the light detector 120 (sensor) is just under the light transmissive region 422(*a*), then the detected light signal will include both the excitation light and emissions 115. At $t=t_1$, the area of the object 150 that was excited at $t=t_0$ will flow to the detection region 120(*b*), which is located downstream of the light transmissive region 422(*a*). The detection region 120(*b*) is located at a distance downstream that avoids receiving most of the excitation light from the light transmissive region 422(*a*). At $t=t_1$, the area excited at $t=t_0$ emits emissions 115, and the detected light signal at the detection region 120(*b*) includes primarily or only emissions 115.

The DEDD 100 of Scenario 3 includes a continuous illumination source 110(*b*). Instead of using time-gated excitation, the DEDD 100 takes advantage of the long lifetime of certain dyes and the flow of the object 150 (e.g., cell) by using a detection region 120(*b*) on the light detector 120 located downstream of the excitation light aperture to reject excitation light. For an optofluidic DEDD 100 of this embodiment that uses dyes with microseconds or even milliseconds luminescence lifetime, the flow speed may be normally 500 to 3000 μm/sec.

FIGS. 8(*a*), 8(*b*) and 8(*c*) are schematic drawings of a side view of components of an optofluidic DEDD 100 employing Scenario 3 of the delayed detection strategy, according to an embodiment of the invention. The optofluidic DEDD 100 of 8(*a*), 8(*b*) and 8(*c*) includes a multi-layered body 401, which defines or includes the fluid channel 410. The fluid channel 410 has a first inner surface 412 and a second inner surface 414 on opposing sides of the fluid channel 410. Although not shown, the fluid channel 410 has a third inner surface 416 and a fourth inner surface 418 on opposing lateral sides of the fluid channel 410. The body 401 also includes an opaque or semi-opaque aperture layer 420 (e.g. thin metallic layer) that is an inner surface layer of the fluid channel 410 and includes the second surface 414. The aperture layer 420 has a light transmissive region 422(*a*) in it. In other embodiments, the aperture layer 420 may have additional light transmissive region 422(*a*). In FIGS. 8(*a*), 8(*b*) and 8(*c*), the multi-layered body 401 also includes a light detector layer 430 including a light detector 120. An optional protective transparent layer (not shown) may lie to the inside of the aperture layer 420 in some cases.

The optofluidic DEDD 100 of FIGS. 8(*a*), 8(*b*) and 8(*c*) also includes an illumination source 110(*b*) providing continuous light 112(*b*). In other embodiments, the illumination source 110(*b*) may be separate from the DEDD 100 and/or may provide time-gated illumination 110(*a*). In the illustrated example, the illumination source 110(*b*) projects continuous light 112(*b*) through the light transmissive region 422(*a*) to the fluid channel 410.

The light detector 120 in the light detector layer 430 includes discrete light detecting elements 120(*a*) (as shown in FIG. 4(*c*)). The light detector 120 also includes a detection region 120(*b*) comprising one or more light detecting elements 120(*a*) of the light detector 120. As shown, the centerline of the detection region 120(*b*) is located at a downstream (in the x-direction) distance, d, from the centerline of the light transmissive region 422(*a*). The detection region 120(*b*) has a width, w. The width, w, and downstream distance, d, can be designed to avoid the excitation light 112(*b*) from the light transmissive region 422(*a*) and receive emissions during the fluorescence/phosphorescence lifetime. Other embodiments may include one or more additional detection regions 120(*b*) located further downstream from the detection region 120(*b*) shown in 8(*a*), 8(*b*) and 8(*c*). These additional detection regions 120(b) may capture emissions at a later time than the detection region 120(b) shown in 8(a), 8(b) and 8(c).

The optofluidic DEDD 100 of 8(a), 8(b) and 8(c) also includes an x-axis, a y-axis (not shown), and a z-axis. The x-axis and y-axis lie in the plane of the first inner surface 412 of the light detector layer 430. The z-axis is orthogonal to this plane.

FIGS. 8(a), 8(b) and 8(c) also illustrate the operation of the optofluidic DEDD 100 at $t=t_0$, $t=t_1$, and $t=t_2$ of a cycle in a capturing run. Although a single cycle is shown, the capturing run may include any suitable number of cycles. During the capturing run, the illumination source 110(b) provides continuous excitation light 112(b) to the light transmissive region 422(a), which localizes the continuous excitation light 112(b) in the fluid channel 410. A detection region 120(b) located at a distance downstream of the light transmissive region 422(a) to avoid excitation light, captures time-varying emissions data of the intensity (and/or other properties) of the emissions 115 as the object 150 (e.g., cell) moves through the fluid channel 410 during the capturing run.

In FIG. 8(a), the object 150 is shown proximal the light transmissive region 422(a) at $t=t_0$, as the localized excitation light illuminates the object 150 and the first inner surface 412 of the fluid channel 410. The continuous excitation light 112(b) activates the fluorophore(s) at a first area 114(a) (shown in FIG. 8(b) at a downstream portion of the object 150. After being activated, the fluorophore(s) in the first area 114(a) begin to emit emissions 115(a) and will continue to emit during the lifetime of the fluorescence/phosphorescence.

FIG. 8(b) illustrates the optofluidic DEDD 100 at $t=t_1$ (e.g., 10 milliseconds after $t=t_0$) of the cycle. At this time, the object 150 has moved downstream from the location at $t=t_0$. The first area 114(a) of the object 150 with fluorophore(s) activated by the excitation light at $t=t_0$ and releasing emissions 115(a) is located proximal the detection region 120(b) at $t=t_1$. At $t=t_1$, the continuous excitation light 112(b) activates fluorophore(s) in a second area 114(b) area at an upstream portion of the object 150. After being activated, the fluorophore(s) in the second area 114(b) begin to emit emissions 115(b). The emissions 115(b) from the fluorophore(s) in the second area 114(b) will not be received by the detection region 120(b) at $t=t_1$ because the location is far from or not within range of the detection region 120(b).

FIG. 8(c) illustrates the optofluidic DEDD 100 at $t=t_2$ of the cycle. At this time, the object 150 has moved downstream of its location at $t=t_1$. At this time $t=t_2$, the first area 114(a) of the object 150 activated by the excitation light at $t=t_0$ (as shown in FIG. 8(b)) continues to release emissions 115(a) as shown in FIG. 8(c), but at a lower intensity. The second area 114(b) area of the object 150 activated earlier at $t=t_1$ is releasing emissions 115(b) at a higher intensity than the intensity of emissions 115(a) activated at $t=t_0$ from the first area 114(a). At $t=t_2$, the detection region 120(b) is close enough to both the first area 114(a) and the second area 114(b) of the object 150 to receive emissions 115(a) from both areas. At $t=t_2$, the detection region 120(b) receives the lower intensity emissions 115(a) from fluorophore(s) in the first area 114(a) and the higher intensity emissions 115(b) from the fluorophore(s) in the second area 114(b).

During the capturing run, the detection region 120(b) captures time-varying emissions data of the intensity (and/or other light properties) of the emissions 115 as the object 150 moves through the fluid channel 410. The time varying emissions data can be used to generate line scans associated with y-locations based on the light detecting elements 120(a) receiving the light. In embodiments with more than a single light transmissive region 422(a), the time varying emissions data can be used to generate line scans associated with y-locations of corresponding light transmissive regions 422(a). The line scans and other time varying emissions data can be used to reconstruct fluorescence/phosphorescence images of portions or all of the object 150 or otherwise analyze the object 150. The images are reconstructed by appropriately shifting and assembling the line scans, and optionally other data such as rotation, velocity of the object 150, and changes in shape of the object 150, etc.

The layers of the multi-layer body 401 may be made of any suitable material (e.g., fused silica (glass), Polydimethylsiloxane (PDMS) or other polymer) or combination of materials of any suitable thickness or thicknesses, and may include suitable device(s) (e.g., light detector 120). In one exemplary embodiment, the multi-layer body 401 consists of a micromolded PDMS microfluidic chip bonded directly to a CMOS sensor. In some cases, the multi-layer body 401 may be fabricated using standard semiconductor and micro/nanofabrication procedures. Although the illustrated example shows certain layers in the multi-layer body 401, other embodiments may integrate, omit, or add one or more layers or change the location of one or more layers in the multi-layer body 401. Also, other embodiments may have a monolithic body 401.

In FIGS. 8(a), 8(b) and 8(c), the fluid channel 410 includes a first surface 412 and an opposing second surface 414. Although not shown, the fluid channel 410 also includes lateral surfaces including a third surface 416 and an opposing fourth surface 418. The fluid channel 410 also has a longitudinal axis along the x-axis. Although a single fluid channel 410 is shown in FIGS. 8(a), 8(b) and 8(c), other embodiments may include additional fluid channels 410 for parallel processing. Although not shown, the fluid channel 410 may also include an inlet 410(a) and an outlet 410(b) (as shown in FIG. 4(b)).

The dimensions of the fluid channel 410 may be of any suitable size. For example, the width and/or height of the fluid channel 410 may each be less than about 10 microns, 5 microns, or 1 micron. In some embodiments, the dimensions (geometry) of the fluid channel 112 are sized to improve or maximize image quality. For example, the channel height may be sized based on the size of the objects 150 being imaged to flow the objects 150 close to the first surface 412, which may improve image quality.

The fluid channel 410 can have any suitable shape (e.g., linear, U-shaped, S-shaped, substantially circular shaped, etc.). An example of a U-shaped fluid channel 410 can be found in FIG. 4(b). In non-linear shaped fluid channels 410, the fluid channel 410 can be comprised of a series of straight portions and/or curved portions.

The fluid channel 410 may include a fluid flow that carries a fluid sample with one or more objects 150 being imaged or otherwise analyzed through the fluid channel 410 in the general direction of the longitudinal axis of the fluid channel 410. Any suitable technique of controlling fluid flow and/or particulate transport can be used to move the object(s) 150 through the fluid channel 410. Some convention techniques include pressure driven flow, electrokinetic transport, discrete droplet translocation via electrowetting, or thermocapilarity techniques. Other techniques may include gravity drive flow, hydrodynamic focusing, dielectrophoresis, and optical tweezing. Any suitable control device(s) may be used to control the flow of fluid and/or movement of the object 150 through the fluid channel 410. Some examples of suitable control devices include micropumps, direct current (DC) electrokinetic devices, dielectrophoresis electrodes, and/or hydrodynamic focusing channels.

In optofluidic embodiments, a fluid flow with the sample having the object 150 moves through at least a portion of the fluid channel 410 during a capturing run. The fluid flow has a flow rate (speed). The flow rate may be constant. In some cases, the DEDD 100 may be designed with a flow rate that can allow for effectively measurement of emissions at the detection region 120(b) downstream of the light transmissive region 422(a). In these cases, a flow rate may be selected, based on the lifetime of the fluorescence/phosphorescence dye, that will allow an object 150 to flow from an area in the fluid channel 410 illuminated by continuous excitation light 112(b) to an area proximal the detection region 120(b) before the end of the lifetime of the fluorescence. In one example, the flow rate may be set to be in range of 500 to 3000 μm/sec for fluorescence/phosphorescence dyes with microseconds or milliseconds luminescence lifetime.

The aperture layer 420 refers to an opaque or semi-opaque layer of material. It can be a separate layer, or can be can be a coating on the inside surface of the fluid channel 410. The coating can be a layer of metal (e.g., Au, Al, Ag, etc.) of suitable thickness. For example, the thickness can be about 300 nm to 500 nm thick in some cases.

In FIGS. 8(a), 8(b) and 8(c), the light transmissive region 422(a) in the opaque or semi-opaque aperture layer 420 can be of any suitable shape (e.g., circular, rectangular, etc.). In the illustrated example, the light transmissive region 422(a) is a hole. The hole may be etched, for example, into the opaque or semi-opaque aperture layer 420 (e.g., a thin metallic layer). The hole may be filled with a transparent material in some cases. In some cases, the light transmissive region 422(a) may be in the form of one or more slits (i.e. elongated openings) having suitable dimensions. If more than one slit, the slits may have uniform dimensions or may have variable dimensions. The slits can be oriented at any suitable angle or angles with respect to the longitudinal axis of the fluid channel 410.

In other embodiments, the opaque or semi-opaque aperture layer 420 may include more than one light transmissive region 422(a) in the form of a one-dimensional array of light transmissive regions 422(a), a two-dimensional array of light transmissive regions 422(a) or multiple arrays (one-dimensional and/or two-dimensional) of light transmissive regions 422(a). For example, the light transmissive regions 422(a) may be in the form of a one-dimensional array diagonally extending across the fluid channel 410, as shown in FIG. 4(a). The array(s) can be oriented at any suitable angle or angles with respect to the longitudinal axis of the fluid channel 410.

The light transmissive region 422(a) can be of any suitable dimension. In some cases, the size (e.g., diameter) of the light transmissive region 422(a) can be around or less than a select wavelength (e.g., the wavelength of the excitation light. In these cases, the light transmissive region 422(a) can be used as a waveguide working in cutoff mode. That is, the light transmissive region 422(a) only transmits light with a wavelength shorter than the size of the light transmissive regions 422(a). In one example, the light transmissive region 422(a) having the size of the wavelength of the excitation light will transmit the excitation light and any other light having a shorter wavelength.

In one embodiment, the light transmissive region 422(a) may be configured or equipped such that scatter of the excitation light 112(b) within the fluid channel 410 is reduced. For example, the light transmissive region 422(a) may include a lenslet to focus the excitation light 110(b).

In FIGS. 8(a), 8(b) and 8(c), the optofluidic DEDD 100 includes a continuous illumination source 110(b) capable of providing continuous excitation light 112(b) through the light transmissive region 422(a) to the fluid channel 410. For example, the illumination source 110(b) may be a continuous wave laser or a common LED, etc. As another example, the illumination source 110(b) may be a nondiffracting beam generator (e.g., Bessel Beam generator). The continuous illumination source 110(b) may be placed in any suitable location and/or may include suitable devices (e.g., reflective surfaces, apertures, etc.) for directing continuous excitation light 112(b). In FIGS. 8(a), 8(b) and 8(c), for example, the illumination source 110 includes a light transmissive region 422(a) for localizing the continuous excitation light 112(b) in the fluid channel 410.

The continuous excitation light 112(b) may be any suitable type of light with any suitable property or properties (e.g., wavelengths, intensities, polarizations, phases, etc.) for suitably activating fluorophore(s) in the object 150 to re-emit emissions 115. Although the illustrated example describes the illumination source 110 providing only continuous excitation light 112(b), the illumination source 110 of other embodiments may provide other light (e.g, time-gated light) or may provide continuous excitation light 112(b) and other light to the sample.

Any suitable object 150 or portion of an object 150 (e.g., cell nucleus) may be imaged or otherwise analyzed by the optofluidic DEDD 100. Suitable objects 150 can be biological or inorganic entities. Examples of biological entities include whole cells, cell components, microorganisms such as bacteria or viruses, cell components such as proteins, etc. Inorganic entities may also be imaged by embodiments of the invention. Although the illustrated example, shows a single object 150, any number of objects 150 may be examined by the optofluidic DEDD 100.

In some cases, a reagent (e.g., dye) may be mixed with the sample having the object 150 before the sample is introduced into the optofluidic DEDD 100. The reagent tags portions of the object 150 to become fluorophore(s) having suitable emission properties (e.g., lifetime). Usually, the lifetime of organic fluorophores can be about several nano-seconds. However, if a long life time dye (microsecond to millisecond) is applied, the signal to noise ration can be greatly improved in some cases.

In FIGS. 8(a), 8(b) and 8(c), the optofluidic DEDD 100 includes a light detector 120 having one or more discrete light detecting elements 120(a) (as shown in FIG. 4(c)). Each light detecting element 120(a) can generate a signal with light data based on light received. The light detecting elements 120(a) can be arranged in any suitable form such as a single light detecting element 120(a) (e.g., a photo-diode (PD), an avalanche photo-diode (APD) and a photomultiplier tubes (PMT)), a one-dimensional or two-dimensional array of light detecting elements 120(a) (e.g., coupled device (CCD) array, a complementary metal-oxide-semiconductor (CMOS) array, an APD array, a PD array, a PMT array, etc.), or a multiplicity of one-dimensional and/or two-dimensional arrays of light detecting elements 120(a). The arrays can be in any suitable orientation or combination of orientations. Other suitable light detectors 120 are commercially available. Each light detecting element 120(a) may be of any suitable size (e.g., 1-10 microns) and any suitable shape (e.g., circular or square).

The light detector 120 includes a detection region 120(b) (detection area) of light detecting elements 120(a) located about a centerline and at a downstream distance, d, in the x-direction from the centerline of the light transmissive region 422(a). The detection region 120(b) has a width, w, in the x-direction. In other embodiments, the light detector 120 may have additional detection regions 120(b) located further downstream of the detection region 120(b) of FIG. 8. In some cases, the detection region 120(b) includes all the light detecting elements 120(a) of the light detector 120. In other cases, the detection region 120(b) may be a portion or region (area) of the light detector 120.

The detection region 120(b) has design parameters including, for example, a downstream distance, d, and width, w, in the x-direction. These parameters are designed to locate the detection region 120(b) in an area that avoids excitation light 112(b) from the light transmissive region 422(a) and still receives emissions (e.g., 115(a) and/or 115(b)) from fluorophores activated by the continuous excitation light 112(b). The design of the downstream distance, d, and width, w, also accounts for the flow rate of the fluid flow in the fluid channel 410 and the lifetime of the fluorescence/phosphorescence. The design allows an object 150 to move in the fluid flow from an area of the fluid channel 410 illuminated by excitation light 112(b) to an area where the detection region 120(b) can receive emissions 115 from the object 150 before the end of the lifetime of the fluorescence. In some cases, the detection region 120(b) may be designed so that any portion (e.g., one light detecting element 120(a)) of the detection region 120(b) can receive emissions during the lifetime. In one example, the detection region 120(b) may be located just out of range from receiving continuous excitation light 112(b) projected from the light transmissive region 422(a). The downstream distance, d, may be calculated based on the geometry of the fluid channel 410 to avoid the continuous excitation light 112(b) as it spreads from the light transmissive region 422(a). The width, w, may be calculated so that some portion of the detection region 120(b) receives emissions during the lifetime of the based on the lifetime of the fluorescence/phosphorescence. In some cases, the flow rate and the detection region (e.g., downstream distance, width, etc.) are designed based on the lifetime of the fluorescence/phosphorescence dye to be able to effectively measure emissions and avoid excitation light 112(b). In one example, the flow rate may be set to be in range of 500 to 3000 μm/sec for fluorescence/phosphorescence dyes with microseconds or milliseconds luminescence lifetime.

The detection region 120(b) may include one or more sets of light detecting elements 120(a). Each set of light detecting elements 120(a) includes any suitable number of light detecting elements 120(a) (e.g., 1, 5, 10, 20, 100, etc.) in any arrangement. For example, the detection region 120(b) may include sets of one or more one-dimensional arrays of light detecting elements 120(a) in a light detector 120 comprising a two-dimensional array of light detecting elements 120(a). In some cases, there may be space between sets. In other cases, the sets can be arranged in a pattern (e.g., checkerboard, etc.) or randomly arranged. In embodiments, each set of light detecting elements 120(a) may correspond to a particular y-location.

In FIGS. 8(a), 8(b) and 8(c), the light detector 120 receives and detects light on a time-varying basis during the capturing run and measures time-varying light data. Since the detection region 120(b) is located only to receive and measure emissions 115, the light detector 120 detects time-varying emissions and measures time-varying emissions data during the capturing run. The time-varying emissions data collected during the capturing run can be used to generate a fluorescent/phosphorescent image or otherwise analyze the object 150 or portion of the object 150 (e.g., tagged portion) in the sample. For example, the time-varying emissions data from each set of light detecting elements associated with a y-location can be used to generate line scans for the associated y-location, which can be reconstructed to generate a fluorescence/phosphorescence image.

The time-varying emissions data and other time-varying light data may have any suitable information such as information about the properties (e.g., intensity, wavelength, frequency, polarization, phase, spin angular momentum, and other light properties) of the light detected by the light detector 120. Time-varying emissions data and other light data may also include the location of the light detecting element 120(a) receiving the light. Time-varying light data may also include, for example, the time that the light is detected, or other information related to detecting light in a capturing run.

(a) Method of Using DEDD Employing Scenario 3

Figure 9:
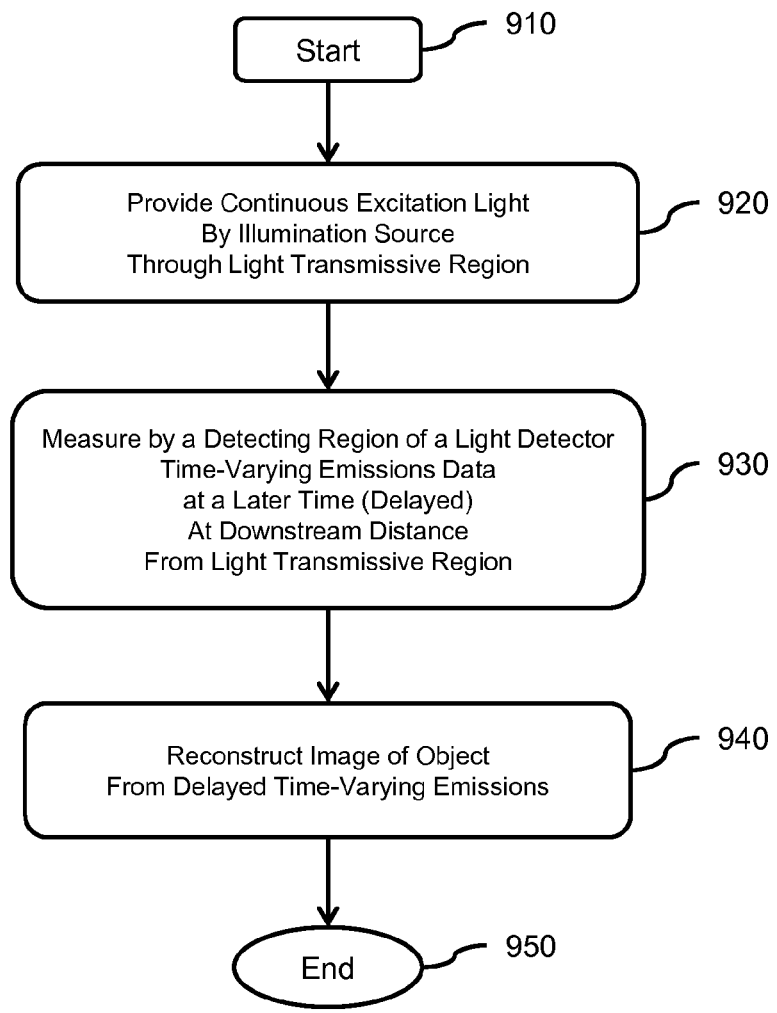
FIG. 9 is a flowchart of a method of using an optofluidic DEDD employing Scenario 3 to detect emissions, according to embodiments of the invention.

FIG. 9 is a flowchart of a method of using an optofluidic DEDD 100 employing Scenario 3 to detect emissions 115, according to embodiments of the invention. The method starts at step 910. In some cases, a reagent (e.g., dye) may be mixed with the fluid sample having the object 150 being examined. The reagent tags portion(s) (e.g., nucleus) of the object 150 (e.g., cell) to become fluorophores for a lifetime. The resulting fluid sample may be introduced to the optofluidic DEDD 100 at this step. For example, the fluid sample may be injected into an inlet 410(a) of the fluid channel 410 as shown in FIG. 4(b).

At step 920, a continuous illumination source 110(b) provides continuous excitation light 112(b) during a capturing run. The continuous light 112(b) passes through a light transmissive region 422(a) in an aperture layer 420 of a fluid channel 410. The continuous excitation light 112(b) from the light transmissive region 422(a) illuminates a local region of the fluid channel 410 around the light transmissive region 422(a). As an object 150 moves downstream, the object 150 moves through the illuminated region. After absorbing excitation light 112(b), fluorophore(s) in the object 150 will start to release emissions 115 and continue to emit during the lifetime of the fluorescence/phosphorescence.

For an object 150 that is larger than the size of the light transmissive region 422(a), different portions of the object 150 may move into the illuminated region at different times as the object 150 moves downstream. An example of different portions of an object 150 receiving excitation light 112(b) at different times is shown in FIGS. 8(a), 8(b), and 8(c). As shown, the portions 150(a) and 150(b) of the object 150 move through the illuminated region from the light transmissive region 422(a) at different times. The fluorophore(s) in the different regions 150(a) and 150(b) receive continuous excitation light 112(b) at different times and the intensity of the emissions 115 from the different portions 150(a) and 150(b) varies with time.

In FIG. 9, the light detector 120 of the DEDD 100 being used has a light detecting region 120(b) that is located at a downstream distance, d, from the light transmissive region 422(a). The downstream location of the detection region 120(b) is designed to avoid the continuous excitation light 112(b) from the light transmissive region 422(a) and receive only or primarily emissions 115. Since the detection region 120(b) is located downstream, the detection region 120(b) delays receiving and detecting emissions 115 associated with the excitation light projected through light transmissive region 422(a) at an earlier time. That is, the emissions 115 received by the light detecting region 120(b) are associated with excitation light 112(b) absorbed at an earlier time.

At step 930, the light detecting region 120(b) receives and detects emissions 115 on a time-varying basis and generates signal(s) with time-varying emissions data. The light detecting region 120(b) receives and detects the time varying emissions 115 during the capturing run as the object 150 moves in a fluid flow through the fluid channel 410. If the processor 210 determines that the capturing run is complete, the capturing run ends at step 950. In some cases, the processor 210 may send a stop collection signal to the light detector 120 and/or a stop illumination signal to the time-gated illumination source 110(*a*). The processor 210 may determine that the capturing run is complete if a predefined duration of time has elapsed, if the sample or object 150 has moved through the fluid channel 410 or has moved past the aperture array 422, if a certain analysis result was reached, or other determination that would indicate the end of the capturing run. Alternatively, a user may stop the DEDD 100 and the capturing run ends at step 950.

The processor 210 generates line scans from the time-varying emissions data. Each line scan can correspond to the time varying emission data associated with at a certain y-location. The processor 210 can reconstruct an image of the object 150 from the linescans and the method ends at step 950. The processor 210 can also analyze the time-varying emissions data for other purposes.

In another embodiment, the aperture layer 420 may have an aperture array 422 of light transmissive regions 422(*a*) extending in the y-direction from one lateral side 416 to the other lateral side 418 of the fluid channel 410. In these embodiments, a large object 150 may move across more than one illumination region from more than on light transmissive region 422(*a*) at the same time. In this embodiment, the light detector 120 includes a detection region having sets of light detecting elements 120(*a*) corresponding to the aperture array 422 in the DEDD 100. Each set uniquely corresponds to a light transmissive region 422(*a*) in the aperture array 422 and to a y-location of the light transmissive region 422(*a*). For example, a light detector 120 in the form of a two-dimensional array of light detecting elements 120(*a*) may include sets of one or more one-dimensional arrays of light detecting elements 120(*a*). Each set of light detecting elements 120(*a*) receives and detects time-varying emissions 115 associated with excitation light from the corresponding light transmissive region 422(*a*). Each set of light detecting elements 120(*a*) generates signal(s) with time-varying emissions data based on the received emissions 115.

(b) Other Optofluidic Embodiments

In one embodiment, a DEDD 100 using Scenario 1 can further include a fluid channel 410 and become an optofluidic DEDD 100. In this embodiment, the optofluidic DEDD 100 employing Scenario 1 includes a multi-layer body 501 defining or including the fluid channel 410 having a fluid flow with an object 150 being examined. A light detector 120 can lie in a light detector layer 430 outside the fluid channel 410. The light detector 120 may receive and detect emissions 115 at one or more sampling times or on a time-varying basis as the object 150 moves through the fluid channel 410.

In one embodiment, an optofluidic DEDD 100 employing either Scenario 2 or Scenario 3 may include a focused light beam array 114 (shown in FIG. 4(*c*)) instead of one or more light transmissive regions 422(*a*). In this embodiment, the optofluidic DEDD 100 uses the focused beam array 114 having one more focused beams 114(*a*) to generate localized excitation light in an array formation in the fluid channel 410. The optofluidic DEDD 100 can use the emission detection strategy of either Scenario 2 or 3 to avoid excitation light at the light detector 120. The light detector 120 primarily or only receives emissions 115 without using a filter and can generate signal(s) with time-varying emissions data.

Technique II

III. Reflective Coating on Surface of Emission Detection Device

The second technique uses a reflective coating on an inside surface of a fluid channel or one the inside surface of a channel outlier to reflect/collimate light to a light detector of an optofluidic emission detection device. An excitation light filter located between the fluid channel and light detector can pass emissions and reject excitation light. By reflecting light to the light detector, this second technique can improve collection of weak emissions. Collimation can allow for more effective elimination of excitation light by the filter.

A first configuration of the second technique can use a metal-coated channel or other channel with a reflective coating to detect fluorescence emissions from a full spatial angle. In this configuration, instead of coating only the top wall of the channel, the whole channel can be coated with metal, which serves as a minor to reflect the light to the light detector. A filter may be attached on top of the light detector. However, since the light may not be collimated in this configuration, the filter may not work effectively.

A second configuration of this second technique also uses a reflective coating. The coating is not limited to just the inside of the channel, but can also be on an outer structure, such as a channel outlier of a cylinder or parabolic cylinder. The focus line of the parabolic shape can coincide with the line of the excitation apertures, so that the excitation light or emissions will be collimated after the reflection and applied to the interference filter and/or light detector to achieve higher rejection of excitation or better detection of emissions.

Figure 10:
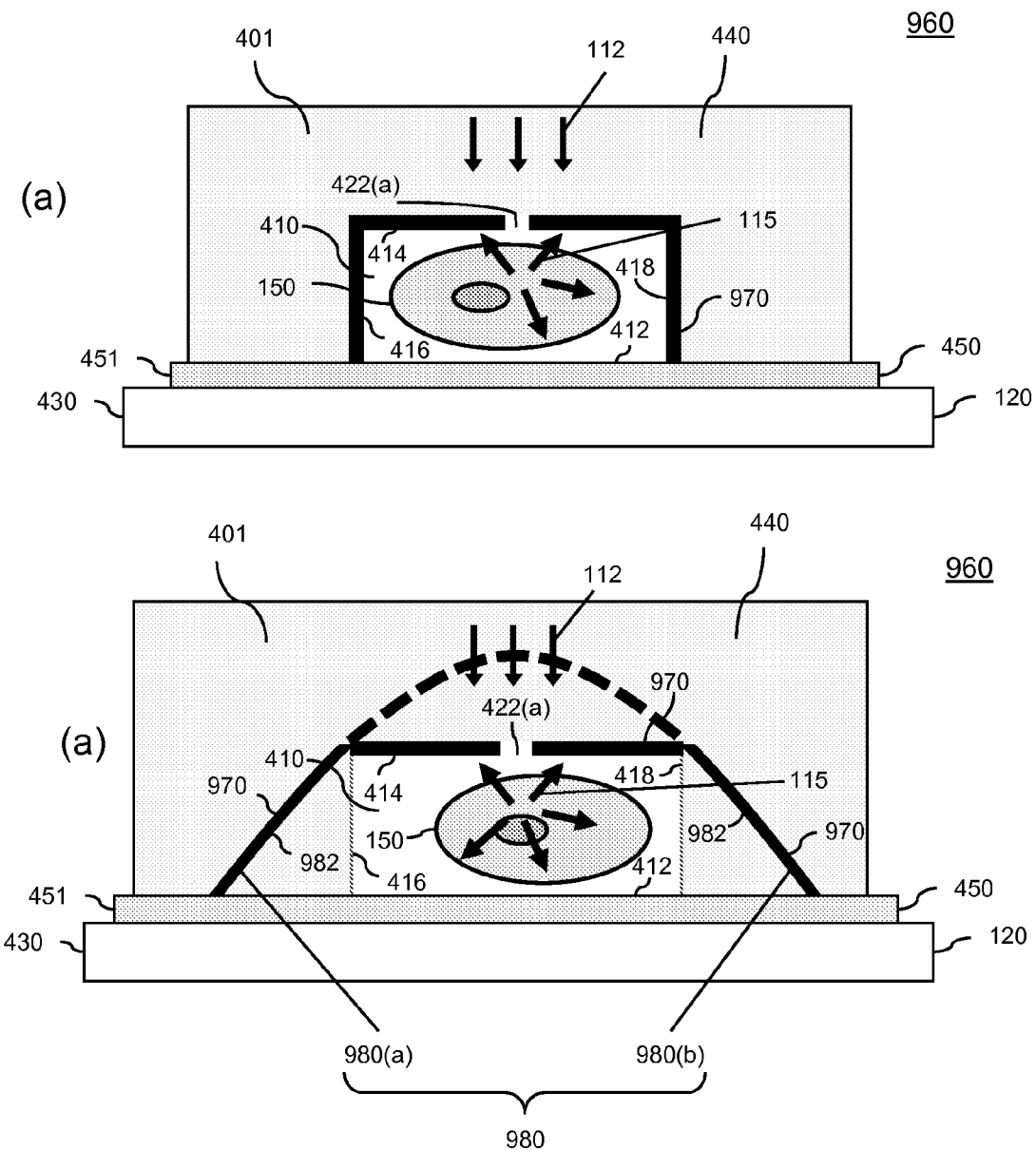
FIG. 10(a) is a schematic drawing of a front view of components of an optofluidic emission detection device having a reflective coating in a first configuration, according to an embodiment of the invention.
FIG. 10(b) is a schematic drawing of a front view of components of an optofluidic emission detection device having a reflective coating on a parabolic surface in a second configuration, according to an embodiment of the invention.

FIG. 10(*a*) is a schematic drawing of a front view of components of an optofluidic emission detection device 960 having a reflective coating 970 on the inside of a fluid channel 410 in a first configuration, according to an embodiment of the invention. The optofluidic emission detection device 960 includes a multi-layered body 401, which defines or includes the fluid channel 410. The fluid channel 410 has a first inner surface 412 and a second inner surface 414 on opposing sides of the fluid channel 410. The fluid channel 410 also has a third inner surface 416 and a fourth inner surface 418 on opposing lateral sides of the fluid channel 410. The body 401 also includes an opaque or semi-opaque aperture layer 420 (e.g. thin metallic layer) that is an inner surface layer of the fluid channel 410 and includes the second surface 414. The aperture layer 420 has a light transmissive region 422(*a*) in it. The body 401 also includes a filter layer 450 with a filter 451 outside the first inner surface 412 of the fluid channel 410. The body 401 also includes a light detector layer 430 outside the filter layer 450. The light detector layer 430 includes a light detector 120. The light detector 120 includes discrete light detecting elements 120(*a*) (as shown in FIG. 4(*c*)). A protective transparent layer (not shown) may lie to the inside of the aperture layer 420 in some cases.

The body 401 also includes a reflective coating 970 at the second inner surface 414, the third inner surface 416, and the fourth inner surface 418 of the fluid channel 410. The reflective coating 970 can be of any suitable material (e.g., metal) and any suitable thickness. For example, the reflective coating 970 may be made of metal such as gold, aluminum, or other metal that can block the transmission of the excitation light. The reflective coating 970 can have any suitable thickness (e.g., 100 nm, 300 nm, 1000 nm, etc.). In some cases, the thickness can be determined based on the wavelength and intensity of the excitation light.

During operation, the emission detection device 960 includes an object 150 receiving excitation light 112 through the light transmissive region 422(*a*). Fluorophores in the object 150 absorb excitation light 112 and release emission 115. Excitation light 112 and emissions 115 are reflected off the reflective coating 970 on the second inner surface 414, the third inner surface 416, and the fourth inner surface 418. The reflective coating 970 directs excitation light 112 and emissions 115 to a first surface 412 of the fluid channel 410. The filter in the filter layer 450 at the first surface 412 absorbs/reflects the excitation light 112 and passes emissions 115 to the light detector 120. In DEDD embodiments, the optofluidic emission detection device 960 does not need a filter.

FIG. 10(b) is a schematic drawing of a front view of components of an optofluidic emission detection device 960 having a reflective coating 970 in a second configuration, according to an embodiment of the invention.

In FIG. 10(b), the optofluidic emission detection device 960 includes a multi-layered body 401, which defines or includes the fluid channel 410. The fluid channel 410 has a first inner surface 412 and a second inner surface 414 on opposing sides of the fluid channel 410. The fluid channel 410 also has a third inner surface 416 and a fourth inner surface 418 on opposing lateral sides of the fluid channel 410. The body 401 also includes an opaque or semi-opaque aperture layer 420 (e.g. thin metallic layer) that is an inner surface layer of the fluid channel 410 and includes the second surface 414. The aperture layer 420 has a light transmissive region 422(a) in it. The body 401 also includes a filter layer 450 with a filter 451 outside the first inner surface 412 of the fluid channel 410. The body 401 also includes a light detector layer 430 outside the filter layer 450. The light detector layer 430 includes a light detector 120. The light detector 120 includes discrete light detecting elements 120(a) (as shown in FIG. 4(c)). The body 401 also includes a channel outlier 980 outside the fluid channel 410. The channel outlier 980 refers to a suitable structure outside the fluid channel 410 that can reflect and collimate light at or near the first inner surface 412 of the fluid channel 410. The body 401 also includes a transparent portion 440 between the fluid channel 410 and the channel outlier 980. A protective transparent layer (not shown) may lie to the inside of the aperture layer 420 in some cases.

The channel outlier 980 may be of any suitable shape. For example, the channel outlier 980 may be of a parabolic shape. If the channel outlier 980 is a parabolic shape, the channel outlier 980 may be designed to reflect and collimate light to a focus line at the first inner surface 412 of the fluid channel 410. In another example, the channel outlier 980 may be of a cylindrical shape.

In FIG. 10(b), the channel outlier 980 has a parabolic shape. The channel outlier 980 in the illustrated example includes two sides 980(a) and 980(b). Each of the two sides 980(a) and 980(b) of the channel outlier 980 also has an inner surface 982 with a reflective coating 970. The inner surface 982 has a parabolic shape with a focus line at the first inner surface 412 of the fluid channel 410. The second inner surface 414 of the fluid channel 410 also has a reflective coating 970. The reflective coating 970 can be of any suitable material (e.g., metal) and any suitable thickness.

During operation, the optofluidic emission detection device 960 includes an object 150 receiving excitation light 112 through the light transmissive region 422(a). Fluorophores in the object 150 absorb excitation light 112 and release emission 115. Light, both excitation light 112 and emissions 115, reflected off the reflective coating 970 on the second inner surface 414 and off the reflective coating 970 on the inner surface 982 of the channel outlier 980 is directed to the first surface 412 of the fluid channel 410. Light reflected off the reflective coating 970 on the inner surface 982 of the channel outlier 980 is collimated at the first inner surface 412 of the fluid channel 410. The filter in the filter layer 450 at the first surface 412 absorbs/reflects the excitation light 112 and passes emissions 115 to the light detector 120. In DEDD embodiments, the optofluidic emission detection device 960 does not need a filter.

In embodiments, the second technique of either the first or second configuration can be used to improve an emission detection device. In embodiments, the second technique of either configuration can be used in an optofluidic DEDD 100 employing Scenario 1, Scenario 2, or Scenario 3.

IV. Methods of Making DEDDs

The DEDD 100 and other emission detection devices of embodiments can be assembled in a suitable manner from components that are either commercially available or can be fabricated using well-known processes. For example, the DEDD 100 of embodiments can be assembled from commercially available light detectors 120 and naturally or commercially available illumination sources 110.

Any suitable combination of well known processes including etching, lamination, and soft lithography can be used to fabricate components of the DEDD 100 of embodiments of the invention. An exemplary method for fabricating components of the DEDD 100 and other emission detection devices of embodiments can be described with reference to FIGS. 11(a)-11(e).

Figure 11A:
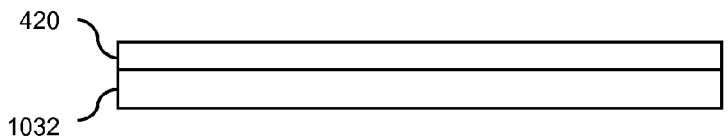
FIGS. 11(a)-11(e) are schematic drawings of an exemplary method for fabricating components of the DEDD and other emission detection devices, according to embodiments of the invention.

Fabrication of an aperture array 422 is shown in FIG. 11(a) and begins by first evaporating a layer 420 of material (e.g., layer of gold that is approximately 100 nanometers thick) on the transparent surface of a glass plate 1032. The glass plate 1032 could alternatively be some other transparent layer. The aperture layer 420 can be any suitable opaque or semi-opaque layer of material.

Figure 11B:

As shown in FIG. 11(b), a polymethylmethacrylate (PMMA) resist layer 1036 is then spun on the aperture layer 420 and standard electron-beam lithography is used to form a hole pattern in the PMMA resist 1036. Instead of a PMMA resist 1036, any other suitable type of photoresist may be used.

Figure 11C:
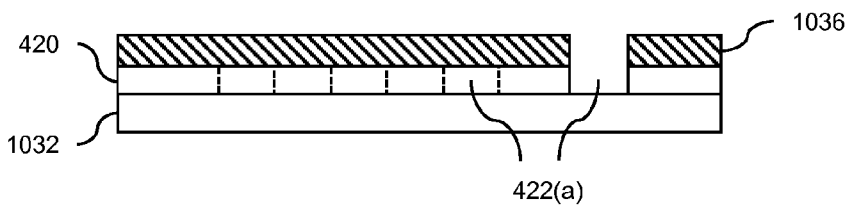

As shown in FIG. 11(c), after developing, the aperture layer 420 is wet etched thereby defining the light transmissive regions 422(a), which are holes in this embodiment. Alternatively, a dry etching process may be used to form the light transmissive regions 422(a). The holes may be filled with a transparent material in some embodiments.

In other embodiments, etching need not be used. For example, a laser ablation process can be used to form the light transmissive regions 422(a). In this case, a photoresist layer is not needed to form the light transmissive regions 422(a).

Figure 11D:
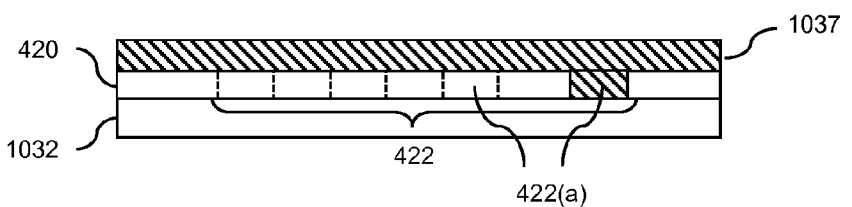

As shown in FIG. 11(d), the remaining PMMA layer 1036 is then removed and replaced with a new PMMA film 1037 (about 200 nanometers thick) which serves to electrically and mechanically isolate the imager from the fluidics portion in the fluid channel 410. Alternatively, instead of a PMMA film 1037, a different type of transparent or semi-transparent isolating material can be used.

The new PMMA film 1037, the prior PMMA layer 1036, and any other layer of the DEDD 100 may be deposited using any suitable process. Exemplary processes include roller coating, spin coating, vapor deposition, etc.

Figure 11E:
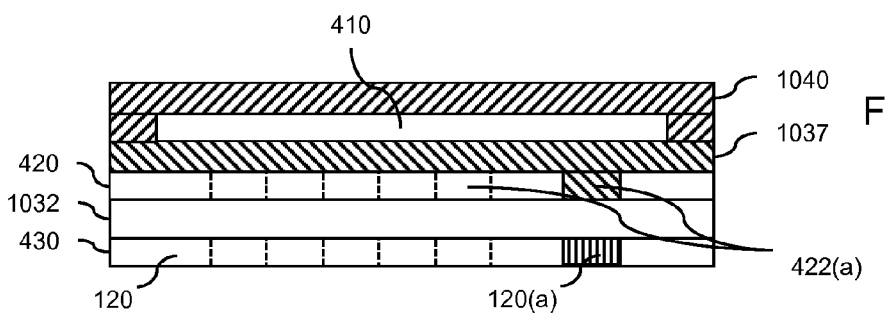

In the final assembly stage, as shown in FIG. 11(e), a poly dimethylsiloxane (PDMS) structure 1040 defining the fluid channel 410 can be pre-formed and then attached to the PMMA film 1037. Access holes (not shown) can then punched in the PDMS structure 1040 to form inlets and outlets to the fluid channel 410. The PDMS structure 1037 may be formed using a soft lithography technique (well known in the art) and is then exposed to air plasma for about 30 seconds. The PDMS layer 1040 and the PMMA film 1037 may be laminated together. After assembly, an 80 degree C. post bake can be used to help improve bonding strength between the various components of the DEDD 100.

Also, as shown in FIG. 11(e), a light detector 120 including discrete light detecting elements 120(a) can be attached to the glass plate 1032 using an adhesive or other suitable bonding mechanism to form components of the DEDD 100 according to an embodiment of the invention. As noted above, the light detector 120 may be a commercially available part.

V. Computer Devices

Figure 12:
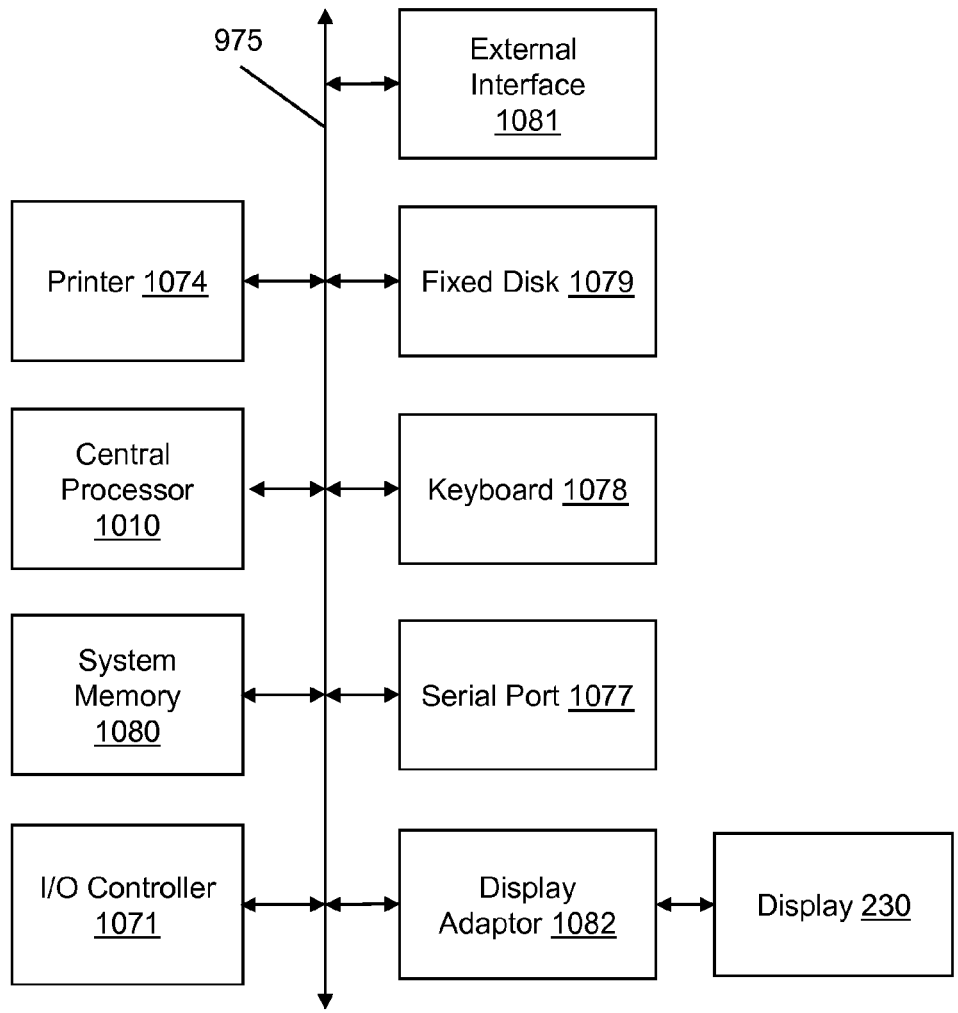
FIG. 12 is a block diagram of subsystems that may be present in computer devices that are used in the delayed emission detection system, according to embodiments of the invention.

FIG. 12 shows a block diagram of subsystems that may be present in computer devices that are used in the delayed emission detection system 10, according to embodiments of the invention. For example, the computer 200 in communication with the DEDD 100 may have any suitable combination of components in FIG. 12.

The various components previously described in the Figures may operate using one or more computer devices to facilitate the functions described herein. Any of the elements in the Figures may use any suitable number of subsystems to facilitate the functions described herein. Examples of such subsystems or components are shown in a FIG. 12. The subsystems shown in FIG. 12 are interconnected via a system bus 1075. Additional subsystems such as a printer 1074, keyboard 1078, fixed disk 1079 (or other memory comprising computer readable media), display 230, which is coupled to display adapter 1082, and others are shown. Peripherals and input/output (I/O) devices, which couple to I/O controller 1071, can be connected to the computer system by any number of means known in the art, such as serial port 1077. For example, serial port 1077 or external interface 1081 can be used to connect the computer apparatus to a wide area network such as the Internet, a mouse input device, or a scanner. The interconnection via system bus allows the central processor 210 to communicate with each subsystem and to control the execution of instructions from system memory 1080 or the fixed disk 1079, as well as the exchange of information between subsystems. The system memory 1080 and/or the fixed disk 1079 may embody a computer readable medium 220. Any of these elements may be present in the previously described features. A computer readable medium 220 according to an embodiment of the invention may comprise code for performing any of the functions described above.

In some embodiments, an output device such as the printer 1074 or display 230 of the delayed emission detection system 10 can output various forms of data. For example, the delayed emission detection system 10 can output a fluorescence/phosphorescence image of an object 150 or other results of analysis.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

A recitation of "a", "an" or "the" is intended to mean "one or more" unless specifically indicated to the contrary.

The above description is illustrative and is not restrictive. Many variations of the disclosure will become apparent to those skilled in the art upon review of the disclosure. The scope of the disclosure should, therefore, be determined not with reference to the above description, but instead should be determined with reference to the pending claims along with their full scope or equivalents.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

All patents, patent applications, publications, and descriptions mentioned above are hereby incorporated by reference in their entirety for all purposes. None is admitted to be prior art.

What is claimed is:

1. A delayed emission detection device comprising:
   a time-gated illumination source configured to provide excitation light to fluorophore during an excitation period; and
   a light detector configured to receive emissions from the fluorophore during a collection period after the excitation period, and further configured to receive and detect light during the excitation period.

2. The delayed emission detection device of claim 1, wherein the light detector is synchronized with the time-gated illumination source to receive emissions during the collection period after the excitation period.

3. The delayed emission detection device of claim 1, wherein the emissions are released from the fluorophore in response to excitation light provided to the fluorophore during the excitation period.

4. The delayed emission detection device of claim 1, wherein the collection period starts after the light detector receives a start sampling signal from the time-gated illumination source.

5. The delayed emission detection device of claim 1, wherein the light detector is further configured to receive and detect light during a delay between the excitation period and the collection period.

6. The delayed emission detection device of claim 1, further comprising a processor configured to generate a snapshot image based on the emissions received at the light detector at a sample time during the collection period.

7. A delayed emission detection device comprising:
   a time-gated illumination source configured to provide excitation light to fluorophore during an excitation period, and further configured to provide excitation light during another excitation period after the collection period once emissions decayed to a predefined level during the collection period; and
   a light detector configured to receive emissions from the fluorophore during a collection period after the excitation period.

8. A method of detecting emissions with a delayed emission detection device, the method comprising:
   providing, by a time-gated illumination source, excitation light to fluorophore during an excitation period;
   receiving, by a light detector, emissions from the fluorophore during a collection period after the excitation period;

receiving, by a processor, during the collection period a signal with emissions data from the light detector;

determining, by the processor, that the emissions received by the light detector are at a predefined level based on the emissions data; and upon the determination, sending a stop sampling signal to the light detector and sending a start excitation signal to the time-gated illumination source to provide excitation light during another excitation period.

9. The method of detecting emissions with the delayed emission detection device of claim 8, further comprising:

receiving, by the light detector, a start sampling signal from the time-gated illumination source to start the collection period.

10. The method of detecting emissions with the delayed emission detection device of claim 8, further comprising:

receiving, by a processor, a signal with emissions data from the light detector;

generating, by the processor, a snapshot image of an object based on the emissions data associated with emission received at the light detector at a sample time during the collection period, the object located between the light detector and the time-gated illumination source at the sample time.

11. A method of detecting emissions with a delayed emission detection device, the method comprising:

providing, by a time-gated illumination source, excitation light to fluorophore during an excitation period, wherein the excitation light is provided into a fluid channel through an aperture array;

receiving, by a light detector, emissions from the fluorophore during a collection period after the excitation period;

receiving, by a processor, a signal with time-varying emissions data from the light detector based on emissions received during the collection period;

generating linescans, by the processor, based on the time-varying emission data; and reconstructing, by the processor, an image of an object using the linescans, wherein the object is moving through the fluid channel between the light detector and the time-gated illumination source during the collection period.

12. An optofluidic delayed emission detection device comprising:

a body comprising a fluid channel having a surface layer with an aperture array;

a time-gated illumination source configured to provide excitation light to fluorophore in the fluid channel through the aperture array during one or more excitation periods; and a light detector configured to receive, from the fluid channel, emissions from the fluorophore during a collection period after each excitation period, wherein the light detector is further configured to detect light during one of the one or more excitation periods.

13. The optofluidic delayed emission detection device of claim 12, wherein the light detector is synchronized with the time-gated illumination source to receive emissions during each collection period after the one or more excitation periods.

14. The optofluidic delayed emission detection device of claim 12, wherein the emissions are released from the fluorophore in response to excitation light provided to the fluorophore during the excitation period.

15. The optofluidic delayed emission detection device of claim 12, wherein each collection period starts after the light detector receives a start sampling signal from the time-gated illumination source.

16. The optofluidic delayed emission detection device of claim 12, wherein the light detector is further configured to receive and detect light during a delay between one of the excitation periods and collection periods.

17. The optofluidic delayed emission detection device of claim 12, further comprising a processor configured to reconstruct an image of an object based on emissions received during the one or more collection periods as the object moves through the fluid channel.

18. An optofluidic delayed emission detection device comprising:

a body comprising a fluid channel having a surface layer with an aperture;

an illumination source configured to provide excitation light to fluorophore in a fluid channel through the aperture;

a light detector comprising a detection region located downstream from the aperture, the detection region configured to receive emissions from the fluorophore and avoid receiving excitation light through the aperture; and a processor configured to:

generate linescans based on emissions received as the object moves through the fluid channel; and reconstruct an image of the object based on the linescans.

19. The optofluidic delayed emission detection device of claim 18, wherein the emissions are released from the fluorophore in response to excitation light received through the aperture.

20. The optofluidic delayed emission detection device of claim 18, wherein the aperture is a slit extending from one lateral side to another lateral side of the fluid channel.

21. An optofluidic emission detection device comprising:

a body having a fluid channel, the body including first and second opposing surface layers proximal the fluid channel, the second surface layer having a light transmissive region, the fluid channel configured to receive excitation light from an illumination source through the light transmissive region;

a light detector located outside the first surface layer;

a filter located in the first surface layer, the filter configured to pass emissions from the fluid channel to the light detector; and a reflective coating in the body, the reflective coating configured to reflect light in the fluid channel to the first surface layer.

22. The optofluidic emission detection device of claim 21, wherein the reflective coating is located on an inner surface of the fluid channel.

23. The optofluidic emission detection device of claim 21, wherein the body further comprises a channel outlier having an inner surface with a portion of the reflective coating, wherein the portion of the reflective coating on the inner surface of the channel outlier is configured to collimate the reflected light to the light detector.

24. The optofluidic emission detection device of claim 23, wherein the inner surface of the channel outlier is a parabolic surface having a focus line in a plane parallel to a surface of the first surface layer.

* * * * *